United States Patent [19]
Moenning

[11] Patent Number: 5,951,588
[45] Date of Patent: Sep. 14, 1999

[54] APPARATUS AND METHOD FOR PROTECTING A PORT SITE OPENING IN THE WALL OF A BODY CAVITY

[76] Inventor: Stephen P. Moenning, 1940 Jamaica Way, Punta Gorda, Fla. 33950

[21] Appl. No.: 08/955,256

[22] Filed: Oct. 21, 1997

Related U.S. Application Data

[63] Continuation-in-part of application No. 08/656,430, May 30, 1996, Pat. No. 5,725,553, which is a continuation-in-part of application No. 08/608,644, Feb. 29, 1996, Pat. No. 5,766,220.

[51] Int. Cl.$^6$ ................................................. A61B 17/08
[52] U.S. Cl. ......................... 606/213; 606/198; 604/104
[58] Field of Search ..................... 606/213, 214, 606/191, 198; 604/96, 97, 98, 104

[56] References Cited

U.S. PATENT DOCUMENTS

| | | |
|---|---|---|
| 3,713,447 | 1/1973 | Adair . |
| 4,535,773 | 8/1985 | Yoon . |
| 4,601,710 | 7/1986 | Moll . |
| 4,875,897 | 10/1989 | Lee . |
| 4,931,042 | 6/1990 | Holmes et al. . |
| 5,066,288 | 11/1991 | Deniega et al. . |
| 5,114,407 | 5/1992 | Burbank . |
| 5,122,122 | 6/1992 | Allgood . |
| 5,147,316 | 9/1992 | Castillenti . |
| 5,152,754 | 10/1992 | Plyley et al. . |
| 5,203,773 | 4/1993 | Green . |
| 5,256,144 | 10/1993 | Kraus et al. . |
| 5,290,249 | 3/1994 | Foster et al. . |
| 5,318,580 | 6/1994 | Gresl . |
| 5,330,497 | 7/1994 | Freitas et al. . |
| 5,336,219 | 8/1994 | Krantz . |
| 5,338,305 | 8/1994 | Plyley et al. . |
| 5,342,383 | 8/1994 | Brinkerhoff et al. . |
| 5,345,927 | 9/1994 | Bonutti . |
| 5,346,459 | 9/1994 | Allen . |
| 5,350,393 | 9/1994 | Yoon . |
| 5,366,446 | 11/1994 | Tal et al. . |
| 5,366,478 | 11/1994 | Brinkerhoff et al. . |
| 5,368,545 | 11/1994 | Schaller et al. . |
| 5,370,647 | 12/1994 | Graber et al. . |
| 5,391,156 | 2/1995 | Hildwein et al. . |
| 5,395,335 | 3/1995 | Jang . |
| 5,445,615 | 8/1995 | Yoone ........................................ 604/96 |
| 5,462,529 | 10/1995 | Simpson et al. . |
| 5,549,595 | 8/1996 | Freitas . |
| 5,632,761 | 5/1997 | Smith et al. ............................. 606/192 |
| 5,634,937 | 6/1997 | Mollenauer et al. .................... 606/213 |
| 5,637,097 | 6/1997 | Yoon . |
| 5,658,272 | 8/1997 | Hasson ........................................ 606/1 |
| 5,830,232 | 11/1998 | Hasson .................................... 606/213 |

*Primary Examiner*—Michael Buiz
*Assistant Examiner*—Tina T. D. Pham
*Attorney, Agent, or Firm*—Maginot, Addison & Moore

[57] ABSTRACT

A medical apparatus includes a trocar assembly including a cannula and a trocar, wherein (1) the cannula has a lumen defined therein, (2) the trocar is positionable between a first trocar position and a second trocar position, (3) the trocar is positioned within the lumen of the cannula when the trocar is positioned at the first trocar position, and (4) the trocar is completely removed from the lumen of the cannula when the trocar is positioned at the second trocar position. The medical apparatus also includes a sleeve having a passageway extending therethrough, and a number of sealing members extending therefrom, wherein (1) the cannula is positionable between a first cannula position and a second cannula position, (2) the cannula is positioned within the passageway of the sleeve when the cannula is positioned at the first cannula position, and (3) the cannula is completely removed from the passageway of the sleeve when the cannula is positioned at the second cannula position. A medical procedure utilizing the medical apparatus is also disclosed.

19 Claims, 36 Drawing Sheets

APPARATUS AND METHOD FOR PROTECTING A PORT SITE OPENING IN THE WALL OF A BODY CAVITY

This application is a continuation-in-part of U.S. application Ser. No. 08/656,430, filed May 30, 1996, now U.S. Pat. No. 5,725,553, which is a continuation-in-part of U.S. application Ser. No. 08/608,644 filed Feb. 29, 1996, now U.S. Pat. No. 5,766,220.

BACKGROUND OF THE INVENTION

The present invention generally relates to an apparatus and method for protecting a port site wound in the wall of a body cavity. The present invention particularly relates to an apparatus and method for protecting a port site wound in the wall of a body cavity which is used with a trocar assembly.

Minimally invasive surgical techniques, such as laparoscopic surgery, typically include the use of a trocar assembly. A trocar assembly includes a trocar (sometimes referred to as an "obturator") positioned within the lumen of a cannula. The trocar and cannula are advanced through a body cavity wall so as to create a small hole or a port site wound therein. The trocar is then completely removed from the lumen of the cannula such that the cannula's lumen provides an entrance for laparoscopic instruments into the interior of the body cavity. The body cavity is then insufflated with an inert gas, such as $CO_2$, to provide easier access to the organs contained therein. Once the surgery is complete the cannula is completely removed from the port site wound to rapidly desufflate the body cavity.

Surgery performed by using minimally invasive techniques is generally associated with lower postoperative morbidity, shorter postoperative stay, less postoperative pain, decreased cost, and quicker recovery as compared to "open" or conventional surgical techniques[1, 2, 3, 4]. Because of the aforementioned advantages, these minimally invasive techniques are being applied to an increasing variety of all surgical procedures. For example, laparoscopic procedures for the resection of malignancies have emerged. In particular, laparoscopic colectomy for carcinoma of the colon has been developed, and it has been reported that the initial results of these procedures have advantages over operations performed in the traditional open manner[5, 6, 15]. Moreover, it is hoped that the long term results of these procedures will be comparable, or better than, those performed in the traditional open manner.

However, the development of laparoscopic surgery for cancer has been hindered because of the major concern regarding the implantation of tumor cells in the port site wound[2, 3, 6, 7]. In fact, numerous port site recurrences have been documented in the medical literature heretofore, and subcutaneous metastases after laparoscopic resection of malignant tissue is associated with a decreased survival rate for patients who may have had a curative cancer[2, 3, 6, 7]. Specifically, the medical literature reports that the incidence of tumor cell implantation ranges from as high as 20% to as low as 0%[8]. The studies generating the aforementioned data utilized highly skilled and experienced laparoscopic surgeons practicing at major university programs. However, in spite of utilizing highly skilled and experienced laparoscopic surgeons, the data indicates that the incidence of tumor cell implantation in the surgical wound is greater when employing laparoscopic techniques as compared to when conventional surgical techniques are used (i.e. 0.6% implantation incidence for conventional techniques[9] compared to 1% incidence for laparoscopic techniques[10]).

Several mechanisms may be responsible for the above discussed implantation of tumor cells in the port site wound. For example, minimally invasive surgical techniques for treating cancer require the insertion and removal of laparoscopic instruments or cameras through the lumen of the cannula. In addition, these surgical techniques require that the cannula itself be moved relative to the port site wound such that the cannula is advanced further into, or withdrawn from, the body cavity[11]. Moving the cannula in the above described manner facilitates a surgeon's ability to optimally locate instruments within the body cavity thereby helping to ensure the successful completion of the medical procedure. However, the aforementioned manipulations of the laparoscopic instruments and cannula may result in the exposure of the port site wound to exfoliated cancer cells which creates a risk of implanting tumor cells in the walls of the port site wound[11, 12]. In particular, exfoliated cancer cells may adhere to and thus contaminate a portion of the exterior surface of the cannula[11, 12]. The contaminated portion of the exterior surface of the cannula may then be advanced into contact with the port site wound during insertion and removal from the port site wound[11, 12]. This contact may dislodge the exfoliated cancer cells from the exterior surface of the cannula and thus cause the exfoliated cancer cells to be implanted in the port site wound[11, 12].

Furthermore, studies have shown that a physician may undergo a significant learning curve before becoming proficient in the performance of laparoscopic surgery, such as cancer surgery[3, 13]. As a result, a relatively inexperienced surgeon may have a tendency to manipulate or handle a tumor to a greater degree during a surgical procedure than an experienced surgeon. In addition, an inexperienced surgeon may have a tendency to insert and withdraw an instrument through the lumen of the cannula a greater number of times than an experienced surgeon. The above described increased manipulation of the instrument or the tumor can result in a greater incidence of tumor cell implantation in the port site wound[11, 12].

Regardless of how these cells contaminate the wound, once implanted therein, viable tumor cells can cause a subcutaneous metastases or "port/extraction site recurrence" after the resection of malignant tissue. These "port/extraction site recurrences" have delayed the advancement of laparoscopic cancer surgery[2, 6, 7, 8, 9, 10, 11, 12]. Therefore, it is desirable to provide an apparatus which will protect a port site wound from tumor cell implantation while allowing a surgeon to optimally locate instruments within the body cavity for successful completion of the medical procedure.

Furthermore, laparoscopic surgery performed for general surgery, gynecological surgery, urological surgery, or any other intra-abdominal infection is associated with a small but real incidence of port site wound infection[1]. The infecting bacteria causing these illnesses can contaminate the port site wound in the same manner as discussed above with regard to tumor cell contamination, and these infections can increase a patient's morbidity and consequently the length of a patient's hospital stay, thereby considerably increasing their hospital bill.

In addition, new technologies such as remote laparoscopic surgery (i.e. robotic laparoscopic surgery) are being introduced and utilized in the field of minimally invasive surgery [14]. During use of these new technologies the sensory feedback to the surgeon is decreased since robotic "arms" and "hands" (under the surgeon's control) manipulate the surgical instruments. The decrease in the surgeon's tactile sensory feedback can be a disadvantage when performing laparoscopic surgery for cancer. This is true since tactile feedback helps the surgeon avoid unnecessary manipulation of a tumor which may result in the implantation of tumor cells in the wall of the port site wound[2].

Therefore, in light of the above discussion, it is apparent that an apparatus which allows unrestricted movement of the cannula relative to the port site wound while preventing port site wound tumor cell implantation and reducing the incidence of port site wound infection, is desirable. The present invention provides such an apparatus in the form of a sleeve or a cannula which protects the port site wound. One advantage the present invention has over the prior art is that it can be retrofit to existing trocar assembly technology. More specifically, the sleeve of the present invention can be used with trocar assemblies which are currently commercially available to laparoscopic surgeons. Another advantage the present invention has over the prior art is that it allows the cannula to be advanced into and withdrawn from the port site wound while still protecting the port site wound from contamination by tumor or other types of cells. Moreover, once attached, the described invention adds only a minimal amount of bulk to the diameter of the trocar assembly.

TABLE OF REFERENCES CITED IN THE BACKGROUND

1. Lord et al., Dis. Col. Rect. 39(2): 148 (1996)
2. Berman, Important Advances in Oncology 1996, Laparoscopic Resection for Colon Cancer: Cause for Pause, Vincent DeVita Ed., p.231
3. Falk et al., Dis. Col. Rect. 36: 28 (1993)
4. Liberman et al., Surg. Endo. 10: 15 (1996)
5. Reiver et al., Dis. Col. Rect. 37: 22 (Podium Abstract 1994)
6. Regier, Gen. Surg. Lap. News 8: 1 (1995)
7. Greene, Semin. Lap. Surg. 2(3): 153 (1995)
8. Kazemier, Surg. Endo. 9: 216 (1995)
9. Reilly et al., Dis. Col. Rect. 39(2): 200 (1996)
10. Jacquet et al., Dis. Col. Rect. 38(10): 140 (1995)
11. Reymond et al., Surg. Endo. 11: 902 (1997)
12. Allardyce et al., Dis. Col. Rect. 40(8): 939 (1997)
13. Caushaj et al, Dis. Col. Rect. 37(4): 21 (Podium Abstract 1994)
14. Med. Simula. Train., 1(2): 7, 12–13, 20–28 (1996)
15. Fleshman et al., Dis. Col. Rect. 39(1): 15 (1996)

SUMMARY OF THE INVENTION

In accordance with one embodiment of the present invention, there is provided a medical apparatus which includes a trocar assembly including a cannula and a trocar, wherein (1) the cannula has a lumen defined therein, (2) the trocar is positionable between a first trocar position and a second trocar position, (3) the trocar is positioned within the lumen of the cannula when the trocar is positioned at the first trocar position, and (4) the trocar is completely removed from the lumen of the cannula when the trocar is positioned at the second trocar position. The medical apparatus also includes a sleeve having a passageway extending therethrough, and a number of sealing members extending therefrom, wherein (1) the cannula is positionable between a first cannula position and a second cannula position, (2) the cannula is positioned within the passageway of the sleeve when the cannula is positioned at the first cannula position, and (3) the cannula is completely removed from the passageway of the sleeve when the cannula is positioned at the second cannula position.

Pursuant to another embodiment of the present invention, there is provided a medical procedure which includes the following steps (1) creating an opening in a wall of a body cavity, (2) advancing a medical apparatus through the opening and into the body cavity, the medical apparatus including (a) a sleeve having a number of sealing members connected thereto and a passageway extending therethrough, (b) a trocar assembly positioned within the passageway of the sleeve, the trocar assembly including a cannula and a trocar, wherein (1) the cannula is completely removable from the passageway of the sleeve, (2) the cannula has a lumen defined therein, and (3) the trocar is completely removable from the lumen of the cannula, and (3) positioning the sealing members to contact an interior surface of the body cavity.

According to yet another embodiment of the present invention, there is provided a medical apparatus which includes a trocar assembly including a cannula and a trocar, wherein (1) the cannula has a lumen defined therein, and (2) the trocar is completely removable from the lumen of the cannula. The medical apparatus also includes a sleeve having a passageway extending therethrough and a number of sealing members extending therefrom, wherein (1) the cannula is completely removable from the sleeve, and (2) the sealing members are movable between (a) a first orientation in which the sealing members are positioned to facilitate advancement of the sleeve into an opening defined in a wall of a body cavity, and (b) a second orientation in which the sealing members are positioned to prevent fluid communication between an area inside of the body cavity and an area outside of the body cavity through a first space defined between the opening in the wall of the body cavity and the sleeve.

It is therefore an object of the present invention to provide a new and useful medical apparatus.

It is another object of the present invention to provide an improved medical apparatus.

It is still another object of the present invention to provide a new and useful medical apparatus for protecting a port site wound from tumor cell implantation or contamination with an infectious agent.

It is another object of the present invention to provide an improved medical apparatus for protecting a port site wound from tumor cell implantation or contamination with an infectious agent.

It is moreover an object of the present invention to provide a new and useful medical procedure for performing minimally invasive surgery.

It is still another object of the present invention to provide an improved medical procedure for performing minimally invasive surgery.

It is still another object of the present invention to provide a new and useful apparatus for manipulating sealing members of an apparatus which protects a port site wound.

It is yet another object of the present invention to provide an improved apparatus for manipulating sealing members of an apparatus which protects a port site wound.

It is also an object of the present invention to provide a new and useful method for manipulating sealing members of an apparatus which protects a port site wound.

It is still another object of the present invention to provide an improved method for manipulating sealing members of an apparatus which protects a port site wound.

It is also an object of the present invention to provide a medical apparatus for protecting a port site wound having a sleeve which can be used with trocar assemblies which are currently commercially available to laparoscopic surgeons.

It is yet another object of the present invention to provide a medical apparatus having a cannula which includes a plurality of sealing members for protecting a port site wound.

It is still another object of the present invention to provide a medical apparatus for protecting a port site wound which adds only a minimal amount of bulk to the diameter of a trocar assembly.

It is yet another object of the present invention to provide a medical apparatus which protects against the loss of the pneumoperitoneum.

It is still another object of the present invention to provide a medical apparatus which is securely positioned in the port site wound.

It is yet another object of the present invention to provide a medical apparatus which continuously protects the port site wound from tumor cell implantation, or contamination with an infectious agent, during the movement of a cannula relative to the port site wound.

The above and other objects, features, and advantages of the present invention will become apparent from the following description and attached drawings.

DETAILED DESCRIPTION OF THE PREFERRED EMBODIMENT

Figure 1:
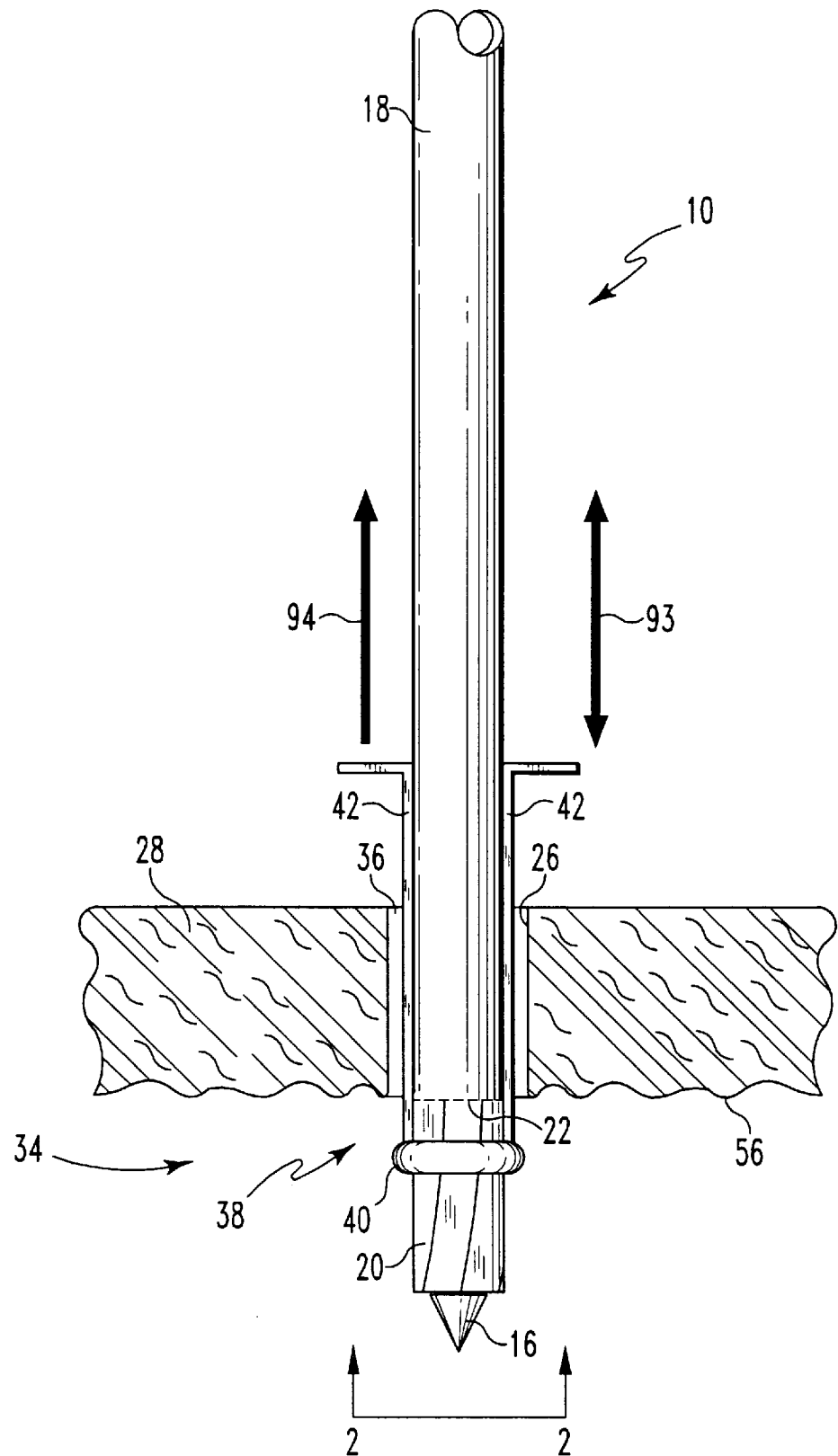
FIG. 1 is a fragmentary side elevational view of a medical apparatus inserted through a body cavity wall which incorporates the features of the present invention therein, with the body cavity wall shown in cross-section for clarity of description.

While the invention is susceptible to various modifications and alternative forms, a specific embodiment thereof has been shown by way of example in the drawings and will herein be described in detail. It should be understood, however, that there is no intent to limit the invention to the particular form disclosed, but on the contrary, the intention is to cover all modifications, equivalents, and alternatives falling within the spirit and scope of the invention as defined by the appended claims.

FIRST EMBODIMENT OF THE INVENTION

Figure 4:
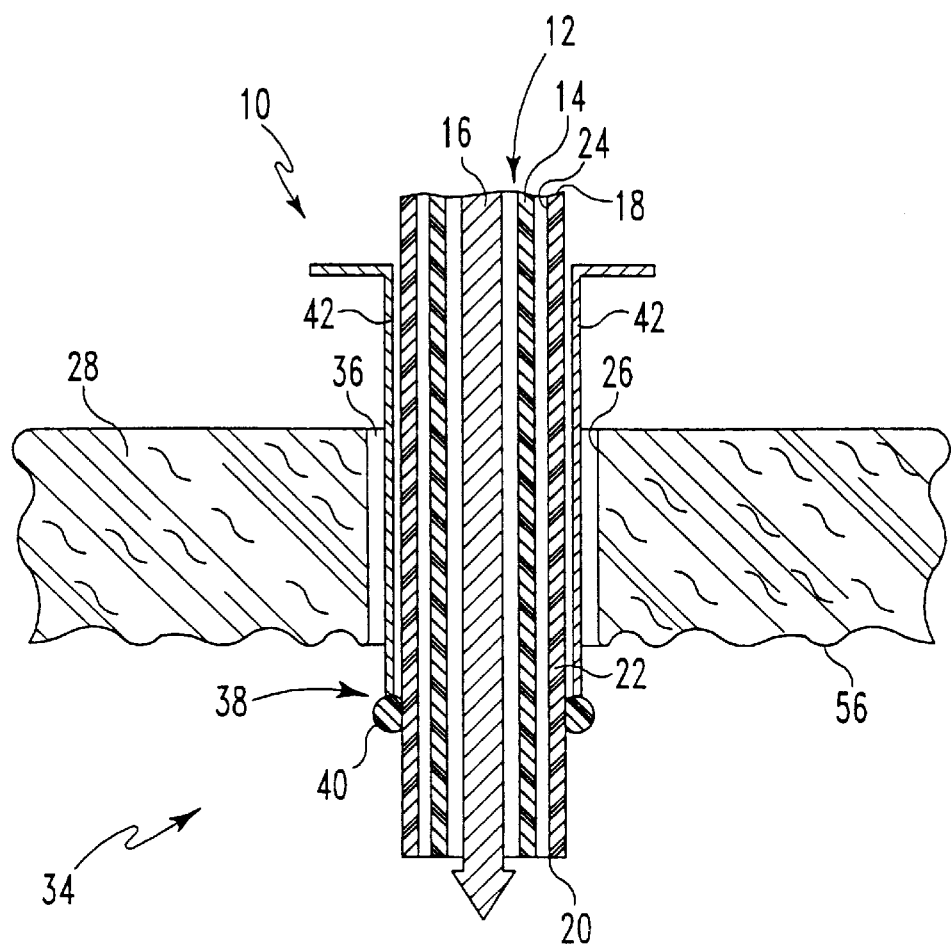
FIG. 4. is an enlarged cross sectional view of the medical apparatus of FIG. 1, with the guide member shown in a first position and the sealing members shown in a first orientation.
Figure 5:
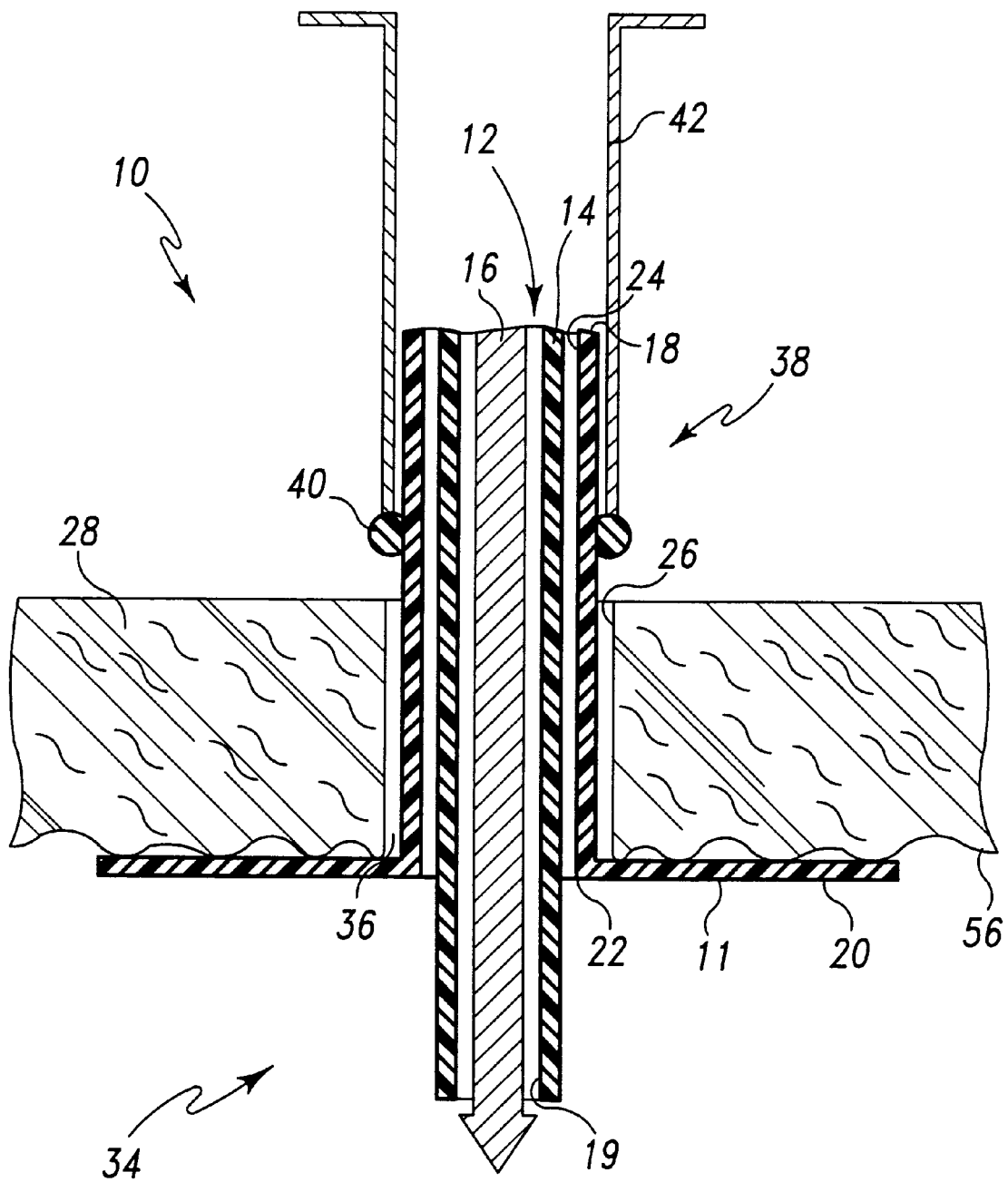
FIG. 5 is an enlarged cross sectional view of the medical apparatus of FIG. 1, with the guide member shown in a second position and the sealing members shown in a second orientation.

Referring to FIGS. 1, 4, and 5 there is shown a medical apparatus 10 of the present invention advanced through an opening 26 in a wall 28 of a body cavity 34. The medical apparatus 10 includes a sleeve 18 having a passageway 24 extending therethrough. The sleeve 18 includes a number of sealing members 20. Each sealing member 20 has an end portion 294 (see FIG. 6) and an end portion 296 (see FIG. 6). End portion 294 of each sealing member 20 is attached to a distal end 22 of sleeve 18 (see FIG. 6). Alternatively, each sealing member 20 can be attached to an exterior sidewall 113 (see FIG. 7) of sleeve 18. The medical apparatus further includes an actuator 38 and a trocar assembly 12. The actuator 38 includes a guide member 40 and handles 42.

Figure 2:
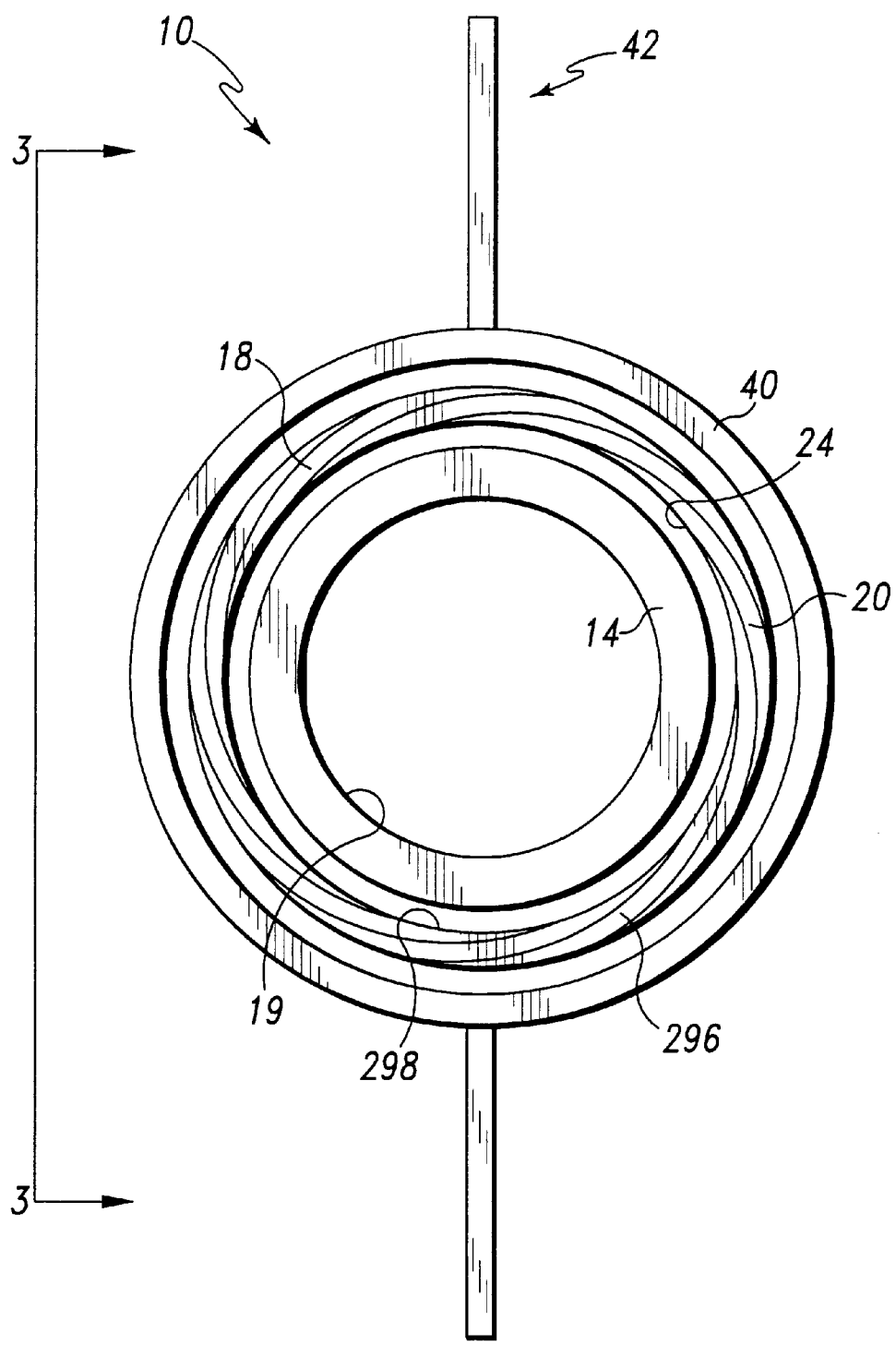
FIG. 2 is an enlarged end elevational view of the medical apparatus taken along line 2—2 of FIG. 1, with the trocar and body cavity wall shown removed for clarity of description.
Figure 3:
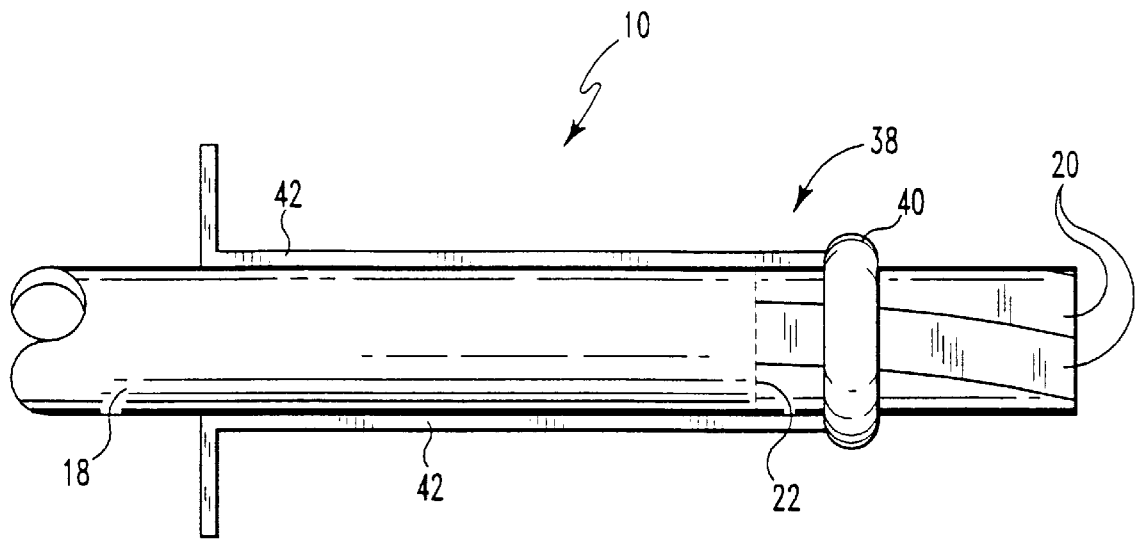
FIG. 3 is a reduced fragmentary side elevational view of the medical apparatus taken along line 3—3 of FIG. 2.
Figure 27:
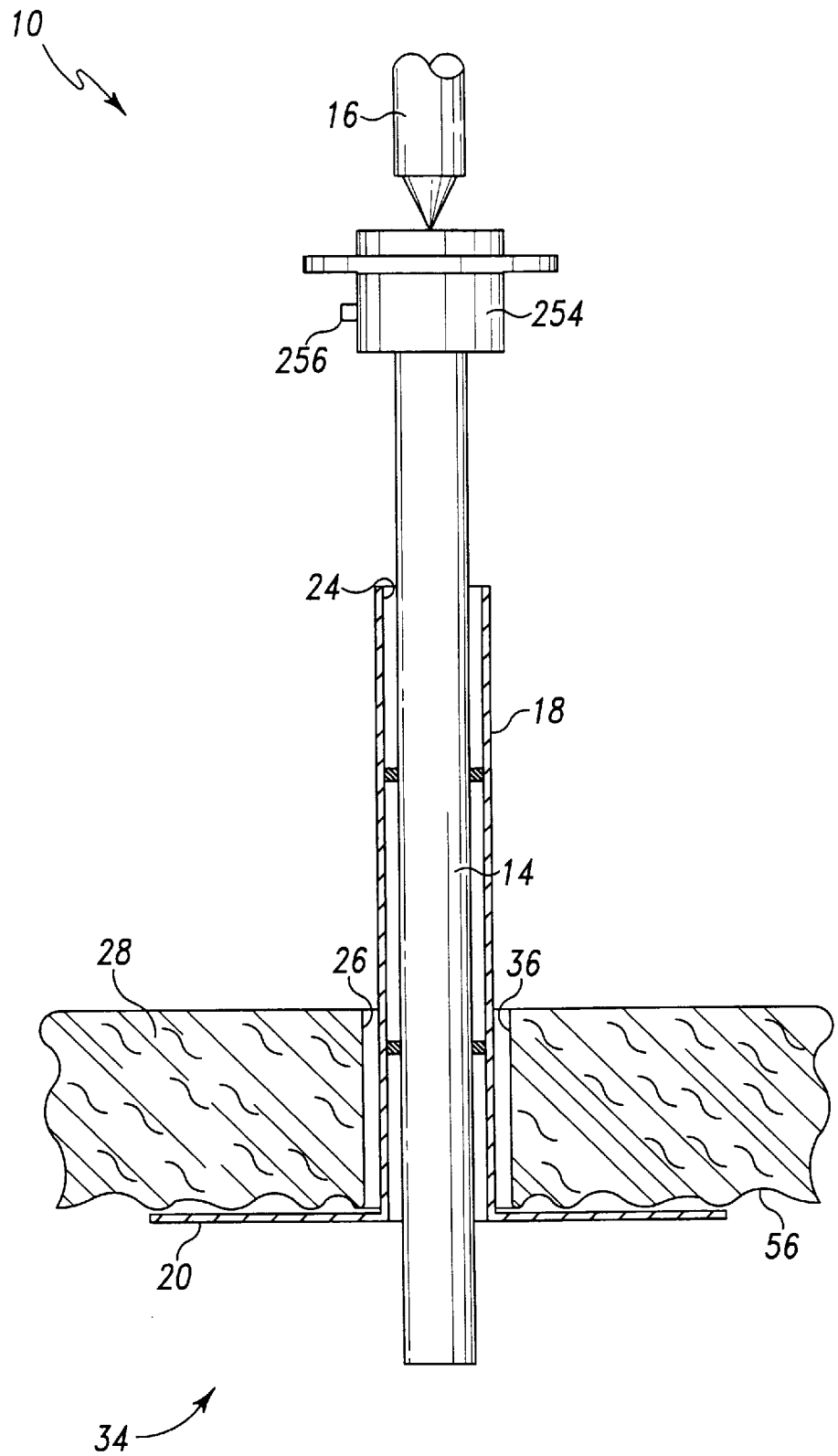
FIG. 27 is a side elevational view of the medical apparatus of FIG. 1 inserted through the body cavity wall but showing a valve assembly attached to an end of the cannula, the sealing members are shown in the second orientation and the trocar is shown completely removed from the cannula (note that the actuator is not shown, and the body cavity wall and the sleeve are shown in cross-section for clarity of description)

Trocar assembly 12 includes a cannula 14 having a lumen 19 extending therethrough, a trocar 16 (sometimes referred to as an "obturator"), and a valve assembly 254 (see FIG. 27). Trocar 16 is positioned within lumen 19 of cannula 14 (see FIG. 5). Valve assembly 254 is secured to an end of cannula 14 as shown in FIG. 27. As illustrated in FIG. 2, cannula 14 is positioned within passageway 24 of the sleeve 18 such that cannula 14, sealing members 20, and guide member 40 are all respectively nested within each other in a substantially concentric relationship. Note that trocar 16 is not shown in FIG. 2.

Trocar 16 is positionable between a first trocar position and a second trocar position. Trocar 16 is positioned at the first trocar position when trocar 16 is positioned within lumen 19 of cannula 14 as shown in FIG. 5. Trocar 16 is positioned at the second trocar position when it is completely removed from lumen 19 of cannula 14 as shown in FIG. 27.

Figure 26:
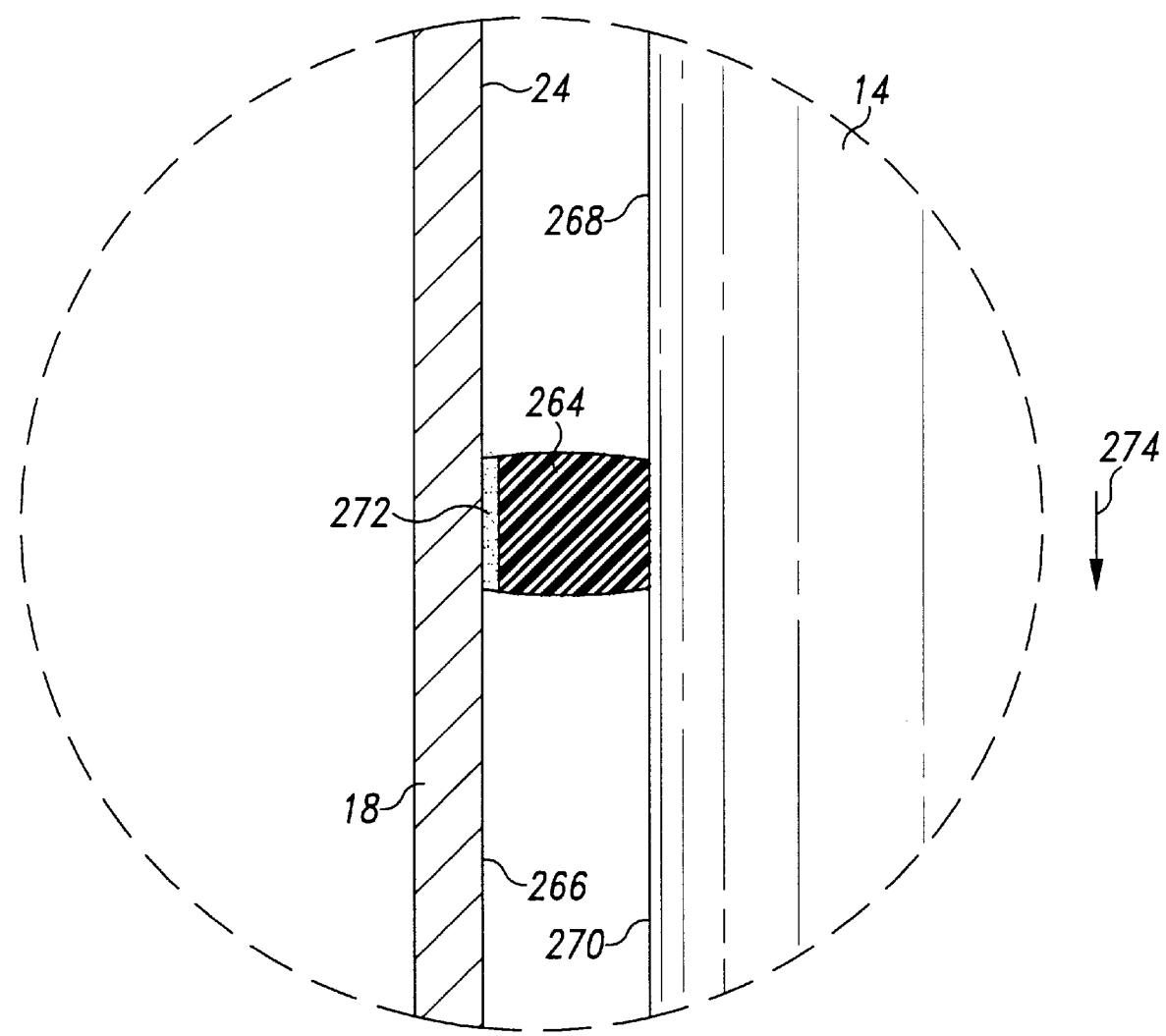
FIG. 26 is an enlarged view of a portion of FIG. 28 which is encircled and indicated as FIG. 26.
Figure 31:
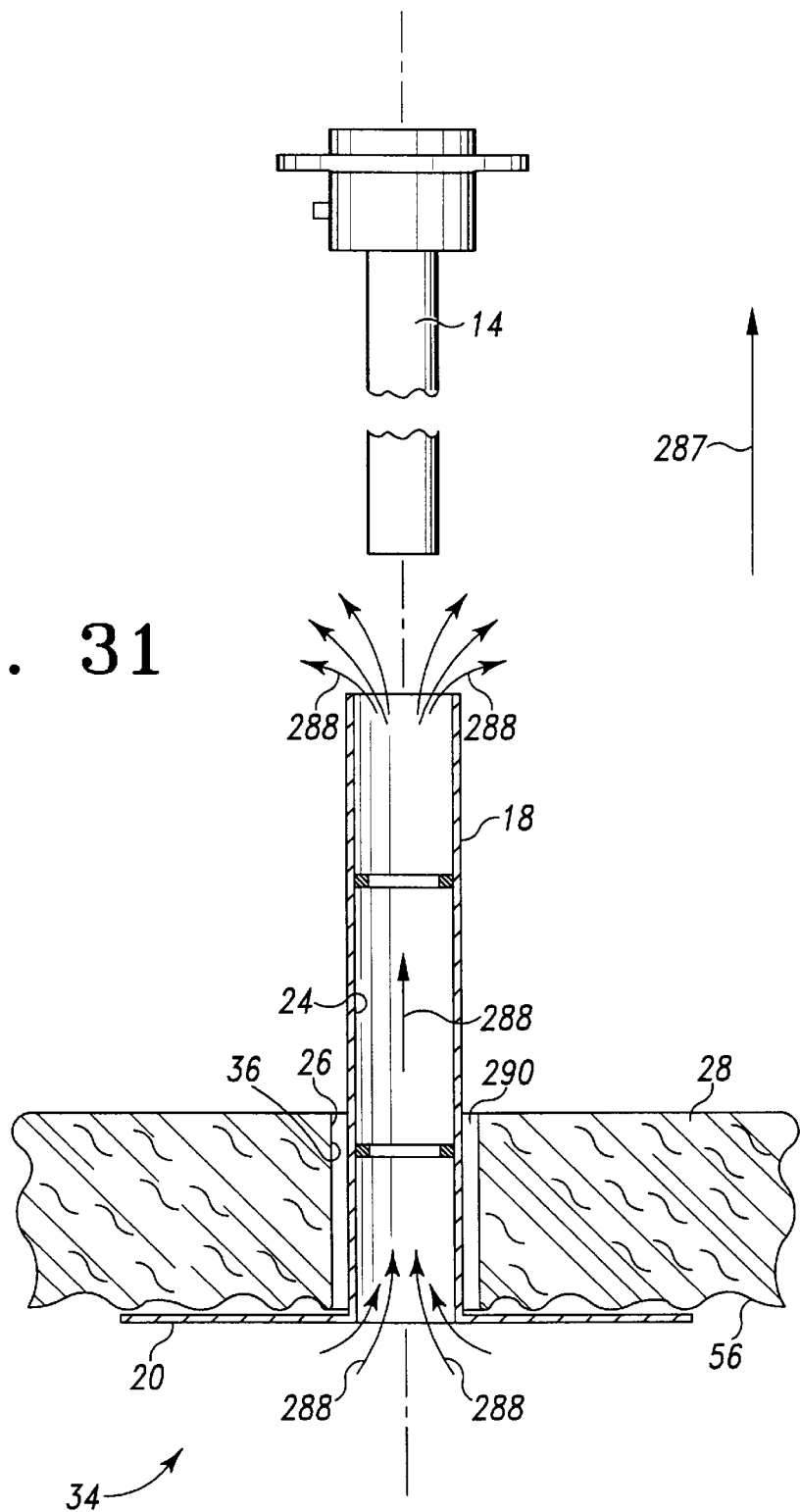
FIG. 31 is a view similar to FIG. 27, however the cannula is shown completely removed from the passageway of the sleeve.

As shown in FIG. 26, cannula 14 is positioned within passageway 24 of sleeve 18 such that a space 270 is defined between interior sleeve sidewall 266 and exterior cannula sidewall 268. In addition, a gasket 264 or bearing member is secured to interior sleeve sidewall 266 with an adhesive 272 such that gasket 264 extends into space 270 and contacts exterior cannula sidewall 268. Gasket 264, interior sleeve sidewall 266, and exterior cannula sidewall 268 form a seal or gas tight junction so as to prevent fluid communication between an area inside of body cavity 34 and an area outside of body cavity 34 through space 270. However, it should be appreciated that gasket 264 allows cannula 14 to slidably move relative to sleeve 18 in a direction indicated by arrow 274, and in a direction opposite to the direction indicated by arrow 274. In addition, cannula 14 is positionable relative to sleeve 18 between a first cannula position and a second cannula position. Cannula 14 is positioned within passageway 24 of sleeve 18 when cannula 14 is positioned at the first cannula position as shown in FIG. 27. Cannula 14 is completely removed from passageway 24 when cannula 14 is positioned at the second cannula position as shown in FIG. 31.

Figure 6:
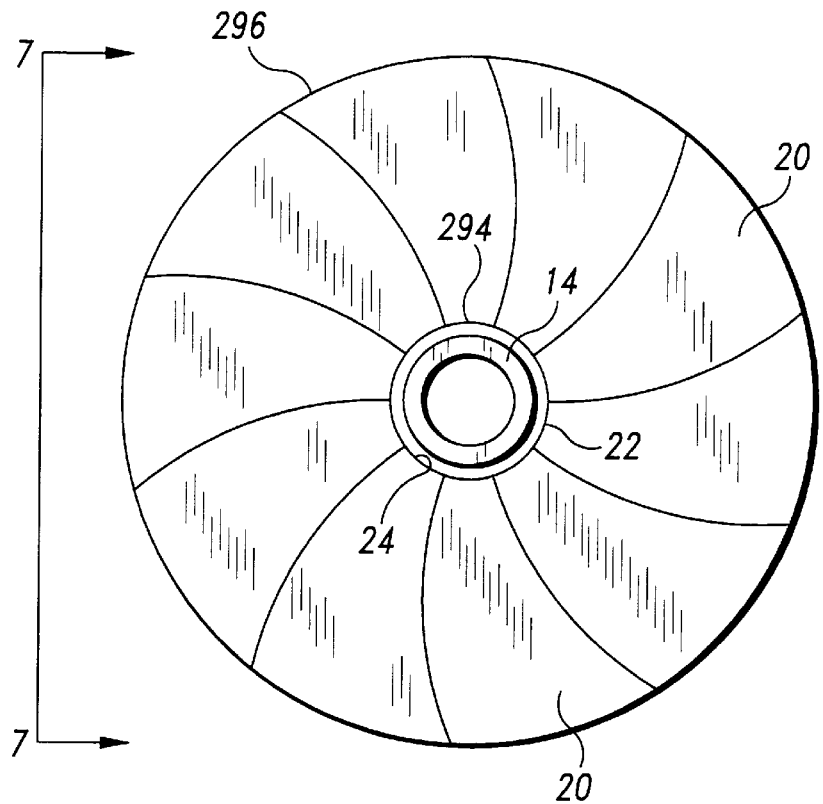
FIG. 6 is a view similar to FIG. 2, however the medical apparatus is shown reduced, and the sealing members are shown in the second orientation.
Figure 7:
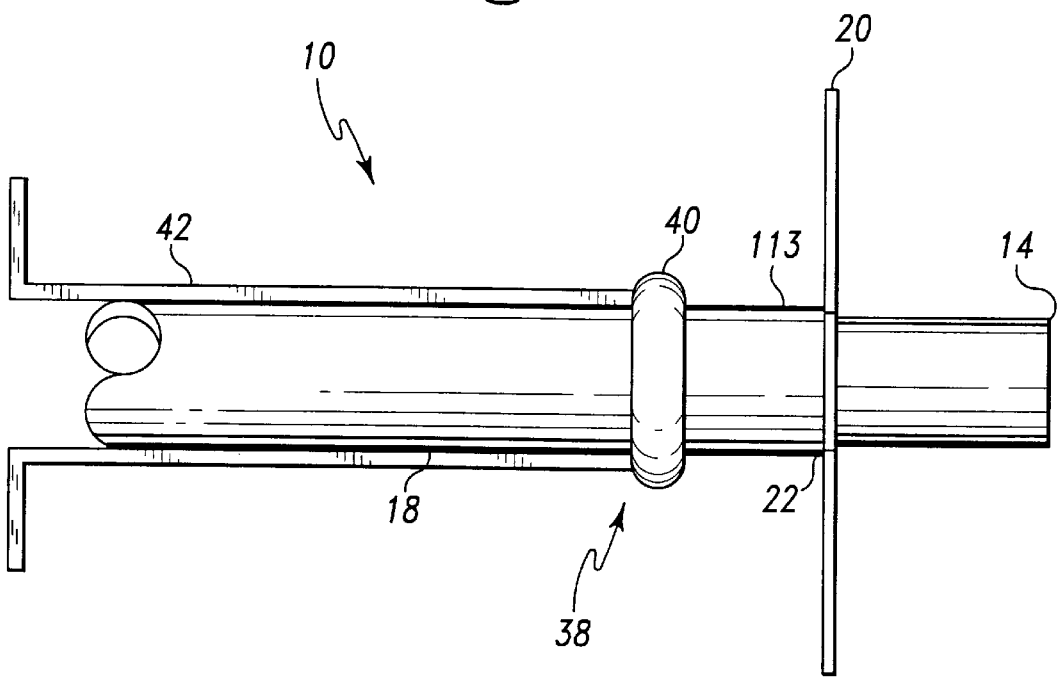
FIG. 7 is a fragmentary side elevational view of the medical apparatus taken along line 7—7 of FIG. 6.

Guide member 40 is slidably mounted onto sleeve 18 so it can be moved between a first position as shown in FIG. 4 and a second position as shown in FIG. 5. The double headed arrow 93 of FIG. 1 shows the direction of movement of guide member 40. Specifically, FIGS. 1–4 show guide member 40 placed in the first position, whereas FIGS. 5 and 7 show guide member 40 placed in the second position. As illustrated in FIGS. 1, 3, 5, and 7, the position of guide member 40 controls the movement of sealing members 20 between a first orientation and a second orientation. The sealing members 20 are positioned in the first orientation when the sealing members 20 are positioned in a substantially parallel relationship with passageway 24 of sleeve 18, as shown in FIGS. 1–4. When positioned in the first orientation, second end portions 296 of sealing members 20 cooperate to define an orifice 298 (see FIG. 2). The sealing members 20 are positioned in the second orientation when the sealing members 20 are positioned in a substantially orthogonal relationship with passageway 24 of sleeve 18 as shown in FIGS. 5–7. Moreover, as depicted in FIG. 6, when sealing members 20 are positioned in the second orientation they extend from the distal end 22 of sleeve 18 so as to overlap one another, thereby completely surrounding passageway 24 of sleeve 18.

Thus it should be appreciated that sleeve 18 and sealing members 20 are formed such that when no force is applied to sealing members 20 they spontaneously assume their second orientation (see FIGS. 5–7). Moreover, sealing members 20 are flexibly attached to distal end 22 such that when force is applied (i.e. the force applied by sliding guide member 40 over the sealing members 20) the sealing members 20 assume their first orientation (see FIGS. 1–4).

FIG. 6 shows sealing members 20 extending to form an annular flange. However, it should be appreciated that the present invention is not limited to the geometric shape formed by sealing members 20. For example, other geometric shapes are contemplated, such as square or oval shaped configurations. Moreover, a single sealing member extending from a distal end of a sleeve (or other medical device), or a number of non-overlapping or overlapping sealing members spaced around a distal end of a sleeve (or other medical device) are also contemplated. Furthermore, sealing members having perforations thereon which can be torn and separated prior to positioning in contact with the interior surface of a body cavity wall are also contemplated.

Sleeve 18 and guide member 40 can be made from any plastic material which is conventionally used in the medical device arts. Such material would be compatible with insertion into a body cavity. It should also be noted that the guide member used in the present invention can be manufactured to a size which only adds a minimal amount of bulk to the diameter of a trocar assembly. By doing so, trauma to the body cavity wall upon insertion of the medical apparatus of the present invention will be reduced.

Handles 42 can be made of any material having the appropriate beam strength to move guide member 40 from the first position to the second position.

When performing a medical procedure with medical apparatus 10, such as laparoscopic surgery, guide member 40 is placed into the first position (see FIGS. 1–4) so that sealing members are maintained in their first orientation. Trocar 16 of medical apparatus 10 is then placed in contact with, and advanced through, wall 28 of a body cavity 34 to create an opening 26 (i.e. the port site wound). Preferably, sleeve 18, cannula 14, and trocar 16 are simultaneously advanced through the opening 26 and into body cavity 34. It should be appreciated that tabs may be positioned on the sleeve 18 to prevent handles 42 and guide member 40 from being forced in the direction of arrow 94 (and therefore toward their second position (see FIGS. 5 and 7)) during the advancement of medical apparatus 10 through wall 28. It should also be appreciated that maintaining guide member 40 in its first position, and therefore sealing members 20 in their first orientation, facilitates the advancement of sleeve 18 through opening 26 and into body cavity 34.

Once distal end 22 of medical apparatus 10 enters into body cavity 34 through opening 26, handles 42 are moved away from opening 26 in the direction of arrow 94 (see FIG. 1) so as to slide guide member 40 to the second position (see FIGS. 5 and 7), thereby allowing sealing members 20 to assume their second orientation. Once sealing members 20 have assumed their second orientation they are positioned to contact the interior surface 56 of the body cavity wall 28 (see FIG. 5). Once sealing members 20 are in their second orientation and positioned in contact with the interior surface 56 of the body cavity wall 28 they surround a space 36 defined between the opening 26 and the sleeve 18. Positioning sealing members 20 in the above described manner prevents fluid communication between an area inside of body cavity 34 and an area outside of body cavity 34 through space 36.

In addition, it should be understood that a non-perforating ridge (not shown) extending from the surface of the sealing members 20 and contacting interior surface 56 of body cavity wall 28 is also contemplated. Such a ridge will also contact interior surface 56 of body cavity wall 28 and assist in preventing fluid communication between the area inside of the body cavity 34 and the area outside of the body cavity through space 36 defined between opening 26 and sleeve 18. The aforementioned ridge will also keep sealing members 20 stationary relative to interior surface 56 of body cavity 34 during manipulations of cannula 14.

Referring now to FIGS. 27–31, once the sealing members 20 are positioned as described above, trocar 16 is moved to the second trocar position (i.e. trocar 16 is completely removed from cannula 14 (see FIG. 27)). An insufflation gas, such as $CO_2$, is then pumped through valve 256, valve assembly 254, lumen 19 of cannula 14, and into body cavity 34. A shaft 262 of a medical instrument 258 is inserted through lumen 19 of cannula 14 such that a set of jaws 260 attached to an end 263 of shaft 262 is positioned within body cavity 34. It should be understood that in order to successfully complete the medical procedure jaws 260 will be positioned at different locations within body cavity 34 by advancing or withdrawing shaft 262 through lumen 19 of cannula 14. For example, jaws 260 may have to be positioned at a certain location within body cavity 34 in order to grasp a tumor (not shown).

Figure 28:
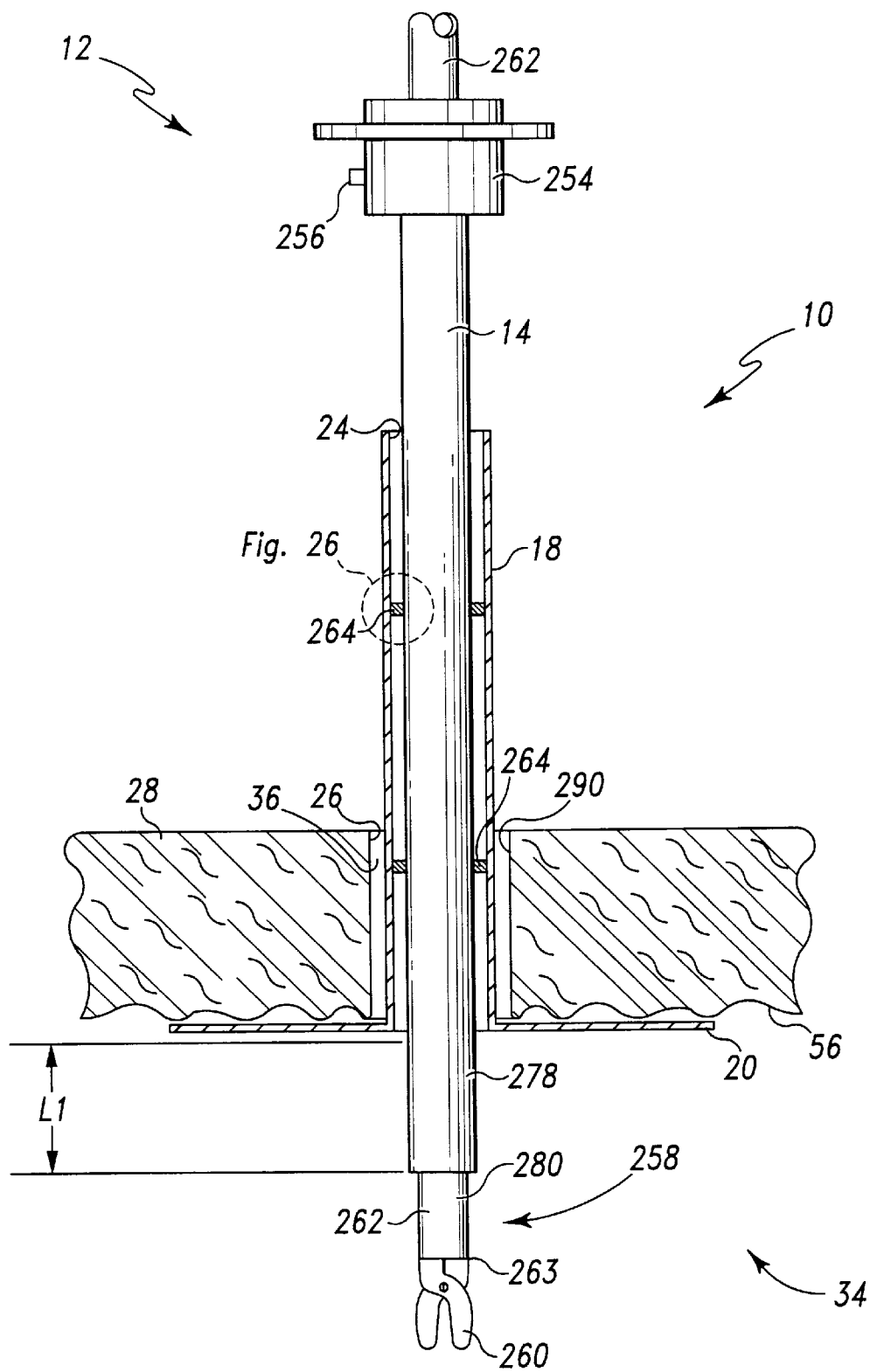
FIG. 28 is a view similar to FIG. 27, however a medical instrument is shown inserted through the lumen of the cannula and the cannula is advanced to a length $L_1$ into the body cavity.
Figure 29:
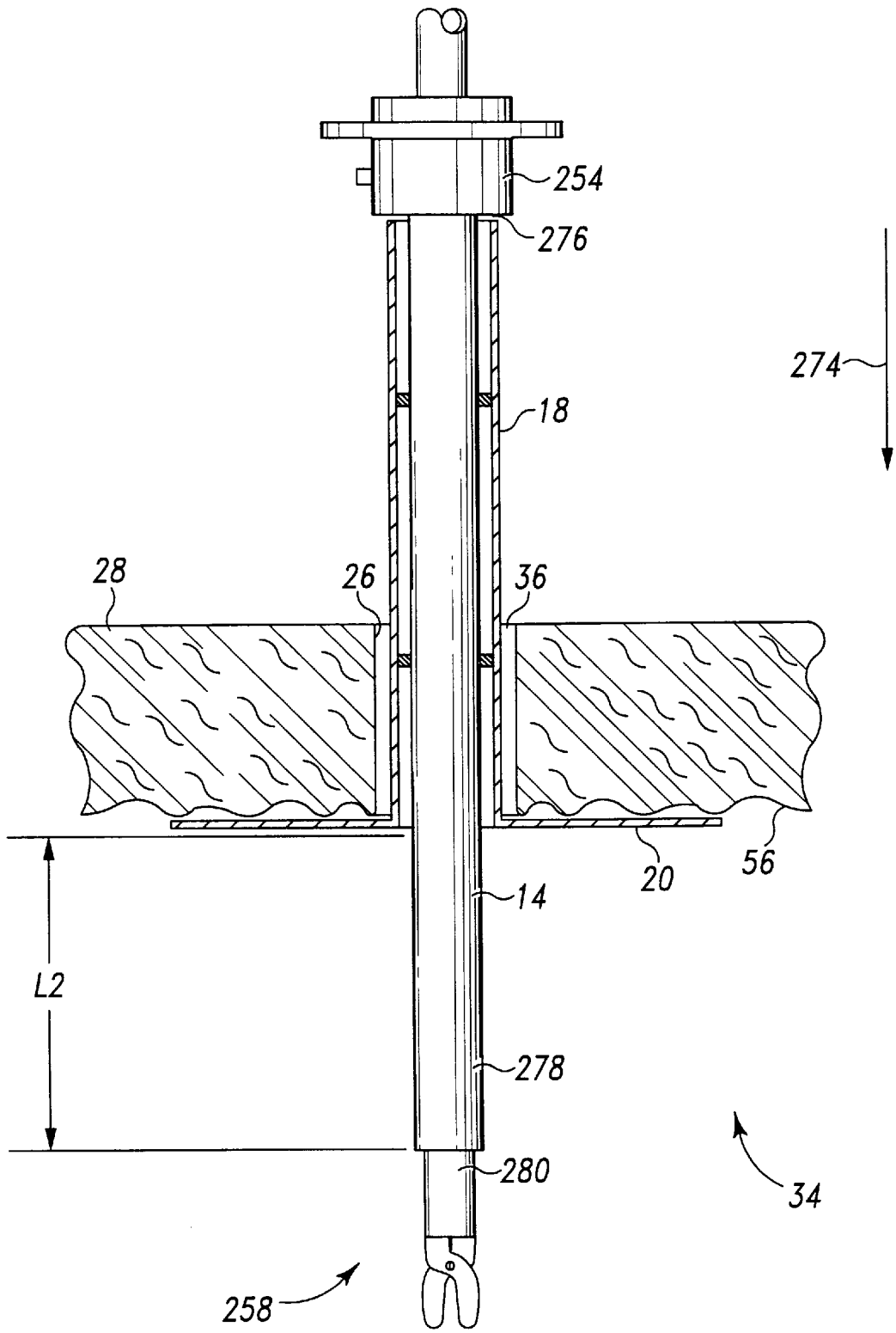
FIG. 29 is a view similar to FIG. 28, however the cannula is shown advanced to a length $L_2$ into the body cavity.
Figure 30:
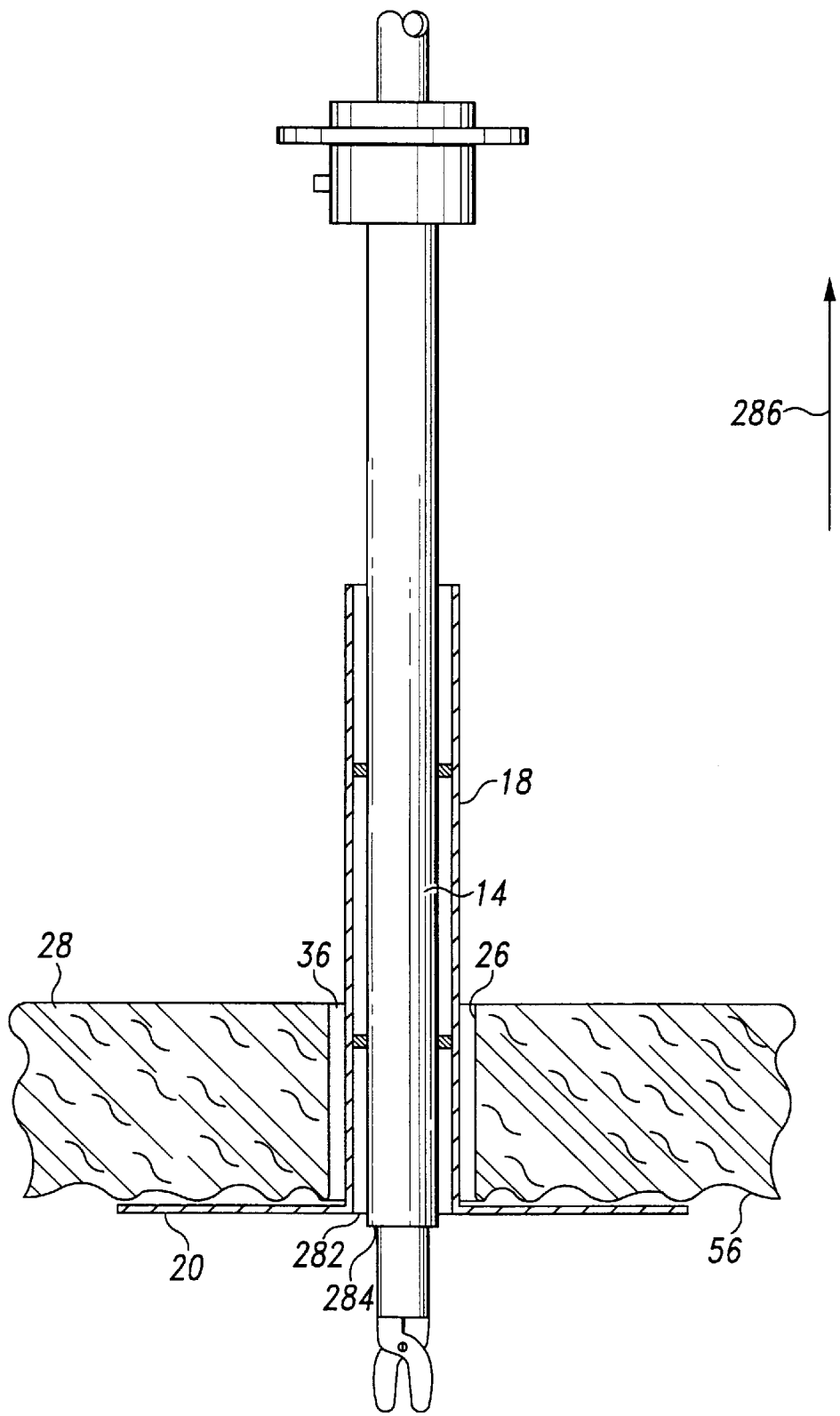
FIG. 30 is a view similar to FIG. 29, however the cannula is shown withdrawn from the body cavity such that an end of the cannula is adjacent to an end of the sleeve.

As previously discussed, when cannula 14 is positioned at the first cannula position (i.e. cannula 14 is positioned within passageway 24 of sleeve 18), cannula 14 is slidably mounted within passageway 24 of sleeve 18. Therefore, in addition to adjusting the position of shaft 262 relative to cannula 14, the position of cannula 14 can be adjusted relative to sleeve 18 to position jaws 260 within body cavity 34. For example, as shown in FIG. 28, cannula 14 can be positioned relative to sleeve 18 such that a length $L_1$ of cannula 14 extends into body cavity 34. As shown in FIG. 29, cannula 14 can also be moved in an axial direction relative to sleeve 18 as indicated by arrow 274 such that valve assembly 254 contacts an end 276 of sleeve 18. At this position, the cannula 14 extends a length $L_2$ into body cavity 34. Moreover, as shown in FIG. 30, cannula 14 can be moved in an axial direction relative to sleeve 18 as indicated by arrow 286 such that an end 284 of cannula 14 is positioned substantially adjacent to an end 282 of sleeve 18.

Being able to adjust the position of jaws 260 (or the distal end of any medical instrument positioned within lumen 19 of cannula 14) by moving cannula 14 relative to sleeve 18 in the above described manner is an important aspect of the present invention since it provides the surgeon with added flexibility in moving jaws 260 to the appropriate position within body cavity 34 to successfully complete the medical procedure.

In addition, it should be appreciated that cannula 14 can be moved relative to sleeve 18 in the above described manner while maintaining the contact between sealing members 20 and the interior surface 56 of body cavity wall 28. Maintaining this contact is another important aspect of the present invention since it ensures that opening 26 is protected against tumor cell implantation or contamination with an infectious agent during the above described movement of cannula 14 relative to sleeve 18. This is in contrast to the situation where a cannula cannot move in relation to the sealing members in the above described manner (i.e. the cannula and the sealing members move as a single unit). In this situation, advancing the cannula further into body cavity 34 will also advance the sealing members further into body cavity 34, thus causing the sealing members to disengage interior surface 56 of body cavity wall 28. Disengaging the sealing members from interior surface 56 allows fluid communication between an area inside of body cavity 34 and an area outside of body cavity 34 through space 36 (e.g. gas or body fluids my be advanced from an area inside body cavity 34 to an area outside of body cavity 34 through space 36). This fluid communication may result in tumor cells being implanted in a sidewall 290 (see FIGS. 28 and 32) of opening 26. The fluid communication can also result in sidewall 290 being contaminated with an infectious agent.

After completing the medical procedure utilizing medical apparatus 10, medical instrument 258 is withdrawn from lumen 19 of cannula 14. As shown in FIG. 31, cannula 14 is then moved relative to sleeve 18 in the axial direction indicated by arrow 287 until cannula 14 is positioned at the second cannula position (i.e. cannula 14 is completely withdrawn from passageway 24 of sleeve 18). Removing cannula 14 from sleeve 18 allows the insufflation gas to rapidly escape body cavity 34 through passageway 24 of sleeve 18 as shown by arrows 288. Having sleeve 18 positioned within opening 26 and sealing members 20 in contact with interior surface 56 of the body cavity wall 28 protects sidewall 290 of opening 26 from coming into contact with aerosolized tumor cells or infectious agents carried by the escaping insufflation gas.

Once substantially all the insufflation gas has escaped from body cavity 34 (i.e. body cavity 34 has been desufflated) handles 42 are moved toward opening 26 in a direction opposite to arrow 94 so as to slide guide member 40 to the first position (see FIGS. 1–4). The movement of guide member 40 to the first position forces sealing members 20 to assume their first orientation (see FIGS. 1–4), thereby facilitating the removal of sleeve 18 from opening 26. In addition, it should be appreciated that positioning sealing members 20 in the first orientation prevents any infectious or cancerous cells adhered to surface 11 (see FIG. 5) of sealing members 20 from coming into contact with sidewall 290 as sleeve 18 is withdrawn from opening 26.

Thus, it should be understood that sleeve 18 including sealing members 20 are the last components to be removed from body cavity 34 by the surgeon (not shown). Removing sleeve 18 including sealing members 20 last ensures that opening 26 (i.e. the port site wound) remains protected against tumor cell implantation or contamination with an infectious agent until completion of the medical procedure.

Figure 32:
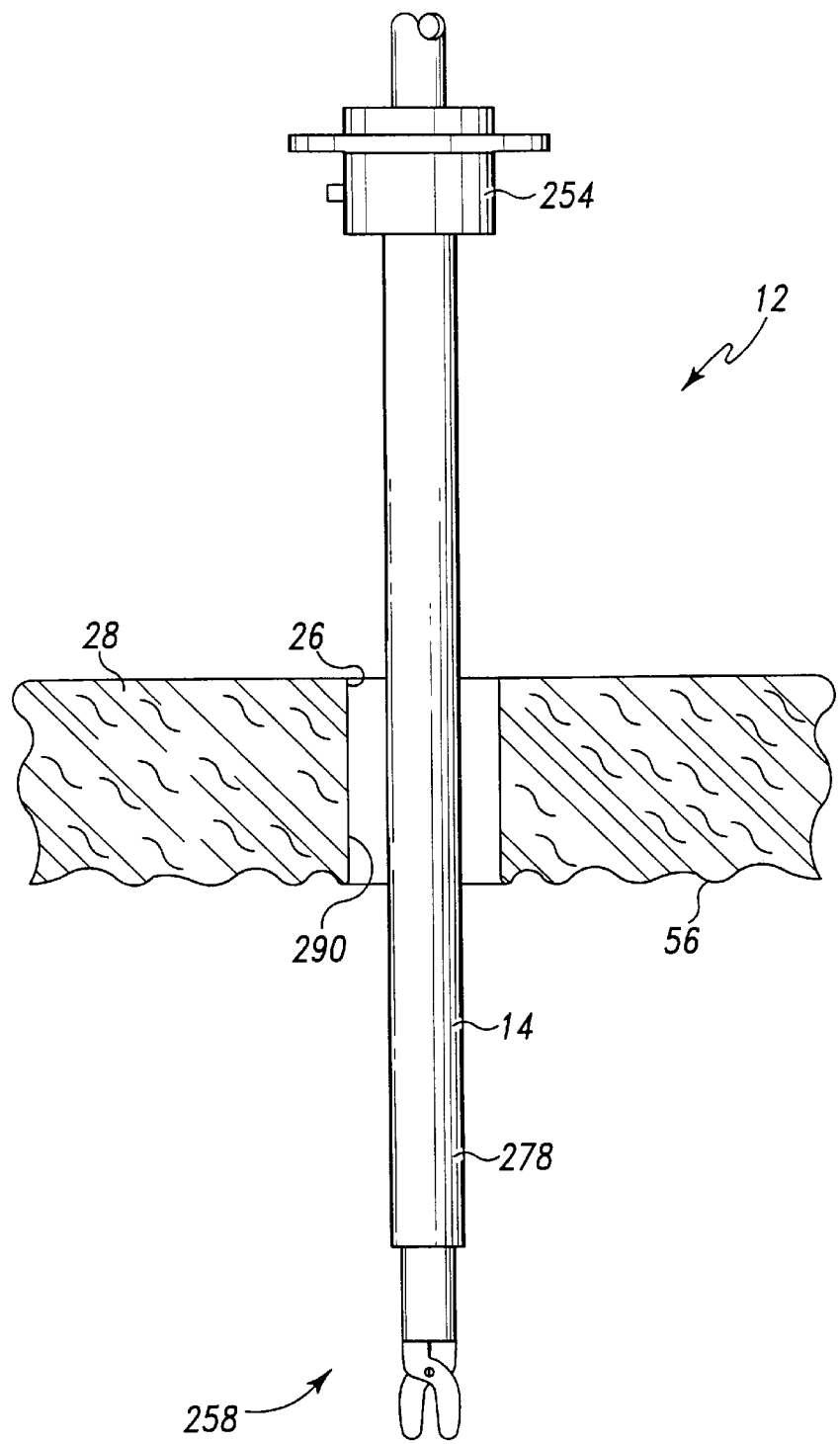
FIG. 32 is a view similar to FIG. 29, however the medical apparatus is shown not equipped with the sleeve.

It should be appreciated that the probability of contaminating opening 26 with infectious or cancerous cells during a medical procedure is much greater when trocar assembly 12 is not equipped with sleeve 18. Specifically, when trocar assembly 12 is not equipped with sleeve 18 as shown in FIG. 32, an exterior surface 278 of cannula 14 can come into direct contact with sidewall 290 of opening 26. This direct contact can result in the contamination of opening 26 since tumor cells and infectious agents have been shown to become adhered to exterior surface 278 during a medical procedure. Therefore, as cannula 14 is moved in and out of opening 26 in the absence of sleeve 18, tumor cells and/or infectious agents adhered to exterior surface 278 are brought into direct contact with sidewall 290 of opening 26. The aforementioned direct contact can result in tumor cells being implanted into sidewall 290, or sidewall 290 being contaminated with an infectious agent. However, having trocar assembly 12 equipped with sleeve 18, as shown in FIG. 28, provides a barrier between sidewall 290 and cannula 14 which prevents tumor cells from coming into contact with, and thus becoming implanted into, sidewall 290. In addition, the barrier provided by sleeve 18 prevents sidewall 290 from becoming contaminated with an infectious agent.

Figure 33:
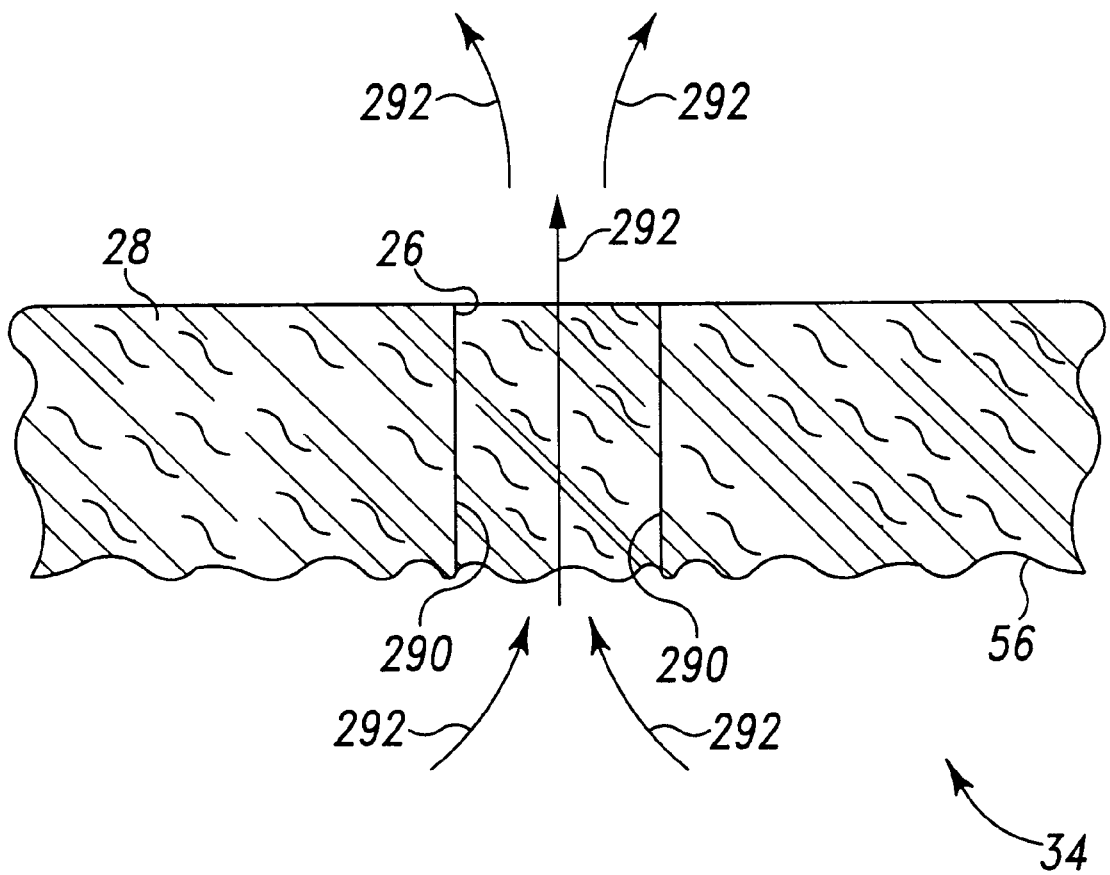
FIG. 33 is a cross-sectional view of the body cavity wall after removing the medical apparatus shown in FIG. 32 therefrom.

In addition, when trocar assembly 12 is not equipped with sleeve 18 and cannula 14 is removed from opening 26 at the end of the medical procedure, sidewall 290 of opening 26 comes into direct contact with the insufflation gas as it escapes from body cavity 34 in the direction indicated by arrows 292 as shown in FIG. 33. Therefore, aerosolized tumor cells may become implanted into sidewall 290 as a result of the contact with the escaping insufflation gas. In addition, sidewall 290 can become contaminated with infectious agents as a result of coming into contact with the escaping insufflation gas. However, as previously discussed, having trocar assembly 12 equipped with sleeve 18 provides a barrier between sidewall 290 and the escaping insufflation gas upon removal of cannula 14 as shown in FIG. 31. The barrier provided by sleeve 18 including sealing members 20 prevent sidewall 290 from coming into contact with aerosolized tumor cells or infectious agents carried by the escaping insufflation gas.

SECOND EMBODIMENT OF THE INVENTION

Figure 19:
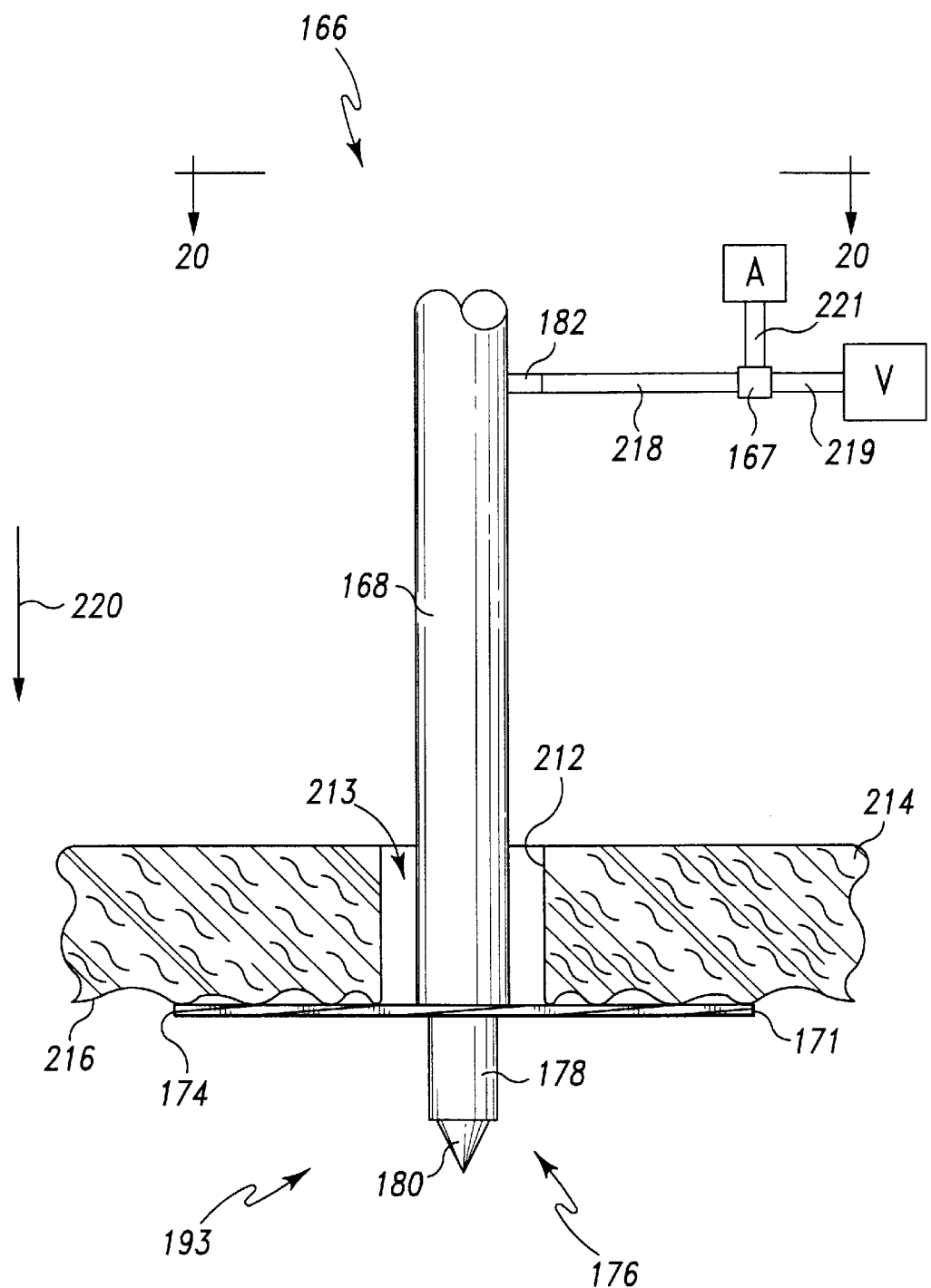
FIG. 19 is a fragmentary side elevational view of a medical apparatus similar to the one shown in FIG. 1, but with a vacuum source and an air supply of the medical apparatus being shown in fluid communication with an actuator of the medical apparatus.

Now referring to FIG. 19, there is shown a medical apparatus 166 similar to the medical apparatus 10 shown in FIG. 1. Medical apparatus 166 is shown advanced through an opening 212 in a wall 214 of a body cavity 193. Medical apparatus 166 includes a trocar assembly 176, a sleeve 168, a vacuum source V, and an air supply A.

Vacuum source V can be manually operated or power driven. Examples of vacuum sources which can be used in the present invention include a wall suction apparatus, aspirator pumps, syringes, or any other convenient operating vacuum source. Similarly, air supply A can be manually operated or power driven. Examples of air supplies which can be used in the present invention include an air compressor, a syringe, or any other convenient operating air supply.

Figure 20:
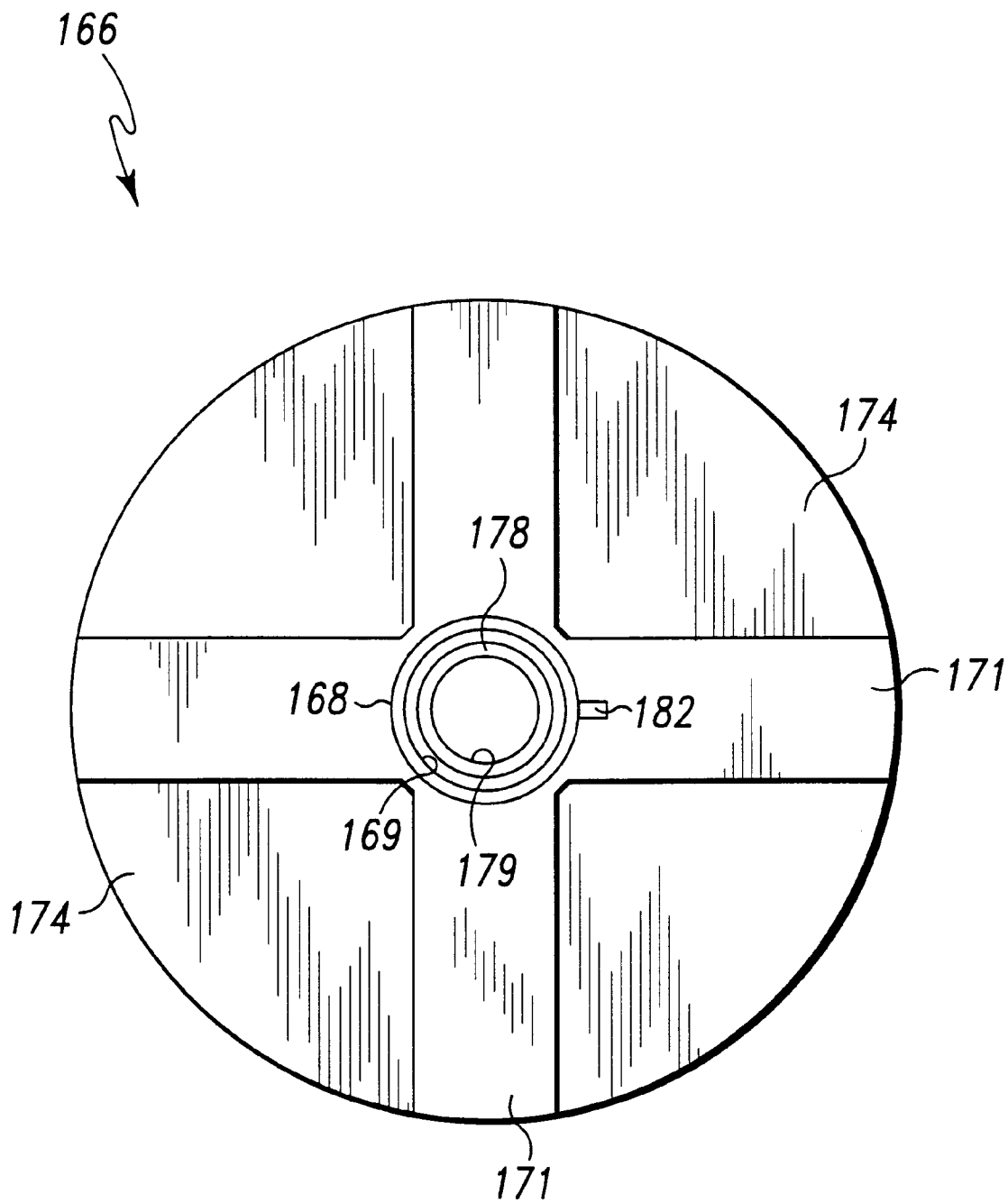
FIG. 20 is an enlarged elevational view of the medical apparatus taken along line 20—20 of FIG. 19, with the body cavity wall, trocar and hose removed for clarity of description.
Figure 21:
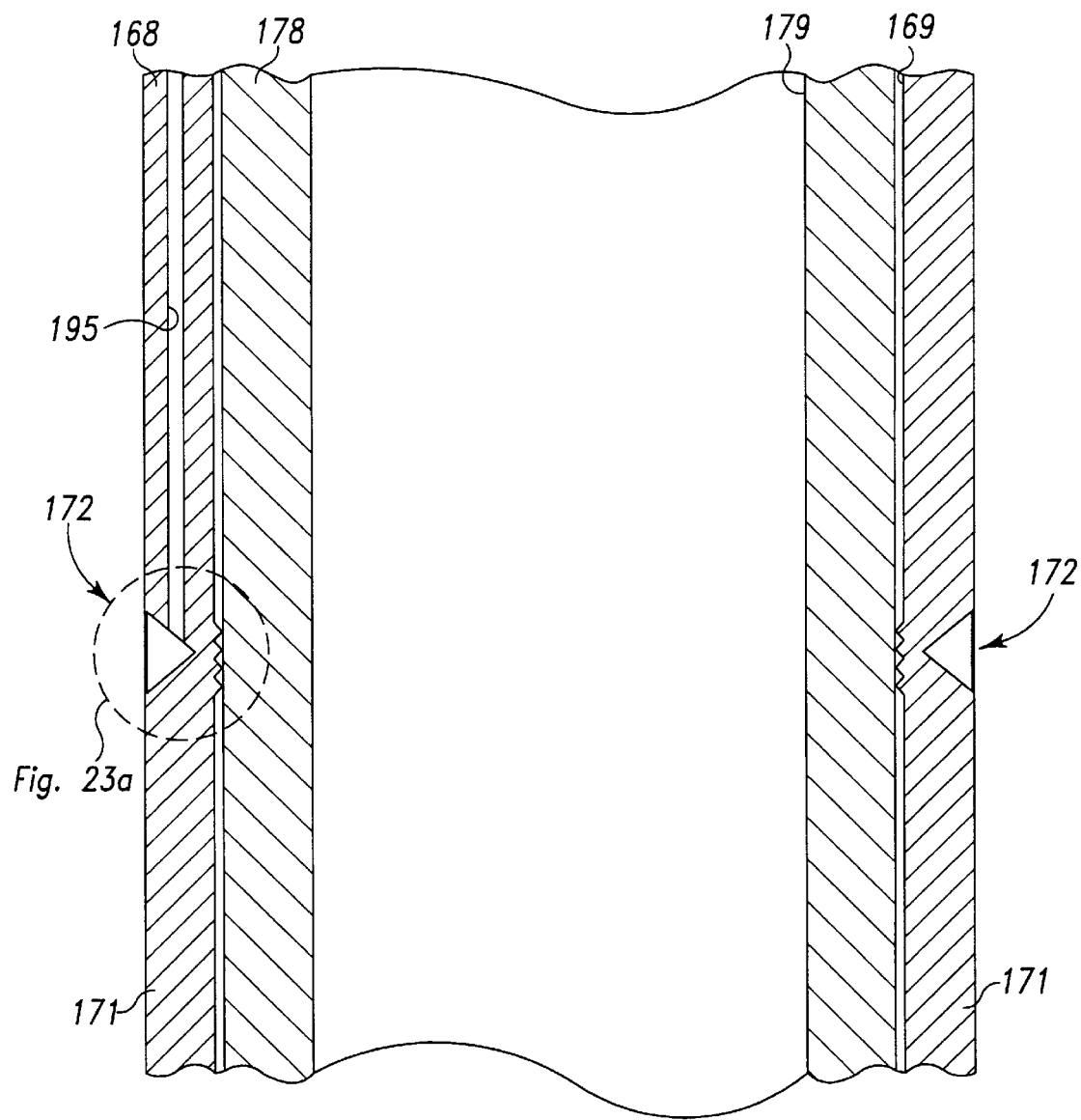
FIG. 21 is an enlarged fragmentary cross sectional view of the medical apparatus of FIG. 19, with the sealing members shown in the first orientation.
Figure 22:
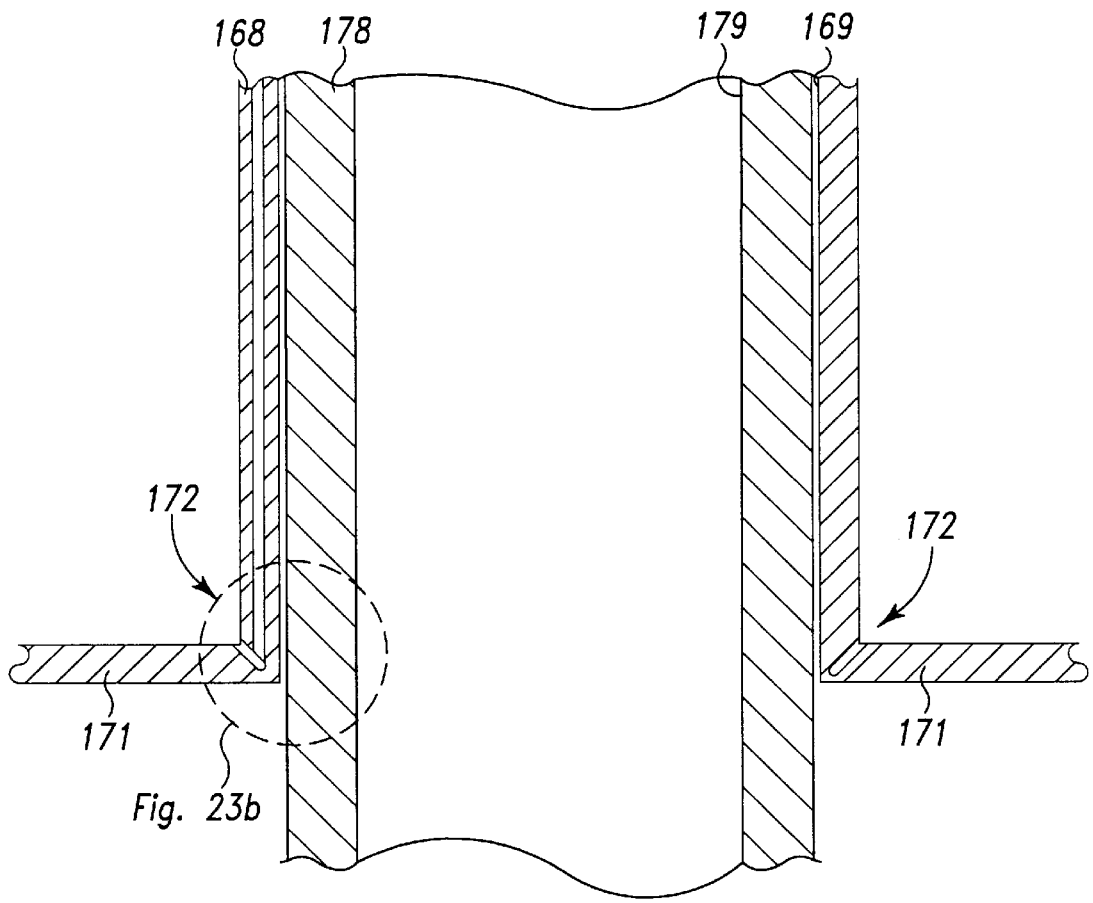
FIG. 22 is a view similar to FIG. 21 but showing the sealing members positioned in the second orientation.

As shown in FIGS. 20, 21, and 22, sleeve 168 has a number of sealing members 171 extending therefrom and a passageway 169 extending therethrough. Sleeve 168 also has a channel 195 defined therein (see FIGS. 21 and 22). Channel 195 is in fluid communication with a valve 182 (see FIG. 19) attached to sleeve 168. Valve 182 can be any of a number of well known valves capable of maintaining and then releasing a vacuum, as long as the size of the valve does not interfere with the operation of the medical apparatus into which sleeve 168 is incorporated. For example, valve 182 can be a trumpet valve or a conventional two or three way stop cock valve. It should be understood that channel 195 is selectively placed in fluid communication with vacuum source V via valve 182, hose 218, and a hose 219 by manipulating a valve 167 (see FIG. 19). In a similar fashion, channel 195 is selectively placed in fluid communication with air supply A via valve 182, hose 218, and a hose 221 by manipulating valve 167. Valve 167 can be any valve (e.g. a three way stop cock valve) capable of directing a flow of air.

As shown in FIG. 20, adjacent sealing members 171 have a web 174 connected therebetween. Sealing members 171 are movable relative to sleeve 168 between a first orientation in which sealing members 168 are positioned in a substantially parallel relationship with passageway 169 (see FIG. 21), and a second orientation in which sealing members 171 are positioned substantially perpendicular to passageway 169 (see FIG. 22). It should be understood that various sized sealing members 171 and webs 174 are contemplated to facilitate the movement of the sealing members 171 between the first and second orientation.

Referring back to FIG. 19, trocar assembly 176 includes a cannula 178 and a trocar 180. Cannula 178 has a lumen 179 (see FIG. 20) defined therein, and trocar 180 is positioned within lumen 179. However, it should be understood that trocar 180 is completely removable from lumen 179 (note that FIGS. 20, 21 and 22 show trocar 180 completely removed from lumen 179). Trocar assembly 176 is positioned within passageway 169 of sleeve 168. It should be appreciated that cannula 178 can be moved relative to sleeve 168 while still maintaining the contact between sealing members 171 and interior surface 216 of body cavity 193

(see FIG. 19), and between webs 174 and interior surface 216 of body cavity 193. It should also be appreciated that cannula 178 is completely removable from passageway 169 of sleeve 168. Being able to (1) move cannula 178 relative to sleeve 168 and (2) completely remove cannula 178 from sleeve 168 has all the same advantages as described above in reference to sleeve 18.

As shown in FIGS. 21, 22, 23a, and 23b sleeve 168 includes an actuator 172 secured to sealing members 171. As shown more clearly in FIG. 23a, actuator 172 includes a flexible cover 190, a wall segment 198, and a wall segment 200. Wall segment 198 is attached to sealing member 171 and wall segment 200 is attached to sleeve 168. In addition, wall segment 198 and wall segment 200 are connected to each other so as to form a "V" shaped structure 209 (see FIG. 23a). One edge of flexible cover 190 is attached to a portion of wall segment 200. The edge of flexible cover 190 opposite to the edge attached to wall segment 200 is attached to a portion of wall segment 198, such that wall segment 198, flexible cover 190, and wall segment 200 define a ring-shaped chamber 192 which completely surrounds cannula 178. Actuator 172 also includes a flexible hinge 208 which connects sealing member 171 to sleeve 168. Flexible hinge 208 includes a corrugated area 197 having a number of corrugations 199 formed thereon. It should be appreciated that the various components of actuator 172 are made from any fluid impervious plastic or rubber material which is conventionally used in the medical device arts and is compatible with insertion into body cavity 193.

Figure 23A:
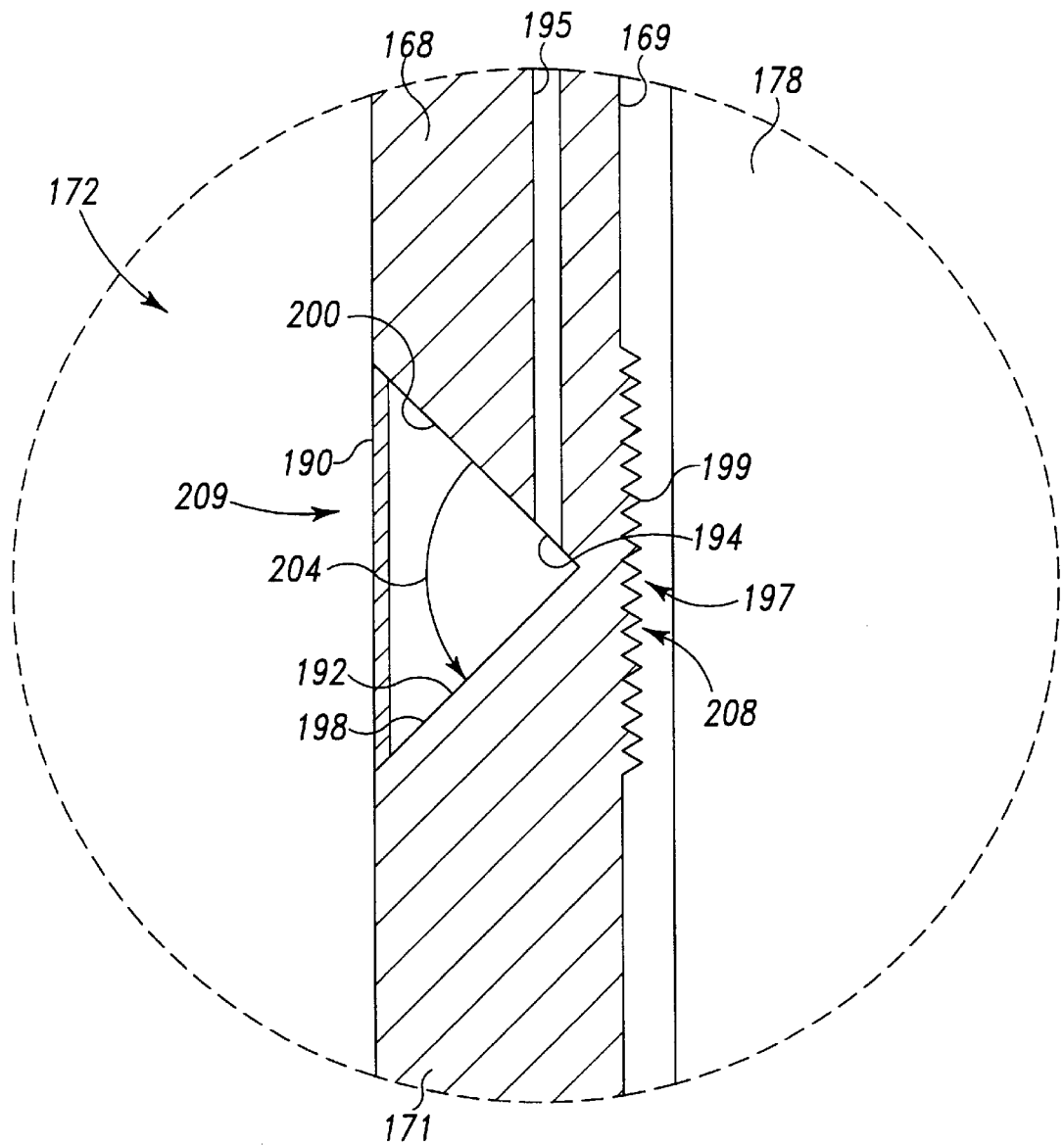
FIG. 23a is an enlarged view of a portion of FIG. 21 which is encircled and indicated as FIG. 23a, which shows the actuator in greater detail.
Figure 23B:
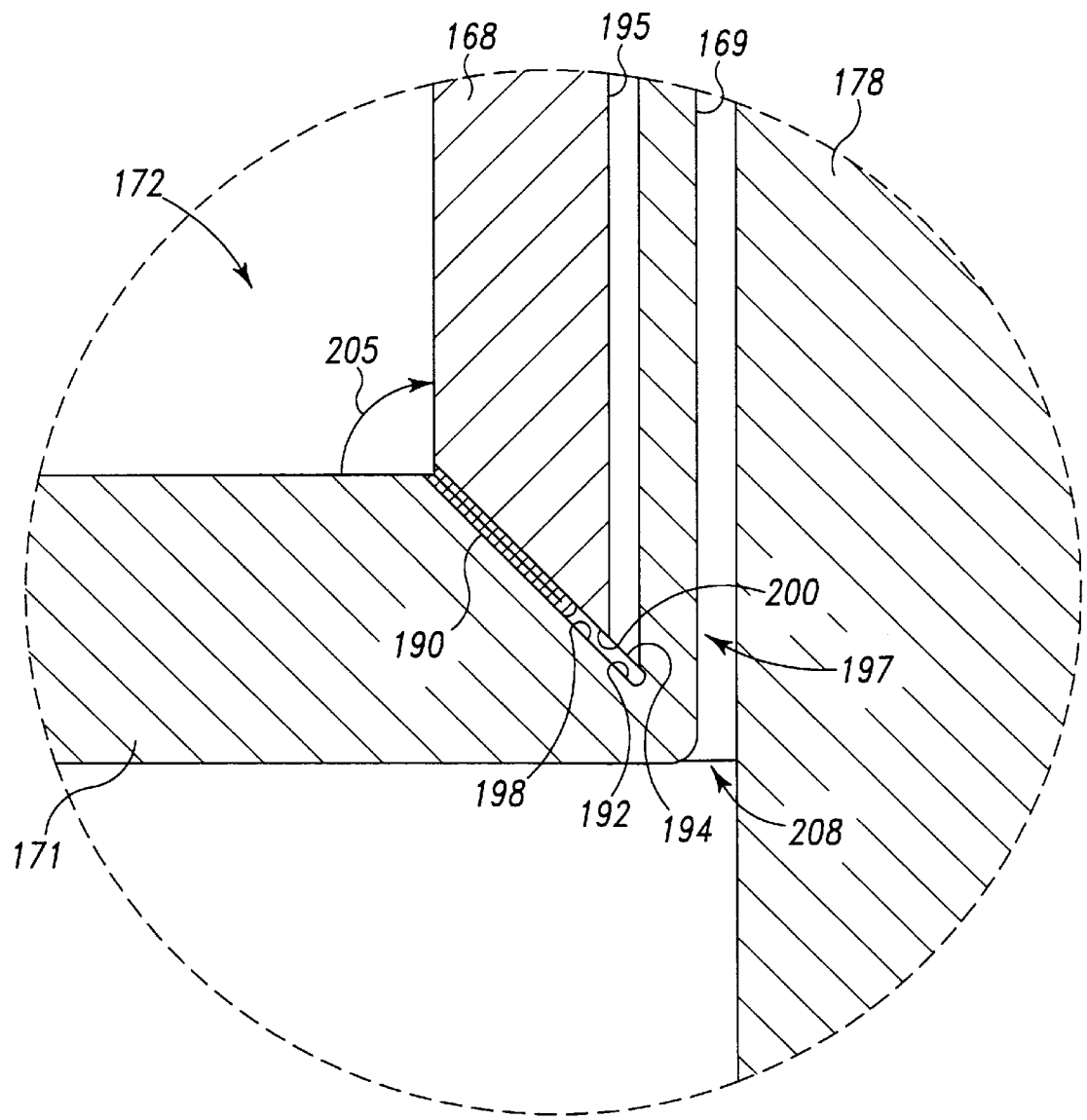
FIG. 23b is an enlarged view of a portion of FIG. 22 which is encircled and indicated as FIG. 23b, which shows the flexible cover folded and positioned within the chamber of the actuator.

As shown in FIGS. 23a and 23b, wall segment 200 has a port 194 defined therethrough. Port 194 is in fluid communication with chamber 192. Port 194 is also in fluid communication with channel 195. Thus it should be appreciated that chamber 192 can be selectively placed in fluid communication with vacuum source V or air supply A via port 194 so as to evacuate air from or advance air into chamber 192. It should also be appreciated that wall segment 200 can have several ports substantially identical to port 194 defined therein, and sleeve 168 can have several channels substantially identical to 195 defined therein, so that chamber 192 can be placed in fluid communication with air supply A or vacuum source V utilizing a several ports and channels.

When performing a medical procedure with medical apparatus 166, such as laparoscopic surgery, valve 167 (see FIG. 19) is positioned such that chamber 192 is in fluid communication with air supply A. Air (other fluids, such as $CO_2$, are also contemplated) is then advanced into chamber 192 by air supply A through a fluid path defined by hose 221, valve 167, hose 218, valve 182, and channel 195.

Advancing air in the above described manner inflates chamber 192. As shown in FIG. 23a, once chamber 192 is inflated, the pressure of the air contained therein urges wall segment 198 away from wall segment 200 in a direction indicated by arrow 204. Urging wall segment 198 in the above described manner forces sealing member 171 to be positioned in the first orientation.

Once sealing members 171 are in the first orientation, trocar 180 is positioned in contact with wall 214 of body cavity 193. Trocar 180 is advanced through wall 214 in a direction indicated by arrow 220 (see FIG. 19) to create opening 212. It should be appreciated that having sealing members 171 positioned in the first orientation facilitates advancement of sleeve 168 through opening 212. In addition, it should be appreciated that preferably, sleeve 168, cannula 178, and trocar 180 are simultaneously advanced through opening 212 and into body cavity 193.

Once sealing members 171 are completely within body cavity 193 valve 167 (see FIG. 19) is positioned such that chamber 192 is in fluid communication with vacuum supply V. Air is then withdrawn from chamber 192 by vacuum supply V through a fluid path defined by hose 219, valve 167, hose 218, valve 182, (see FIG. 19) and channel 195 (see FIG. 23a). Withdrawing air in the above described manner creates a vacuum in chamber 192. As shown in FIG. 23b, the vacuum created in chamber 192 forces flexible cover 190 to collapse into chamber 192. The collapse of flexible cover 190 into chamber 192 in the above described manner causes wall segment 198 to move toward wall segment 200 in a direction indicated by arrow 205. Movement of wall segment 198 toward wall segment 200 forces sealing member 171 to bend at flexible hinge 208 and move in the direction indicated by arrow 205. Bending sealing member 171 at flexible hinge 208 causes corrugations 199 (see FIG. 23a) to flatten out (see FIG. 23b) thereby enhancing the flexibility of sealing member 171 at flexible hinge 208. Sealing member 171 continues to move in the direction indicated by arrow 205 until chamber 192 is substantially completely collapsed, and flexible cover 190 is folded within chamber 192 thereby positioning sealing member 171 at the second orientation as shown in FIG. 22.

Therefore, it should be understood that withdrawing air from chamber 192 in the above described manner causes sealing members 171 to be positioned at the second orientation as shown in FIG. 22, and advancing air into chamber 192 in the previously described manner causes sealing members 171 to be positioned at the first orientation as shown in FIG. 21. It should also be understood that since the webs 174 are attached to sealing members 171, webs 174 move with sealing members 171 between the first and second orientation. In addition, it should be appreciated that each web 174 allows sealing members 174 to move relative to one another, which facilitates the movement of sealing members 171 between the first orientation and the second orientation.

As shown in FIG. 19, once sealing members 171 have assumed the second orientation they are positioned in contact with interior surface 216 of body cavity 193. Each web 174 is also positioned in contact with interior surface 216. Positioning sealing members 171 and each web 174 in contact with interior surface 216 prevents fluid communication between an area inside of body cavity 193 and an area outside of body cavity 193 through a space 213 (see FIG. 19) defined between opening 212 and sleeve 168.

After completion of the medical procedure, all contaminated instruments (not shown), specimens (not shown), and the cannula 178 are withdrawn from the body cavity through passageway 169 of sleeve 168. The body cavity is then desufflated as the insufflation gas exits the body cavity through passageway 169. Air is then advanced into chamber 192 in the same manner as described above, thereby returning each sealing member 171 to the first orientation (see FIG. 21). (Note that returning sealing member 171 to the first orientation causes corrugations 199 to reform as shown in FIG. 23a). Sleeve 168 is then withdrawn from opening 212 (see FIG. 19) in wall 214 of body cavity 193. Thus, it should be understood that sleeve 168 and sealing members 171 are the last components to be removed from body cavity 193 by the surgeon. Removing sleeve 168 and sealing members 171 last ensures that opening 212 (i.e. the port site wound) remains protected against tumor cell implantation or contamination with an infectious agent until completion of the medical procedure.

THIRD EMBODIMENT OF THE INVENTION

Figure 8:
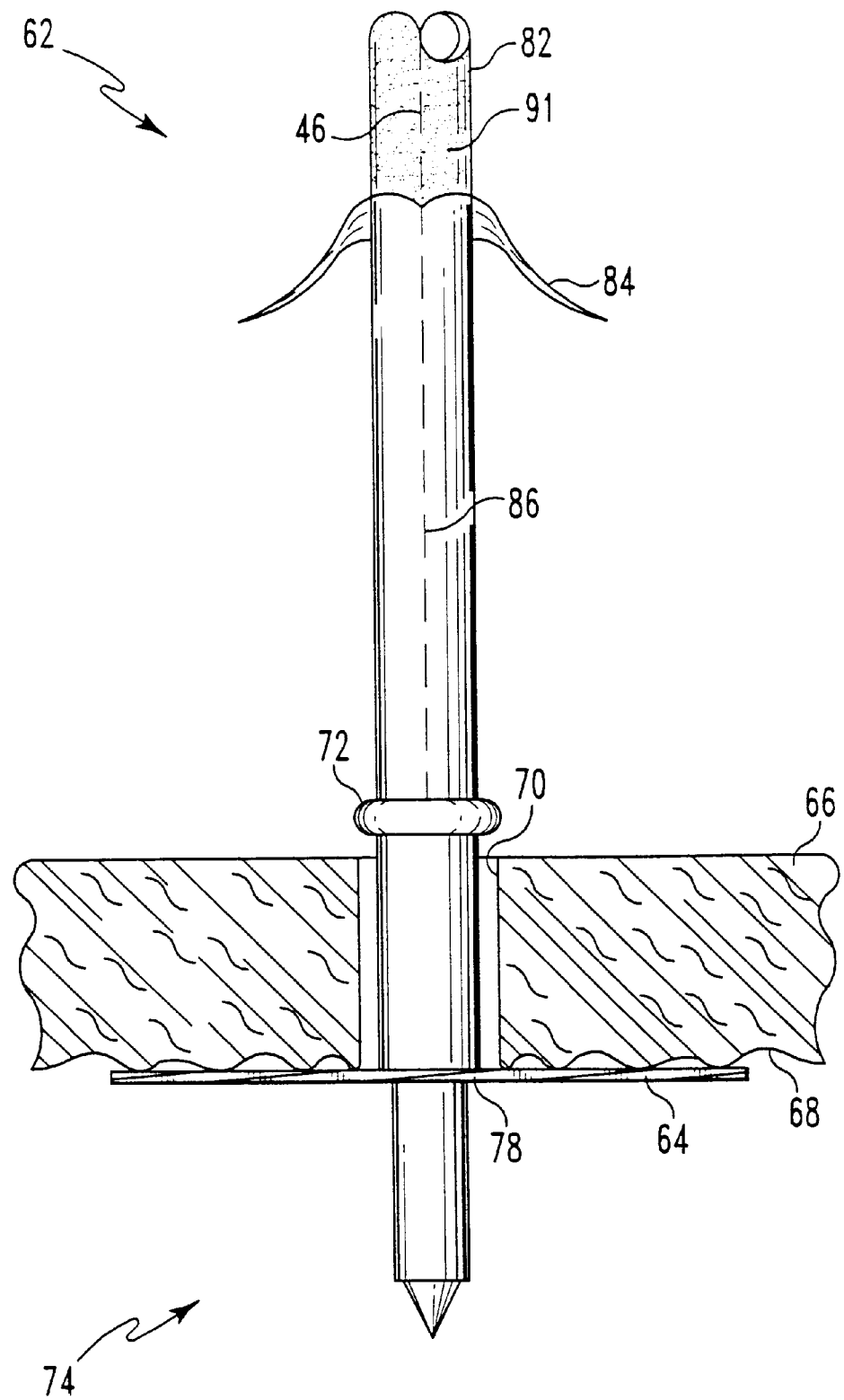
FIG. 8 is a fragmentary side elevational view of a medical apparatus similar to the one shown in FIG. 1, but this medical apparatus includes a strippable liner thereon (the handles are shown removed for clarity of description)

Now referring to FIG. 8, there is shown a medical apparatus 62 similar to the medical apparatus 10 shown in FIG. 1. Medical apparatus 62 is shown advanced through an opening 70 in a wall 66 of a body cavity 74. The medical apparatus 62 includes a sleeve 82 having a plurality of perforations 86 defined in its proximal end portion and an adhesive material disposed on its outer surface 91. The sleeve 82 includes a number of sealing members 64 positioned in a second orientation extending from distal end 78. The medical apparatus 62 further includes a guide member 72 positioned in the second position. Medical apparatus 62 also includes a strippable liner 84, surrounding and in contact with, the adhesive material disposed on outer surface 91. The strippable liner has perforations 86 formed thereon.

Figure 9:
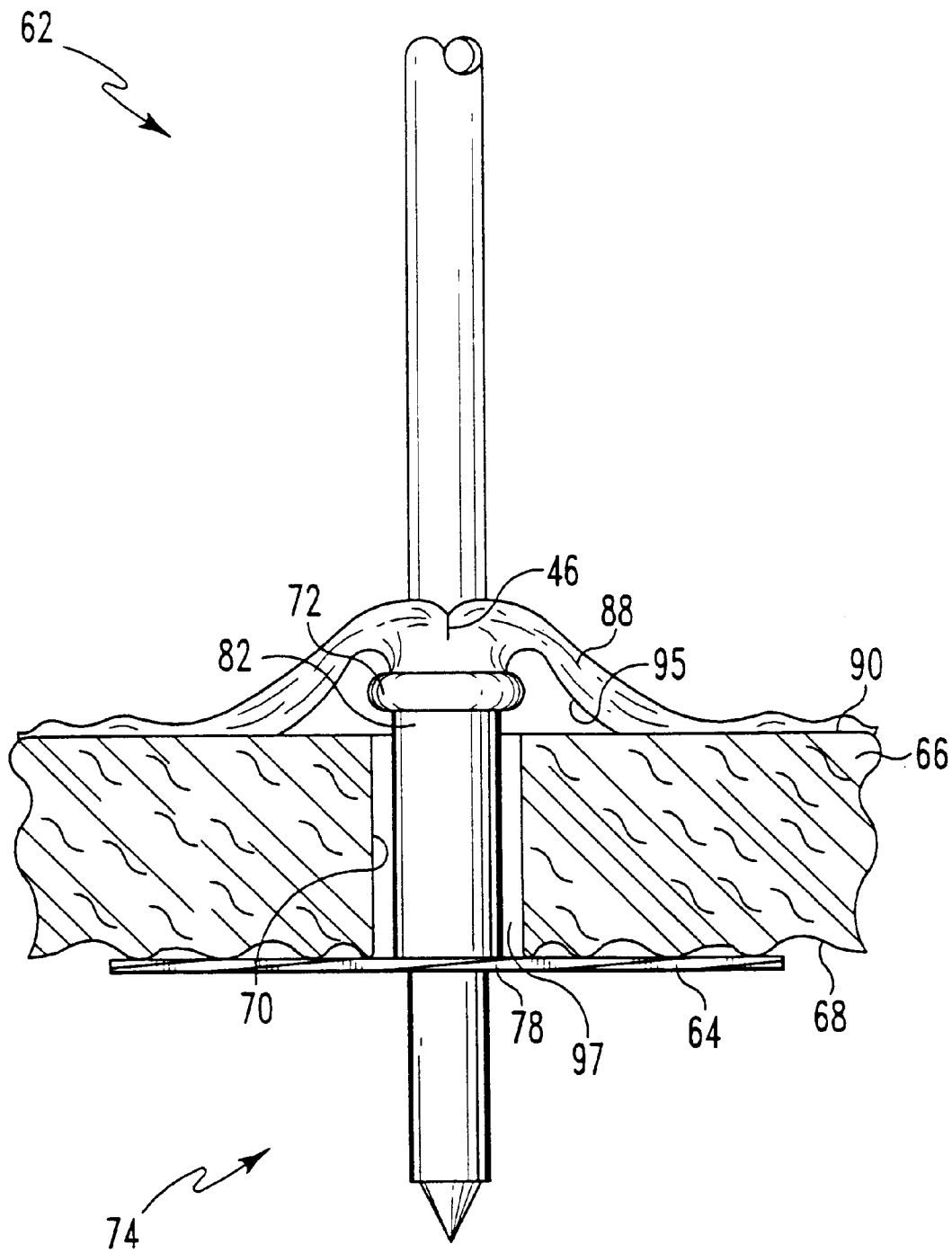
FIG. 9 is a fragmentary side elevational view of the medical apparatus shown in FIG. 8, with the strippable liner peeled off, and the sleeve peeled down and attached to an exterior surface of a body cavity wall.

Medical apparatus 62 is used in the same manner as described above with reference to medical device 10. However, once the sealing members are positioned in contact with an interior surface 68 of body cavity wall 66, strippable liner 84 is torn along perforations 86 to expose the adhesive material disposed on the outer surface 91 of sleeve 82. As shown in FIG. 9, sleeve 82 is then torn along perforations 86 down to guide member 72 to form a number of elongated strips 88 having a first surface 95 with the adhesive disposed thereon. It is also contemplated that sleeve 82 may be formed from a material having the physical property of molecular orientation whereby a tear in the material runs readily only in a longitudinal direction along the length of sleeve 82. A sleeve formed from such a material will eliminate the need for the above described perforations. Once the elongated strips 88 are formed, a first surface 95 of each strip 88 is attached to an exterior surface 90 of body cavity wall 66 with the adhesive.

An important aspect of using elongated strips 88 in the above described manner is that they cooperate with sealing members 64 to stabilize the position of medical apparatus 62 in opening 70. The attachment of elongated strips 88 to the exterior surface 90 of body cavity wall 66 also keeps sealing members 64 in contact with interior surface 68. This ensures that no fluid communication exists between an area inside of the body cavity 74 and an area outside the body cavity through the space 97 defined between the opening 70 and the sleeve 82.

FOURTH EMBODIMENT OF THE INVENTION

Figure 10:
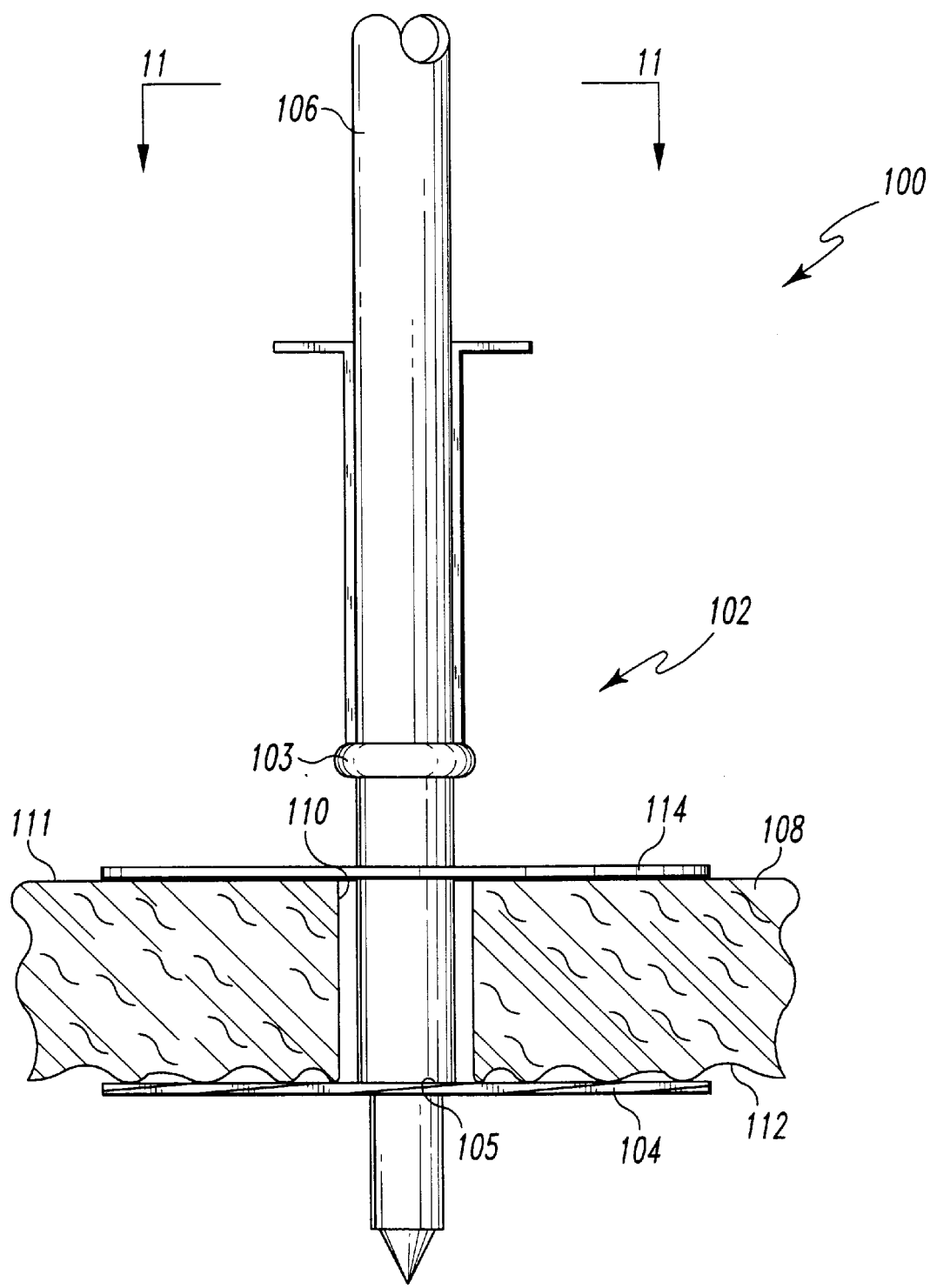
FIG. 10 is a fragmentary side elevational view of a medical apparatus similar to the one shown in FIG. 1, but this apparatus includes a lock member.

Now referring to FIG. 10, there is shown a medical apparatus 100 similar to the medical apparatus 10 shown in FIG. 1. Medical apparatus 100 is shown advanced through an opening 110 in a wall 108 of a body cavity. Medical apparatus 100 includes a sleeve 106 having a number of sealing members 104 positioned in the second orientation extending from distal end 105 of sleeve 106, and in contact with interior surface 112 of body wall 108. The medical apparatus 100 further includes an actuator 102 with a guide member 103 located in the second position. Medical apparatus 100 also includes a lock member 114 positioned in contact with sleeve 106 and exterior surface 111 of body cavity wall 108.

Figure 11:
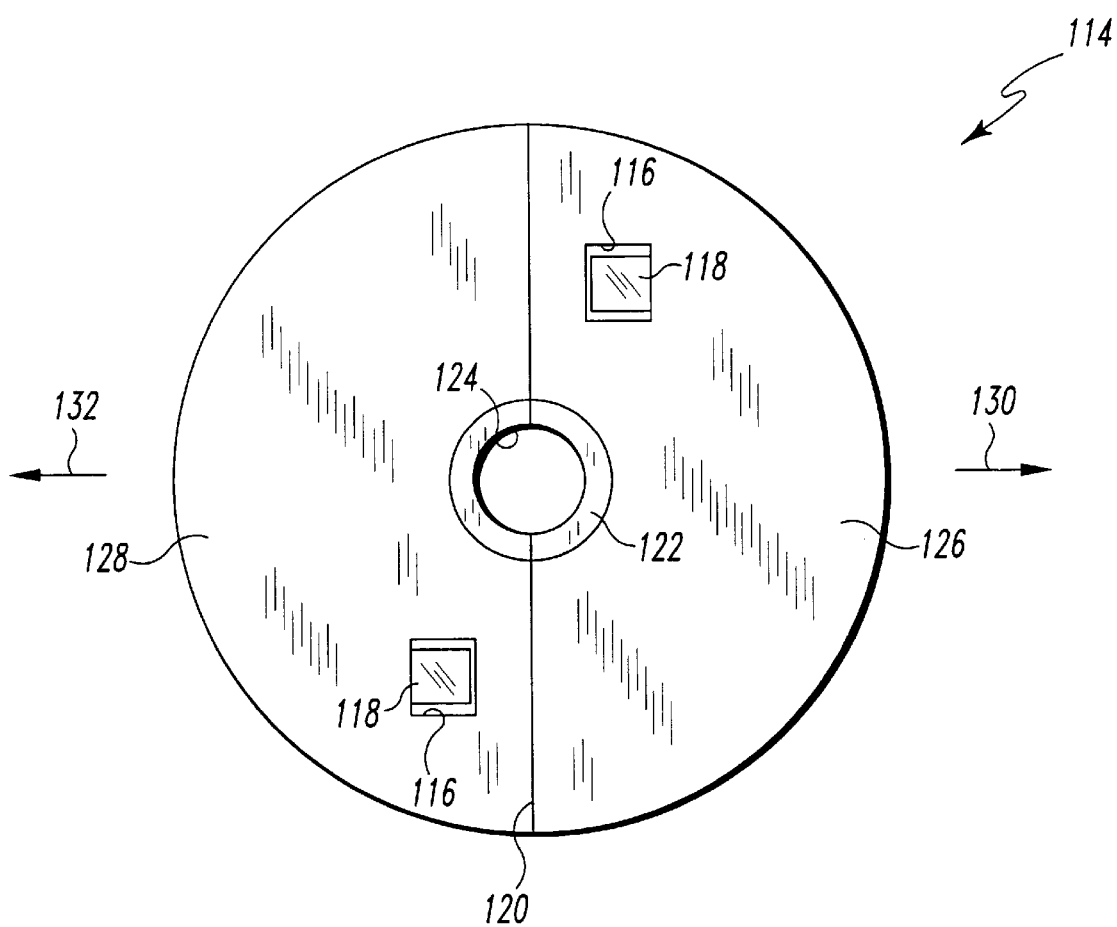
FIG. 11 is an elevational view of the lock member taken along line 11—11 of FIG. 10, with the body wall and the rest of the medical apparatus shown removed for clarity of description.

FIG. 11 is an elevational view of the lock member 114 taken along the line 11—11 of FIG. 10, with the body wall and the rest of the medical apparatus 100 shown removed for clarity of description. The lock member 114 is divided by a seam 120 into a first portion 128 and a second portion 126. Lock member 114 includes a fastening mechanism (which will be discussed in greater detail below) for fastening the first portion 128 to the second portion 126. The lock member also includes a positioning element 122 which defines an orifice 124 for accepting sleeve 106. The first portion 128 and the second portion 126 cooperate with each other so as to securely grasp the sleeve 106 therebetween. Lock member 114 can be made from any plastic material which is conventionally used in the medical device arts.

First portion 128 and second portion 126 can be separated by actuating the fastening mechanism (which will be discussed in detail below) and moving first portion 128 and second portion 126 in the direction of arrows 132 and 130, respectively. Separation of lock member 114 facilitates the insertion and removal of sleeve 106 from orifice 124.

Figure 12:
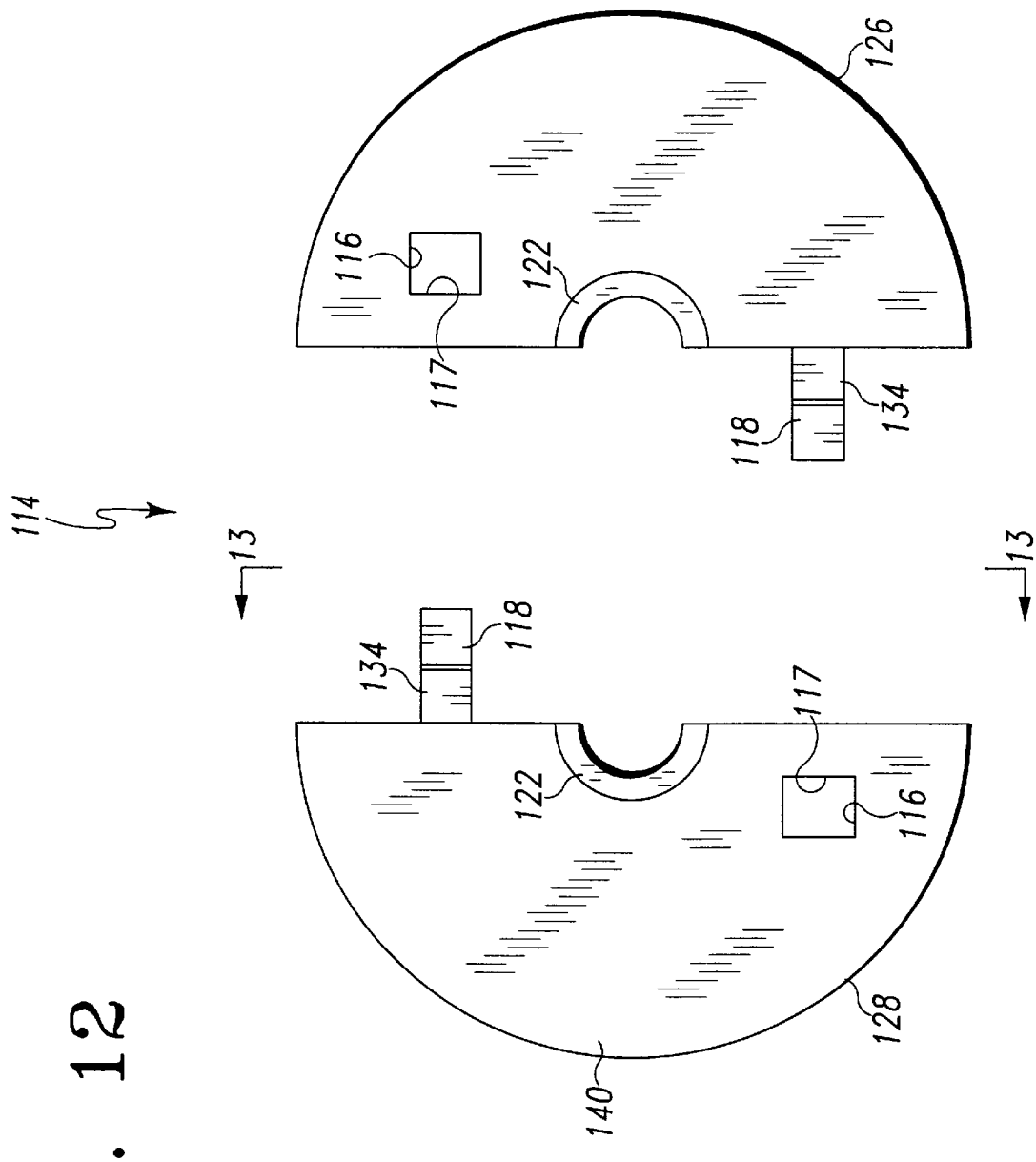
FIG. 12 is a side elevational view of the lock member of FIG. 11, with the first and second portions of the lock member shown separated.

As shown in FIGS. 11–14, the fastening mechanism includes a shaft 134 extending from an edge 142 of first portion 128. (It should be appreciated that, as illustrated in FIG. 12 second portion 126 has the same elements of the fastening mechanism as first portion 128. However, as discussed below, the fastening mechanism is arranged on second portion 126 to cooperate with those disposed on first portion 128.) The fastening mechanism also includes a clip 118 that obliquely extends from an end of shaft 134. Clip 118 is attached to shaft 134 using known manufacturing techniques that allows it to flex or bend around its point of attachment to shaft 134 in the directions indicated by arrow 141 (see FIG. 14).

Figure 13:
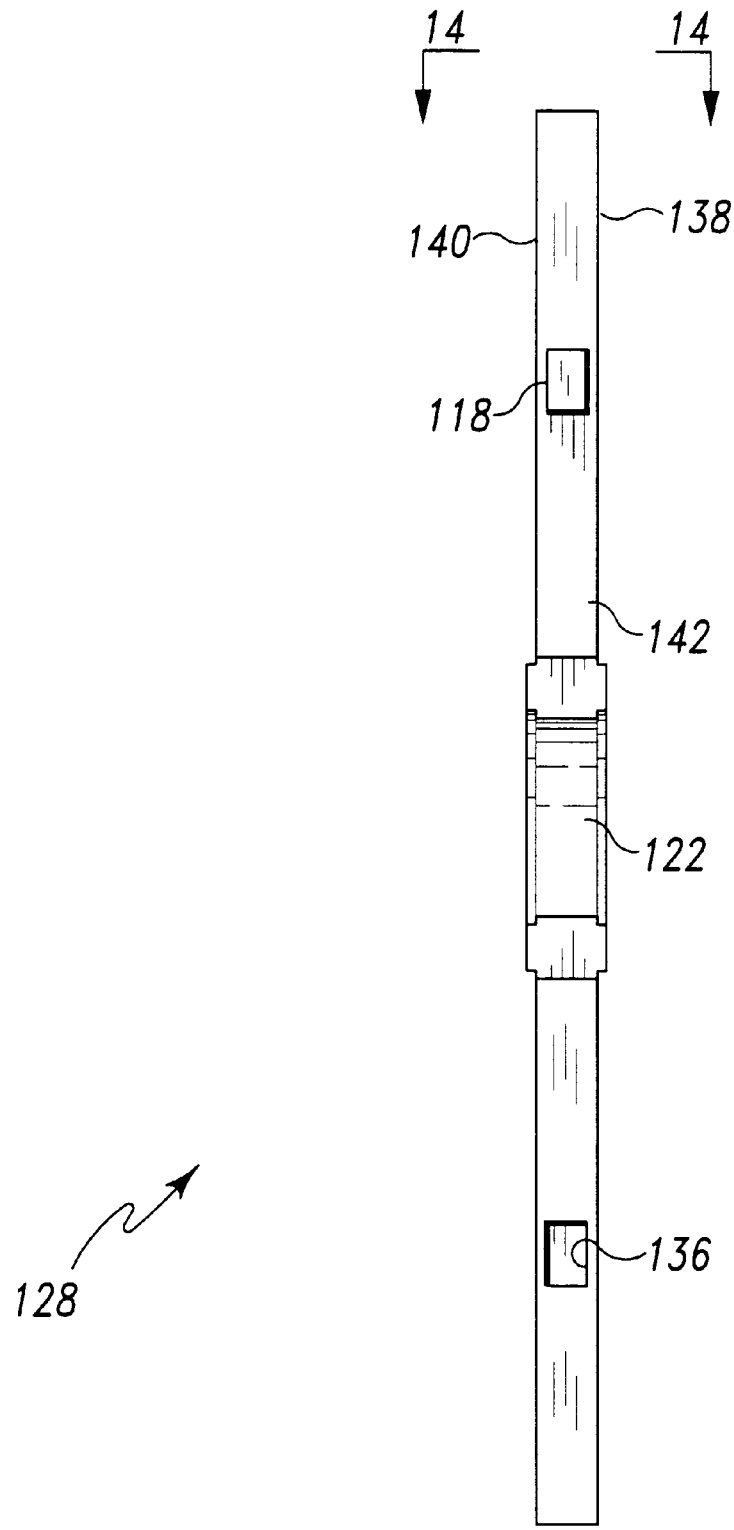
FIG. 13 is a side elevational view of the first portion of the lock member taken along line 13—13 of FIG. 12.
Figure 14:
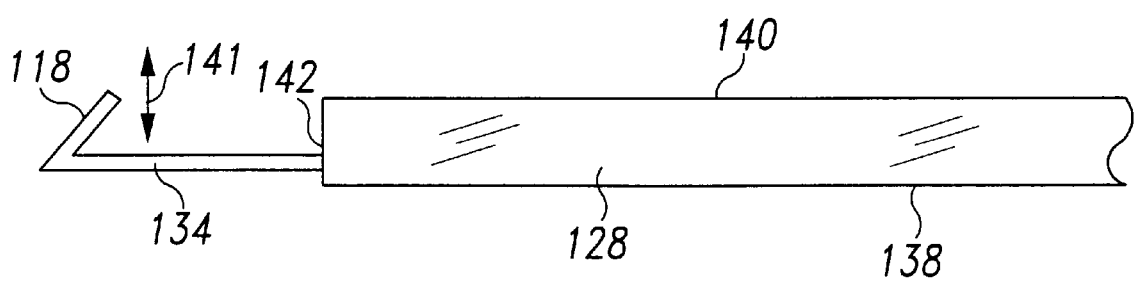
FIG. 14 is an enlarged fragmentary side elevational view of the first portion of the lock member taken along line 14—14 of FIG. 13.

As shown in FIG. 12 and 13, the fastening mechanism also includes a channel 136 defined in edge 142, which is connected to an aperture 116 formed on second surface 140 of first portion 128. Channel 136 is adapted to receive clip 118 and shaft 134, and has the appropriate height dimension so that clip 118 must bend toward shaft 134 upon its entrance into channel 136. Medical apparatus 100 is used in the same manner as described above in reference to medical device 10 (see FIG. 1). However, once sealing members 104 are positioned in contact with interior surface 112, first portion 128 and second portion 126 of lock member 114 are positioned relative to each other so that the fastening mechanism elements can cooperate to join first portion 128 and second portion 126 along seam 120 (see FIG. 12). First portion 128 and second portion 126 are also positioned relative to sleeve 106 such that the sleeve 106 is positioned in orifice 124 and in contact with positioning element 122 when these portions are joined along seam 120. Once first portion 128 and second portion 126 are positioned in the above described manner, they are moved toward each other such that clip 118 and shaft 134 extending from second portion 126 enters channel 136 of first portion 128, and clip 118 and shaft 134 extending from first portion 128 enters the channel (not shown; identical to channel 136) located on the edge of second portion 126. As described above, as each clip 118 enters its respective channel 136 it is bent toward shaft 134 until entering its aperture 116. Once positioned in aperture 116 each clip snaps back to its unbent configuration where it engages wall 117 (see FIG. 12) thereby preventing the separation of the first portion 128 and second portion 126. The lock member can then be moved along the longitudinal axis of sleeve 106 until it contacts the exterior surface 111 of body cavity wall 108. As a result, wall 108 is trapped or "sandwiched" between lock member 114 and sealing member 104 thereby locking medical apparatus 100 into position with respect to wall 108. It should be understood that lock member 114 can also have any of the well known medical adhesives disposed thereon to facilitate its engagement with exterior surface 111. It should also be understood that a fastening mechanism utilizing velcro type fasteners can also be used in the present invention.

An important aspect of using lock member 114 in the above described manner is that the sealing members 104 remain in contact with interior surface 112 during the manipulations of medical apparatus 100 required by a medical procedure. By keeping sealing members 104 in contact with interior surface 112 fluid communication between an area inside of the body cavity and an area outside of the body cavity through opening 110 is prevented. Thus, the port site wound is protected from being exposed to potentially harmful substances including exfoliated cancer cells and/or infectious agents.

Another advantage of using lock member 114 is that it helps maintain a substantially gas tight seal between the interior and exterior of a body cavity, which ensures that no unexpected loss of a pneumoperitoneum will occur during a medical procedure. This is especially true when an adhesive is used to attach lock member 114 to exterior surface 111. It should be appreciated that preventing an uncontrolled loss of the pneumoperitoneum is important since such a loss can complicate the medical procedure being performed, and increase the potential that the port site wound will be contaminated with tumor cells or infectious microbes.

The use of lock member 114 may also eliminate the need for anyone to hold medical apparatus 100 in the appropriate position during surgery, thereby freeing them to perform other tasks. This is true since the first portion 128 and the second portion 126 cooperate with each other to securely grasp the sleeve 106 therebetween.

Once the medical procedure is completed, lock member 114 can be removed by depressing clip 118 (for example with a finger) toward shaft 134, (see FIG. 14) such that clip 118 can be inserted into channel 136, and moving first portion 128 and second portion 126 in the direction of arrows 132 and 130, respectively (see FIG. 11). Medical apparatus 100 can then be removed from the opening 110 as described above in reference to medical apparatus 10.

FIFTH EMBODIMENT OF THE INVENTION

Figure 15:
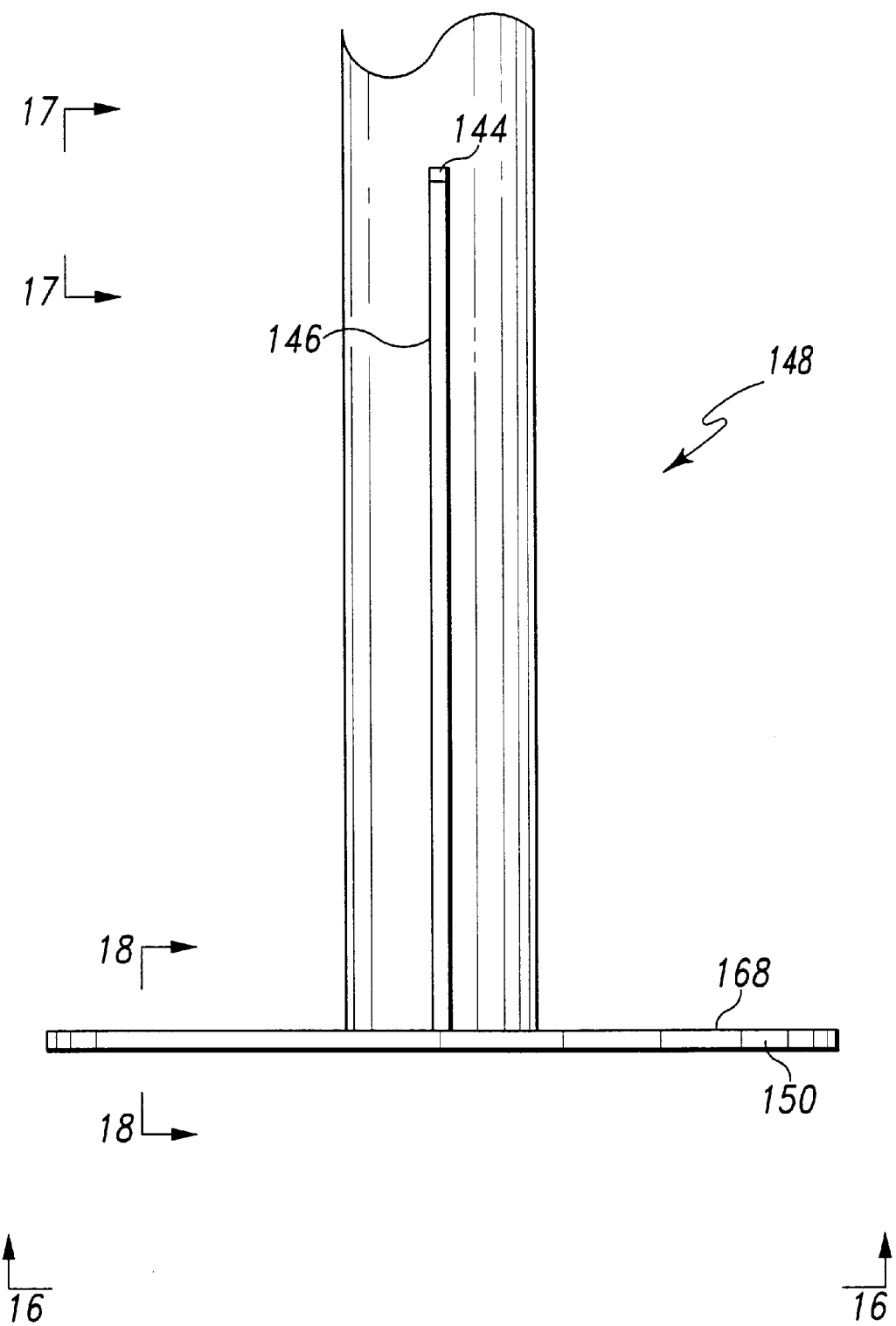
FIG. 15 is a side elevational view of another sleeve which incorporates the features of the present invention.
Figure 16:
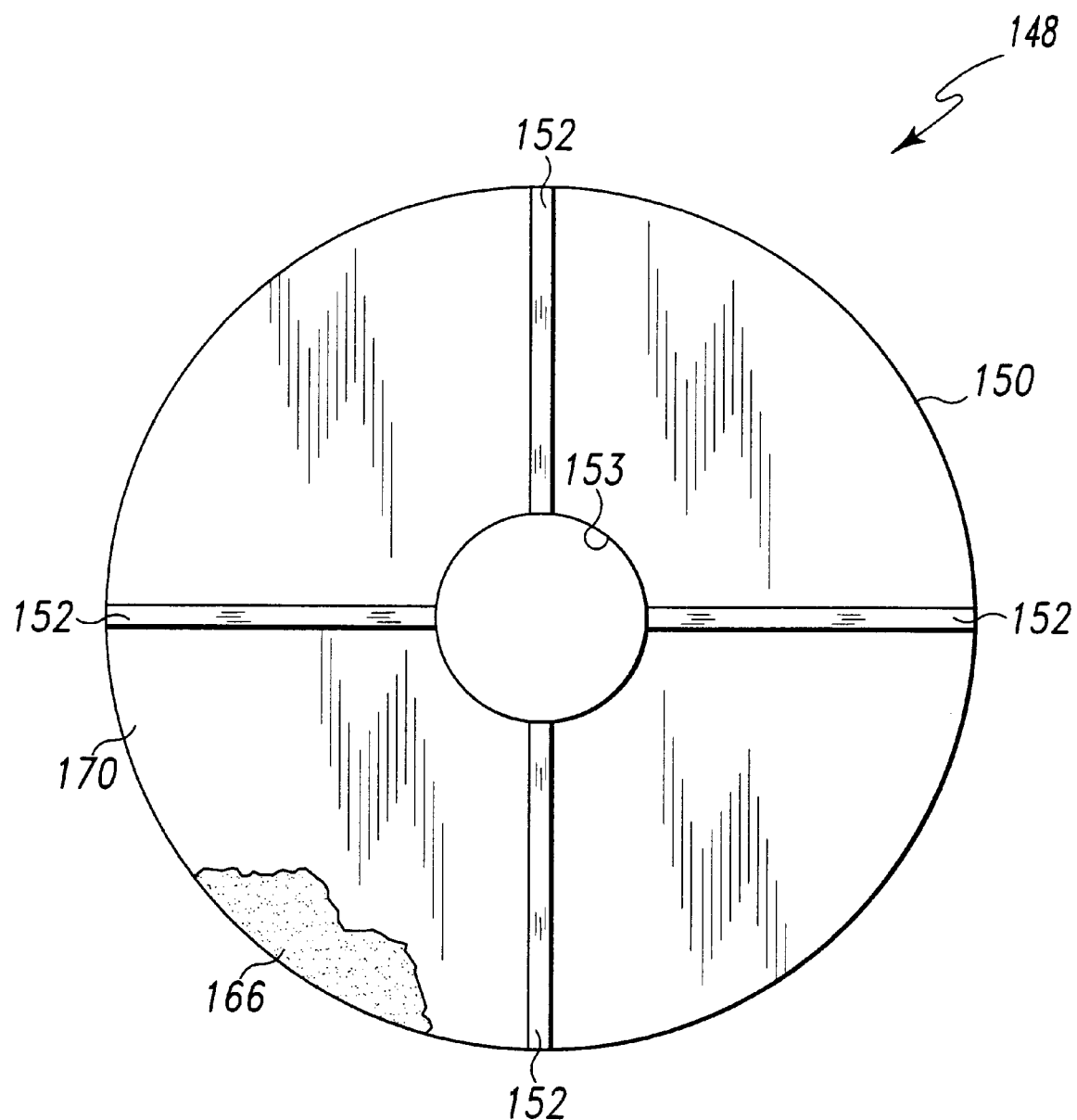
FIG. 16 is a side elevational view of the sealing member of the sleeve taken along line 16—16 of FIG. 15 with a biologically active compound disposed thereon (note that the biologically active compound is shown disposed on only a portion of the sealing member for clarity of description)
Figure 17:
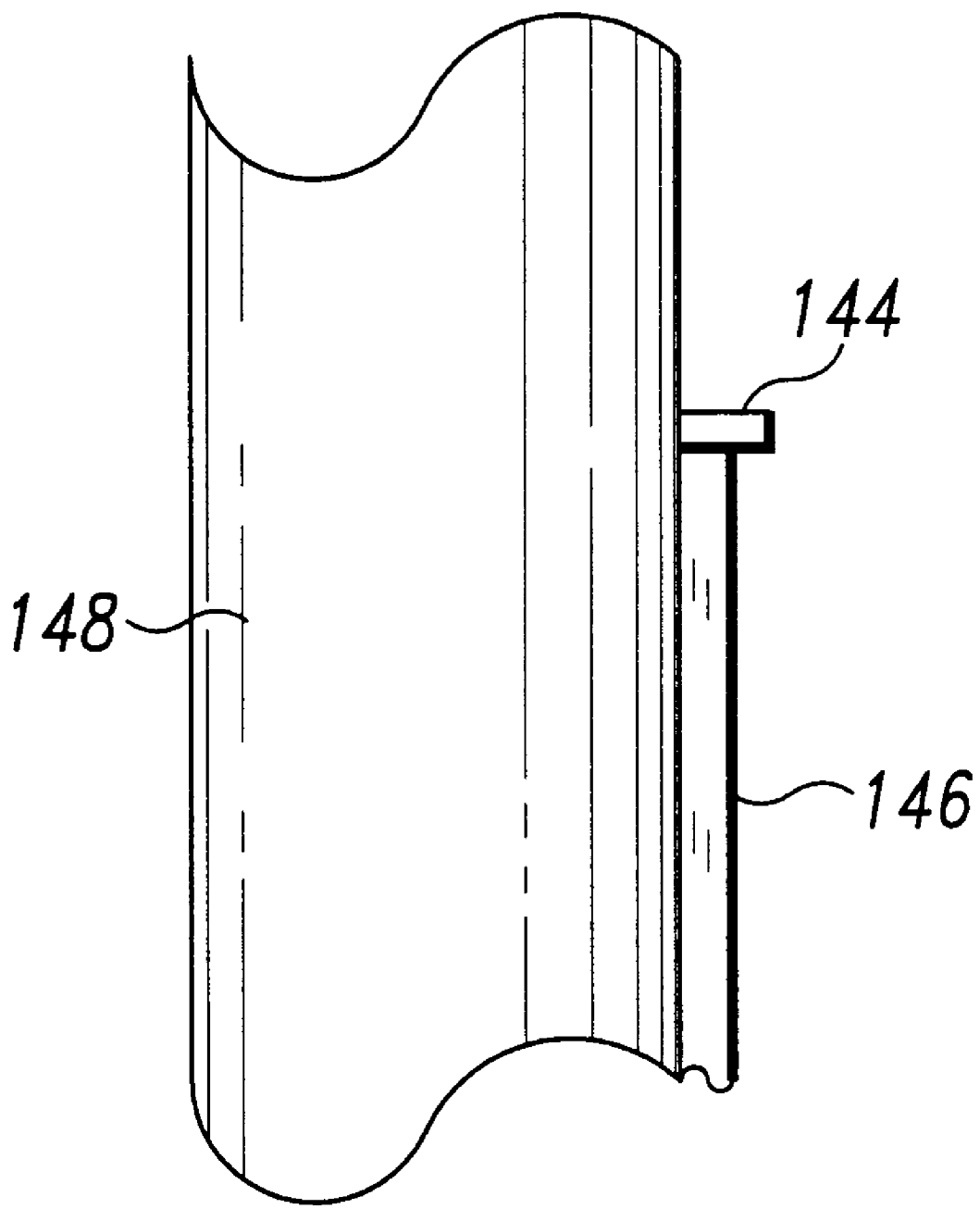
FIG. 17 is a fragmentary side elevational view of the sleeve taken along line 17—17 of FIG. 15.

Now referring to FIGS. 15–17, there is shown a sleeve 148 similar to sleeve 18 shown in FIG. 1 or sleeve 106 shown in FIG. 10. Sleeve 148 can be substituted for sleeve 18 or sleeve 106 in medical apparatus 10 or 100, respectively. Moreover, sleeve 148 is used in a similar fashion as described for sleeve 18 or sleeve 106. However, as discussed in greater detail below, sleeve 148 includes a single sealing member 150 that defines a flexible gas impervious bag having a void 157 therein (see FIG. 18). One flexible gas impervious bag which may be used with some modification is disclosed in U.S. Pat. No. 3,762,404 issued to Sakita which is herein incorporated by reference. In particular, the void 157 contains a charge of small particles or beads 156 which consolidate or interengage into a rigid structure when the void 157 is evacuated. As shown in FIG. 16, the sleeve 148 has a passageway 153 extending therethrough adapted to accept a trocar assembly (not shown) which includes a cannula and a trocar. Sleeve 148 also has a number of support members 152 extending from a distal end of sleeve 148 (see FIG. 16) which engage sealing member 150. Support members 152 are formed such that when no force is applied to them they spontaneously assume the second orientation which is in a substantially orthogonal relationship with passageway 153 (see FIG. 16) thereby lifting and supporting the engaged sealing member 150 in its second orientation (see FIGS. 15 and 16). Moreover, support members 152 are flexibly attached to the distal end of sleeve 148 such that when force is applied (i.e. the force applied by sliding a guide member over support members 152 and sealing member 150) the support members 152 and the sealing member 150 assume their first orientation (i.e. positioned in a substantially parallel relationship with passageway 153).

As shown in FIGS. 15 and 17, sleeve 148 also includes a valve 144 and a vacuum line 146 in fluid communication with void 157. Valve 144 can have a well known female Luer-lock connector for attaching a vacuum hose (not shown) thereto. Moreover, valve 144 can be any of a number of well known valves capable of maintaining and then releasing a vacuum, as long as the size of the valve does not interfere with the operation of the medical apparatus into which sleeve 148 is incorporated. For example valve 144 can be a trumpet valve or a conventional two or three way stop cock valve.

Figure 18:
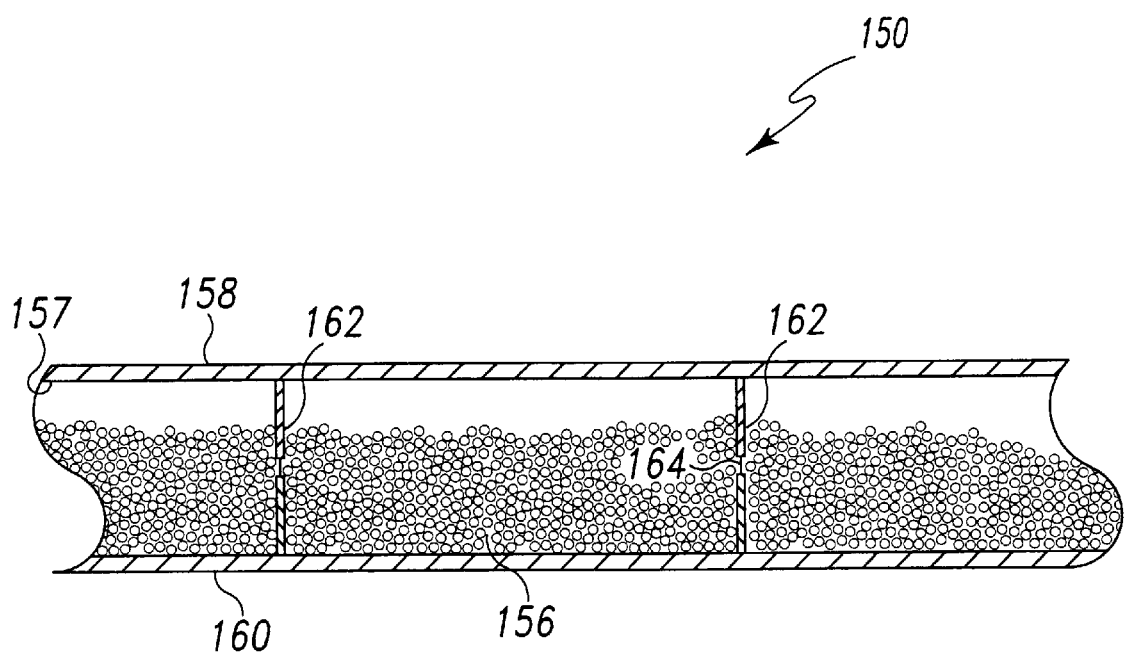
FIG. 18 is an enlarged fragmentary cross sectional view of the sealing member taken along line 18—18 of FIG. 15.

As illustrated in FIG. 18, the bag structure defined by sealing member 150 includes a first wall 158 and a second wall 160 with interior void 157 therebetween. The bag structure also includes a number of partitions 162 secured to and extending between first wall 158 and second wall 160 that divide interior void 157 into a number of compartments. These partitions 162 confine a portion of the charge of beads 156 into their respective compartment. It should be appreciated that having the beads 156 divided and confined into a number of compartments prevents the beads from being redistributed by gravity as sealing member 150 is moved between its first and second orientations, as well as, any movement which the beads are subjected to prior to evacuation of void 157. Each partition 162 has a screen 164 mounted therein which is adapted to allow the flow of a fluid therethrough but prevents a flow of beads from one compartment to another. Thus all the compartments are in fluid communication with one another and only one valve 144 and one vacuum line 146 are required to evacuate interior void 157.

The beads 156 occupying interior void 157 must be sufficiently rigid to withstand the stresses that result when they interengage upon evacuation of void 157. Beads 156 must also have a high mechanical strength so that void 157 can be repeatedly evacuated without the accompanying attrition or fracture of the beads 156. Beads 156 should also be elastically deformable such that when void 157 is evacuated they can move freely into close interengagement to form a stable, rigid structure.

Beads of expanded plastic material, such as polystyrene and polyvinyl chloride are preferred because of their high mechanical strength, elastic deformability and low specific gravity. The expression "specific gravity" is intended to mean a true specific gravity. Thus, when such beads are made hollow the specific gravity of the beads is represented by its weight divided by its total volume including the hollow space therein. The specific gravity of the beads used in the present invention should be in the range of from about 0.1 to about 0.6. Such values are readily attainable with foamed synthetic resins, although other material can be used for beads 156 when they have a low specific gravity in the range specified above and satisfy the mechanical strength and elastic deformability requirements.

The beads used in the present invention can be from about 0.5 to about 2 millimeters in diameter. Moreover, beads which are uniform in size and shape can be used, but a mixture of substantial portions of beads of at least two materially different sizes within the indicated range can also be used.

Any appropriate vacuum source (not shown) can be used to evacuate void 157. Such a vacuum source can be manually operated or power driven. Examples of vacuum sources which can be used in the present invention include a wall suction apparatus, aspirator pumps, syringe, or any other convenient operating vacuum source.

A medical apparatus incorporating sleeve 148 is used in a similar manner as described above in reference to medical device 10 and medical device 100. However, once sealing member 150 is positioned in contact with an interior surface of a body cavity wall, an end of a vacuum hose (not shown) is attached to valve 144 with the other end being attached to a vacuum source (not shown). A vacuum is pulled through valve 144 and vacuum line 146 thereby evacuating each compartment of interior void 157. It should be understood that since each partition 162 has a screen 164 therein, they will be in fluid communication with one another, therefore only one valve 144 and vacuum line 146 is required to evacuate interior void 157. As the vacuum is created inside interior void 157 the outside pressure present within the body cavity (e.g. an insulated peritoneum) forces the beads 156 together into close interengagement so they cannot move. This interengagement of beads 156 upon evacuation of interior void 157 causes beads 156 to form a stable rigid structure, thereby converting sealing member 150 from its pre-evacuation state of being a soft, pliable, deformable, flaccid structure (i.e. bean bag like) to its post-evacuation state of a stable rigid structure. When sealing member 150 is in its post-evacuation state, and in contact with an interior surface of a body cavity wall it effectively prevents fluid communication between an area inside of the body cavity and an area outside of the body cavity through a space defined between an opening in a wall of the body cavity and sleeve 148.

Once the medical procedure is completed, the surgeon (not shown) removes specimens (not shown) and instruments (not shown) from the body cavity and releases the intra-abdominal pressure. Then the vacuum is released and gas re-enters interior void 157 thereby disrupting the interengagement of beads 156. As a result sealing member 150 returns to its soft, pliable pre-evacuation state whereupon support member 152 (and therefore sealing member 150) are forced to assume their first orientation in the same manner as described above in reference to medical apparatus 10. Then the medical apparatus incorporating sleeve 148 is then withdrawn from the opening created in the body cavity wall.

An important aspect of using sealing member 150 in the above described manner is that in its pre-evacuation state its soft pliable nature allows it to conform to any irregular or protruding structures encountered on the interior surface of the body cavity wall. Then upon evacuation, sealing member 150 forms a rigid structure surrounding the encountered structure thus providing a fluid tight seal between the interior of the body cavity and the port site wound.

SIXTH EMBODIMENT OF THE INVENTION

Figure 24:
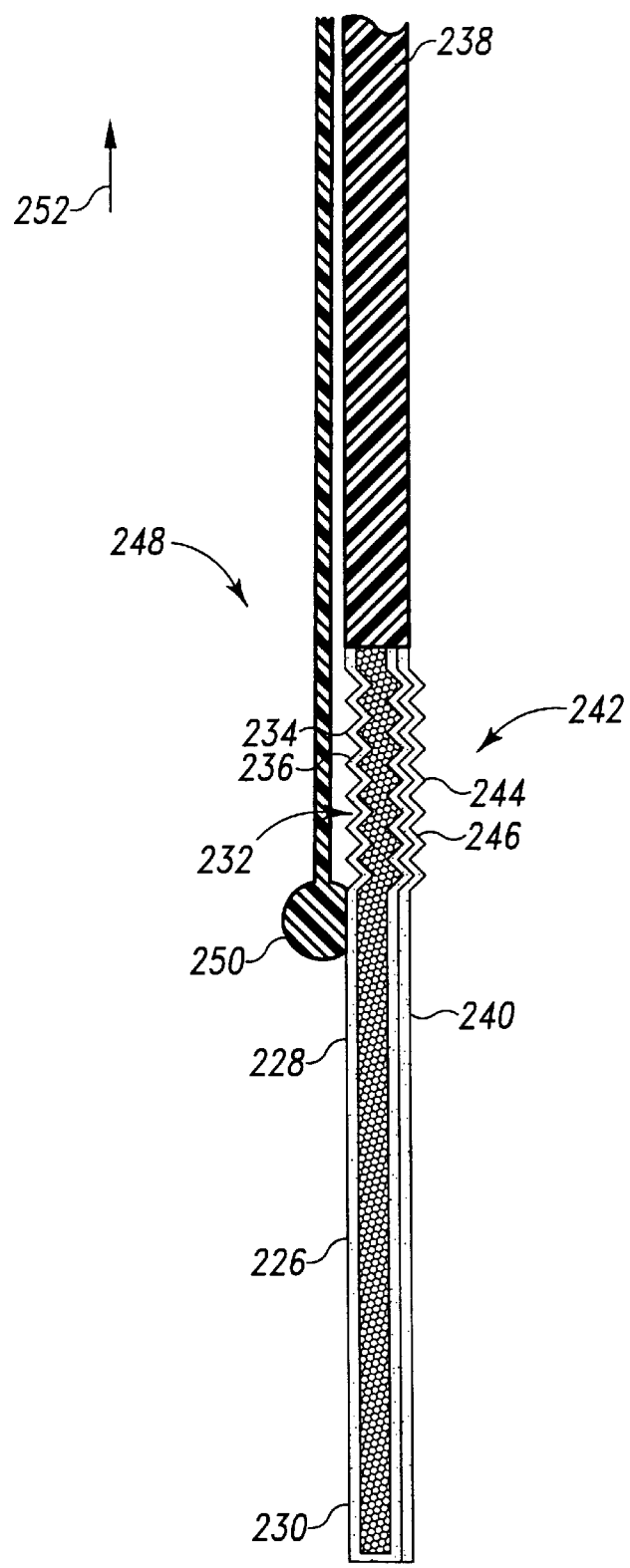
FIG. 24 is a fragmentary cross sectional view of a sleeve, a sealing member (positioned in the first orientation), a support member, and an actuator which are similar to the ones shown in FIGS. 15 and 16, but with the sealing member and the support member having corrugated areas defined thereon.
Figure 25:
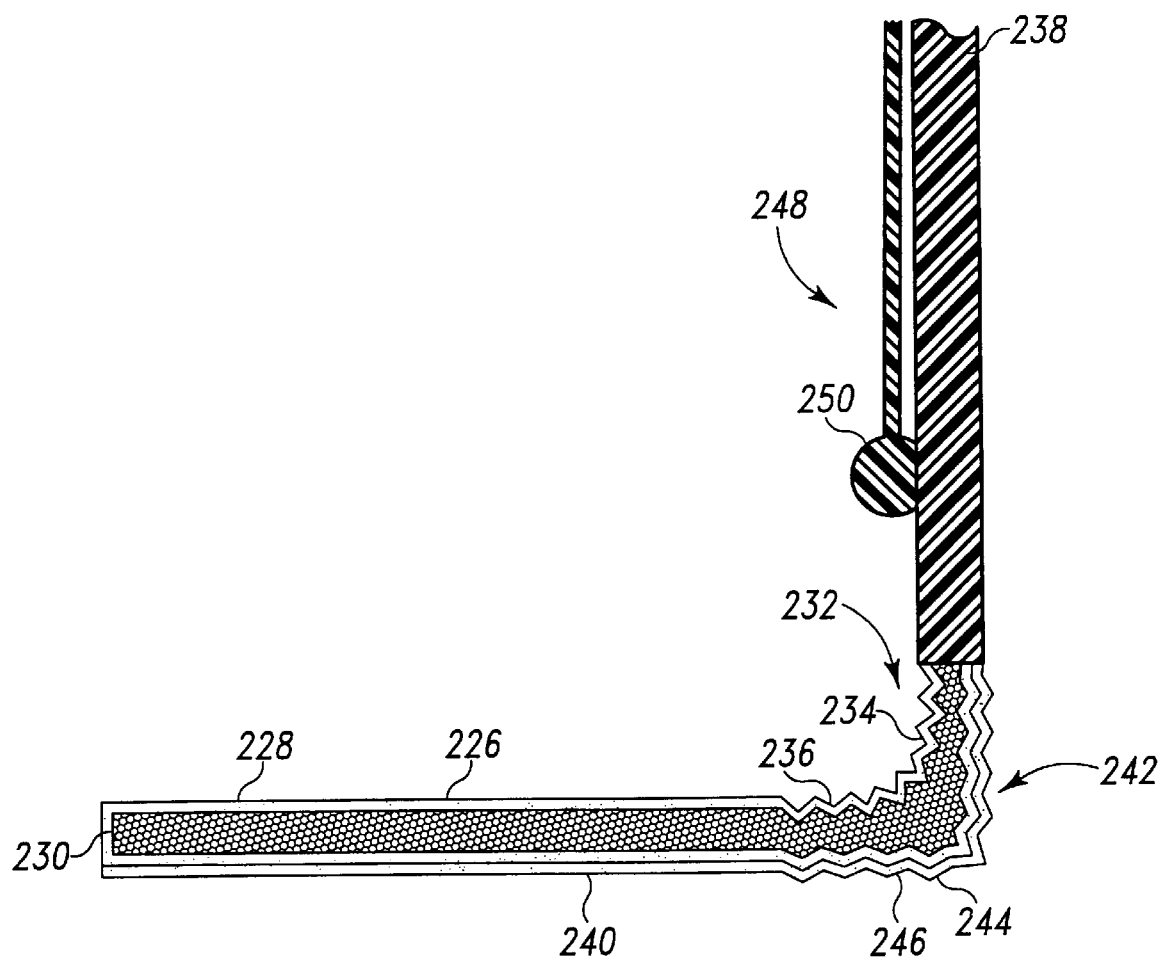
FIG. 25 is a fragmentary cross sectional view of the sleeve, the sealing member, the support member, and the actuator shown in FIG. 24, but with the actuator positioned such that the sealing member assumes the second orientation.

Now referring to FIGS. 24 and 25, there is shown a portion of a sleeve 238, a portion of sealing member 226, and a portion of a support member 240. Sleeve 238, sealing member 226, and support member 240 are somewhat similar to sleeve 148, sealing member 150 and support members 152 shown in FIGS. 15–17. Sleeve 238, sealing member 226 and support member 240 can be substituted for sleeve 148, sealing member 150, and each support member 152, respectively. In addition, sleeve 238, sealing member 226, and support member 240 are used and constructed in a somewhat similar fashion as described above for sleeve 148 and sealing member 150. However, sealing member 226 has a corrugated area 232 defined thereon by a plurality of ridges 234 and associated grooves 236. In addition, support member 240 has a corrugated area 242 defined thereon by a plurality of ridges 244 and associated grooves 246.

Sealing member 226 is moved from the first position (see FIG. 24) to the second position (see FIG. 25) by moving actuator 248 in a direction indicated by arrow 252 (see FIG. 24) until guide member 250 is no longer in contact with sealing member 226 as shown in FIG. 25. Once guide member 250 is no longer in contact with sealing member 226, support member 240 spontaneously assumes its second orientation thereby lifting and supporting sealing member 226 in its second orientation (see FIG. 25). Corrugated area 232 and corrugated area 242 facilitate the movement of sealing member 226 from the first orientation to the second orientation by enhancing the flexibility of sealing member 226 and support member 240 in an area adjacent to sleeve 238. However, it should be understood that even though the flexibility of sealing member 226 and support member 240 is enhanced by corrugated area 232 and corrugated area 242, as with sealing members 20 and sealing member 150, sealing member 226 is held in contact with an interior surface of a body cavity wall (not shown) so as to prevent any fluid communication between an area inside of the body cavity and an area outside of the body cavity through a space (not shown; see FIG. 4) defined between an opening in the body cavity wall (not shown; see FIG. 4) and sleeve 238.

SEVENTH EMBODIMENT OF THE INVENTION

The present invention also includes a number of sealing members having a biologically active compound disposed thereon, such as an antibiotic, a cytotoxic agent or a compound which effectively inhibits tumor cell adherence to a membrane. As illustrated in FIG. 16, a biologically active compound 166 can be disposed on the side of sealing member 150 which does not engage the interior surface of the body cavity wall, referred to herein as non-contacting surface 170. However, it should be understood that biologically active compound 166 can also be disposed upon a contacting surface 168 (see FIG. 15) of sealing member 150 or on both of these surfaces. Moreover, it should be appreciated that biologically active compound 166 can be disposed upon sleeve 148 so that when it is positioned within a body cavity, biologically active compound 166 is in direct contact with opening 110. It should also be understood that biologically active compound 166 can also be disposed upon guide member 103. By doing so, the action of sliding guide member 103 into opening 110 will bring the same into contact with biologically active compound 166.

If necessary, in order to keep biologically active compound 166 from falling or sliding off sealing member 150 due to gravity as it is being positioned between the first and second orientation, biologically active compound 166 can contain a suitable pharmaceutically acceptable carrier. A pharmaceutically acceptable carrier will also aid in retaining all, or a portion of, the biologically active compound 166 on sealing member 150 as it is being advanced through an opening in a body cavity wall. Such pharmaceutically acceptable carriers include known excipients and auxiliaries which facilitate the processing of biologically active compound 166 into a preparation which has the appropriate consistency to be disposed on sealing member 150.

Suitable excipients which may be used to prepare a pharmaceutically acceptable carrier, such as a paste, a viscous solution or a powder which includes fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Additionally, silica, talc, stearic acid or salts thereof such as magnesium stearate or calcium stearate, and/or polyethylene glycol can be used.

In addition, a suspension of biologically active compound 166 may be disposed on sealing member 150. Suitable vehicles for such suspensions include sesame oil or synthetic fatty acid esters, for example, ethyl oleate or triglycerides. Such suspensions can include substances which increase the viscosity of the suspension including, for example, sodium carboxymethyl cellulose, sorbitol and/or a dextran.

The exact formulation of a pharmaceutically acceptable carrier will depend upon the particular nature of biologically active compound 166 to be disposed upon sealing member 150. It should also be understood that biologically active compound 166 can also be disposed upon the sleeve, such as sleeve 106, and the guide member, such as guide member 103. Moreover, the amount of biologically active compound 166 to dispose on sealing member 150 will depend upon the age, sex, weight, condition of the recipient, kind of concurrent treatment, if any, frequency of treatment and the nature of the effect desired. However, the amount of biologically active compound 166 to dispose on sealing member 150 is large enough to produce the desired effect but not so large as to cause adverse side effects, such as unwanted cross reactions, anaphylactic reactions and the like. Counterindication, if any, immune tolerance and other variables will also affect the proper amount to be disposed on sealing member 150. The exact formulation of a pharmaceutically acceptable carrier and the amount of biologically active compound 166 contained therein (and therefore the amount disposed on sealing member 150) is easily determinable by one of ordinary skill in the art from only routine experimentation and by applying well know principles of therapeutics as set forth, for example, in Gilman, Alfred G. et al., eds., *The Pharmacological Basis of Therapeutics*, 6$^{th}$ Edition, Macmillan Publishing Co., Inc. New York, N.Y. (1980) which is herein incorporated by reference. Preferably, such preparations will contain about 0.001 to about 99 percent biologically active compound 166 together with the pharmaceutically acceptable carrier.

A large number of antimicrobial agents (antibiotics) or antiseptics are contemplated for use as biologically active compound 166 in the present invention. Preferably, where possible, the antibiotic should be active against both Gram-positive and Gram negative pathogens. The following are illustrative of the antibiotics and/or antiseptics which can be disposed on sealing member 150 to aid in the control, inhibition or prevention of infections of the port site wound: (i) metal salts, or like compounds with antibacterial metal ions, e.g. copper or silver, and optionally with additional nonmetallic ions of antibacterial properties; (ii) topical antibiotics, e.g. neomycin, soframycin, bacitracin, polymcin; (iii) antibacterials such as chlorhexidine and its salts; (iv) quaternary ammonium compounds, e.g. centrimide, domiphen bromide, and polymeric quaternaries; (v) iodophors such as povidone iodine, and polyvinylpyrrolidoneiodine (PVP-I); (vi) acridine compounds such as 9-aminoacridine, 3,6-diaminoacridine and 6,9-diamino-2-ethoxyacridine; and (vii) biguanidide compounds such as 1,6-di(4-chlorophenylbiguanido)hexane, diaminohexylbiguanide, 1,6-di(aminohexylbiguanido) hexane, and polyhexamethylenebiguanide. Additional suitable antibiotics include aminoglycoside antibiotics such as amikacin, butirosin, dideoxykanamycin B (DKP), fortimycin, gentamycin, kanamycin, lividomycin, neomycin, netilmicin, ribostamycin, sagamycins, seldomycins and their epimers, sisomicin, sorbistin, tobramycin, streptomycins, linkomycins such as clindamycin, lincomycin and rifamycins such as rifampicin and rifamycin. Antibiotics such as polymyxin B sulfate-neomycin sulfate, cleocin phosphate® (available from the Upjohn Company, Kalamazoo, Mich.) and erythromycin ethylsuccinate are also contemplated.

Examples of suitable antiseptics include bromchlorophen, hexetidine, buclosamide, salicylic acid, cerium nitrate, chlorhexidine, 5-chloro-8-hydroxyquinoline, copper 8-hydroxyquinolate, acridine orange, undecenoic acid, undecoylium chloride and silver salts such as silver sulfadiazine, mafenide, nitrofurazole, cloflucarban, tribromasalan, taurolin and noxythiolin.

With respect to aiding in the control, inhibition or prevention of tumor cell adhesion and implantation and the subsequent metastasis in the port site wound, compounds which effectively block or inhibit tumor cell adhesion (please note that tumor cell adhesion is a step in the metastasis cascade), or destroy tumor cells before adhering to either the port site wound, or other sites, can be disposed on sealing member 150. Types of compounds which effectively block or inhibit tumor cell adherence include anticoagulants, fibrinolytic agents and compounds which alter the electrical charge of a membrane surface. For example, the surface charge altering and anticoagulant heparin can be disposed on sealing member 150. Additionally, any of several water-soluble high molecular weight glucose polymers (average molecular weight (MW) 75 kdal) otherwise known as dextrans, can also be disposed on sealing member 150 to alter the surface electrical charge of nearby membranes thereby blocking tumor cell adhesion. Preferably a dextran having an average MW of about 40 kdal is used to coat sealing member 150.

As stated above, tumor cell destroying compounds, hereinafter referred to as cytotoxic compounds, can also be disposed on sealing member 150, with or without an acceptable pharmaceutically acceptable carrier. These compounds include cisplatin, carboplatin, 5-fluorouracil, providoneiodine, tumor necrosis factor (TNF)-α, tauromustine, mitomycin C, camptothecin, bleomycin, indomethacin, N-methyl formamide, tamoxifen, sodiumhypochlorite, chlorhexidinecetrimide, adriamycin, methotrexate. Tumor cell destroying compounds also include antimetabolites such as cytarabine, azaribine, mercaptopurine, thioguanine; natural products such as vinblastine, vincristine, dactinomycin, daunorubicin, doxorubicin, bleomycin, mithramycin, mitomycin; and other miscellaneous agents such as cisplatin, hydroxyurea, procarbazine and mitotane, Alkylating agents such as mechlorethamine, nitrogen mustards, ethlenimine derivatives, alkyl sulfonates, nitrosoureas, and triazenes are also contemplated. Moreover, the compounds disclosed by Krakoff, Irwin H. in *Systemic Treatment of Cancer*, CA Cancer J. Clin., vol. 46, No. 3, pages 134–141 (May/June 1996), which is incorporated herein by reference, are contemplated for being disposed on sealing member 150.

In addition antiangiogenesis agents such as angiostatin are included in the group of cytotoxic compounds to be disposed on sealing member 150. Moreover, antibodies, including human monoclonal antibodies are included as cytotoxic compounds. Preferably, the human monoclonal antibody HuMab SK1 as described by Chang, Helena R. et al. in *Human Monoclonal Antibody SK1-Mediated Cytotoxicity Against Colon Cancer Cells,* Dis. Colon Rectum, vol. 36, No.12, pages 1152–1157 (December 1993) which is incorporated herein by reference, is disposed on sealing member 150. Other monoclonal antibodies can also be disposed on sealing member 150, for example those produced from hybridomas having the accession numbers HB8573, HB8232 and HB8250 available from the American Type Culture Collection, located at 12301 Parklawn Drive, Rockville Md., 20852. Furthermore, interleukin 2 (IL-2), cytokines or lymphokines are also included in the group of cytotoxic compounds of the present invention. It should also be understood that a combination of any of the above compounds can be disposed on sealing member 150.

In order to apply biologically active compound 166 to sealing member 150, the sealing member 150 is positioned in the second orientation (as previously described). Then, the biologically active compound 166 is disposed on the sealing member 150. Thereafter, sealing member 150 is repositioned to assume its first orientation, and then inserted through the opening defined in the body cavity wall as previously described. Then, the sealing member 150 is repositioned to assume its second orientation and thereafter moved into contact with the interior surface of the body wall cavity. It should be understood that biologically active compound 166 can be disposed on the contacting surface 168, the non-contacting surface 170 (see FIG. 16) or on both of these surfaces.

As discussed above, depending upon the nature of biologically active compound 166 (i.e. its ability to remain disposed on sealing member 150 when placed in the second orientation and advanced through an opening in a body cavity wall), it may be mixed with a pharmaceutically acceptable carrier prior to being disposed on sealing member 150. For example, biologically active compound 166 is suspended or dissolved in a 1% aqueous (weight/volume) solution of carboxymethylcellulose (CMC) before being applied to sealing member 150 (prospective example). Such a CMC solution provides the necessary viscosity to keep biologically active compound 166 from sliding or rolling off sealing member 150 when it is in the first position and being advanced through an opening in a body cavity wall.

Once located in the body cavity and in contact with an interior surface thereof, biologically active compound 166 establishes a "pharmacological barrier" between the interior of the body cavity and the opening in the body cavity wall. This "pharmacological barrier" helps prevent tumor cell implantation in the port site wound and/or the contamination of the port site wound with viable infectious microbes.

EIGHTH EMBODIMENT OF THE INVENTION

Now referring to FIGS. 34–37, there is shown a cannula 302 advanced through an opening 322 in a wall 320 of a body cavity 324. Cannula 302 includes a plurality of sealing members 304, 306, 308, and 310 attached to exterior surface 312 of cannula 302. Sealing members 304, 306, 308, and 310 are attached to exterior surface 312 such that sealing members 304, 306, 308, and 310 are spaced apart from each other along a longitudinal axis 330 of cannula 302. Each sealing member 304, 306, 308, and 310 defines a fluid impervious bladder for receiving a fluid, such as air. Other types of sealing members are also contemplated, for example a number of disks which are spaced apart from each other along longitudinal axis 330 of cannula 302. Cannula 302 also includes a number of valves 314, 316, and 318 attached to exterior surface 312 of cannula 302. Cannula 302 also includes a fourth valve (not shown) attached to exterior surface 312. The fourth valve is identical to valves 314, 316, and 318 but is attached to exterior surface 312 on the opposite side of cannula 302 as compared to valve 316. Valves 314, 316, 318, and the fourth valve can be any of a number of well known valves capable of maintaining and then releasing a fluid under pressure (e.g. a trumpet valve).

Each valve 314, 316, 318, and the fourth valve is in fluid communication with one sealing member 304, 306, 308, or 310. Specifically, valve 314 is in fluid communication with sealing member 310 via a channel (not shown) defined in cannula 302. Valve 316 is in fluid communication with sealing member 308 via another channel (not shown) defined in cannula 302. Valve 318 is in fluid communication with sealing member 306 via another channel (not shown) defined in cannula 302. The fourth valve is in fluid communication with sealing member 304 via another channel (not shown) defined in cannula 302. It should be understood that the above discussed channels are identical to and function in substantially the same manner as channel 195 as described in reference to sleeve 168 (see FIGS. 19–22). Therefore, it should be appreciated that the channels defined in cannula 302 allow a fluid, such as air, to be advanced into and withdrawn from each fluid impervious bladder defined by sealing member 304, 306, 308, and 310.

Figure 35:
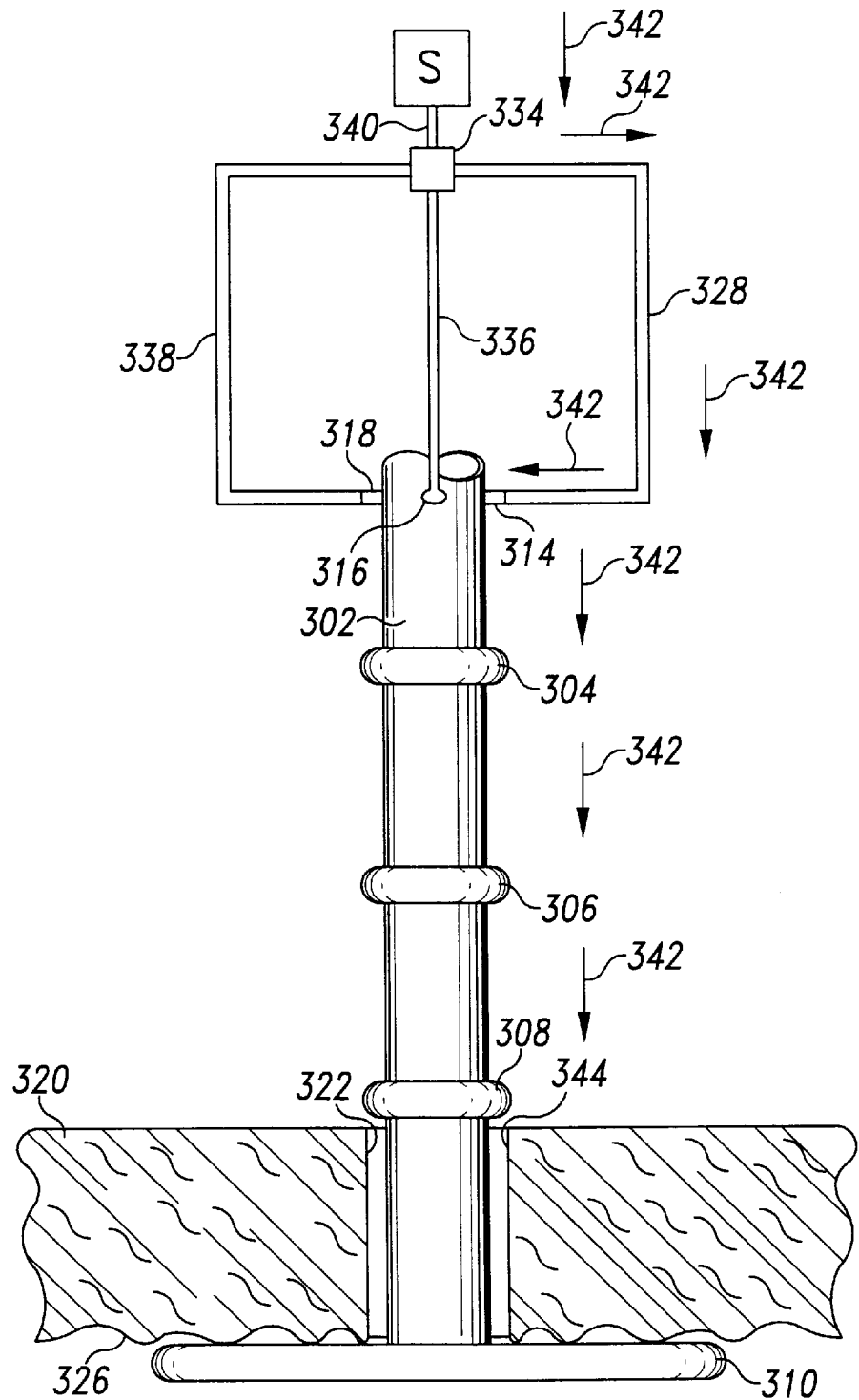
FIG. 35 is a view similar to FIG. 34, but with a fluid source schematically shown coupled to the cannula and one of the fluid bladder sealing members shown inflated.
Figure 36:
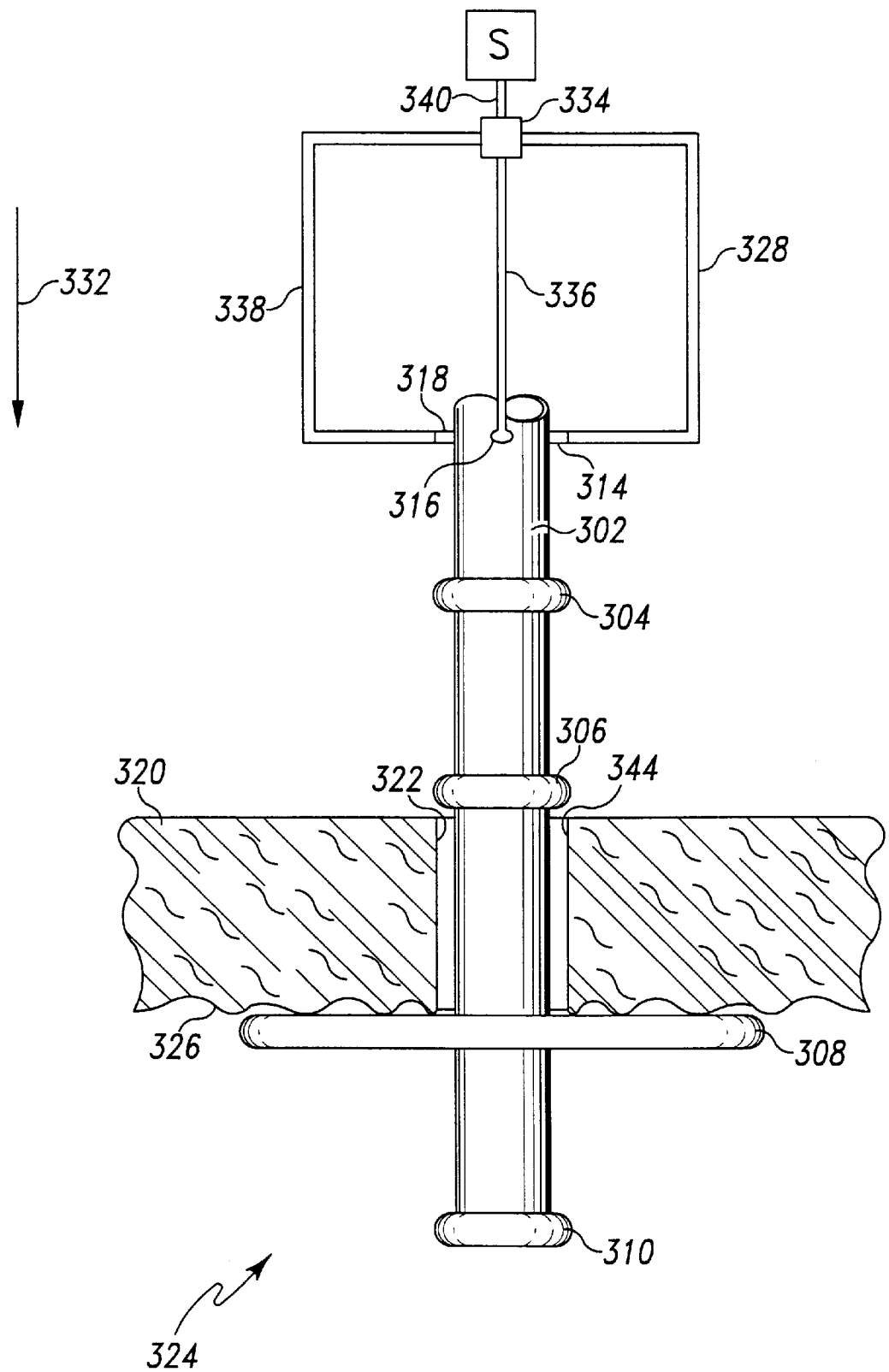
FIG. 36 is a view similar to FIG. 35, but with the cannula advanced further into the body cavity and a different fluid bladder sealing member shown inflated.
Figure 37:
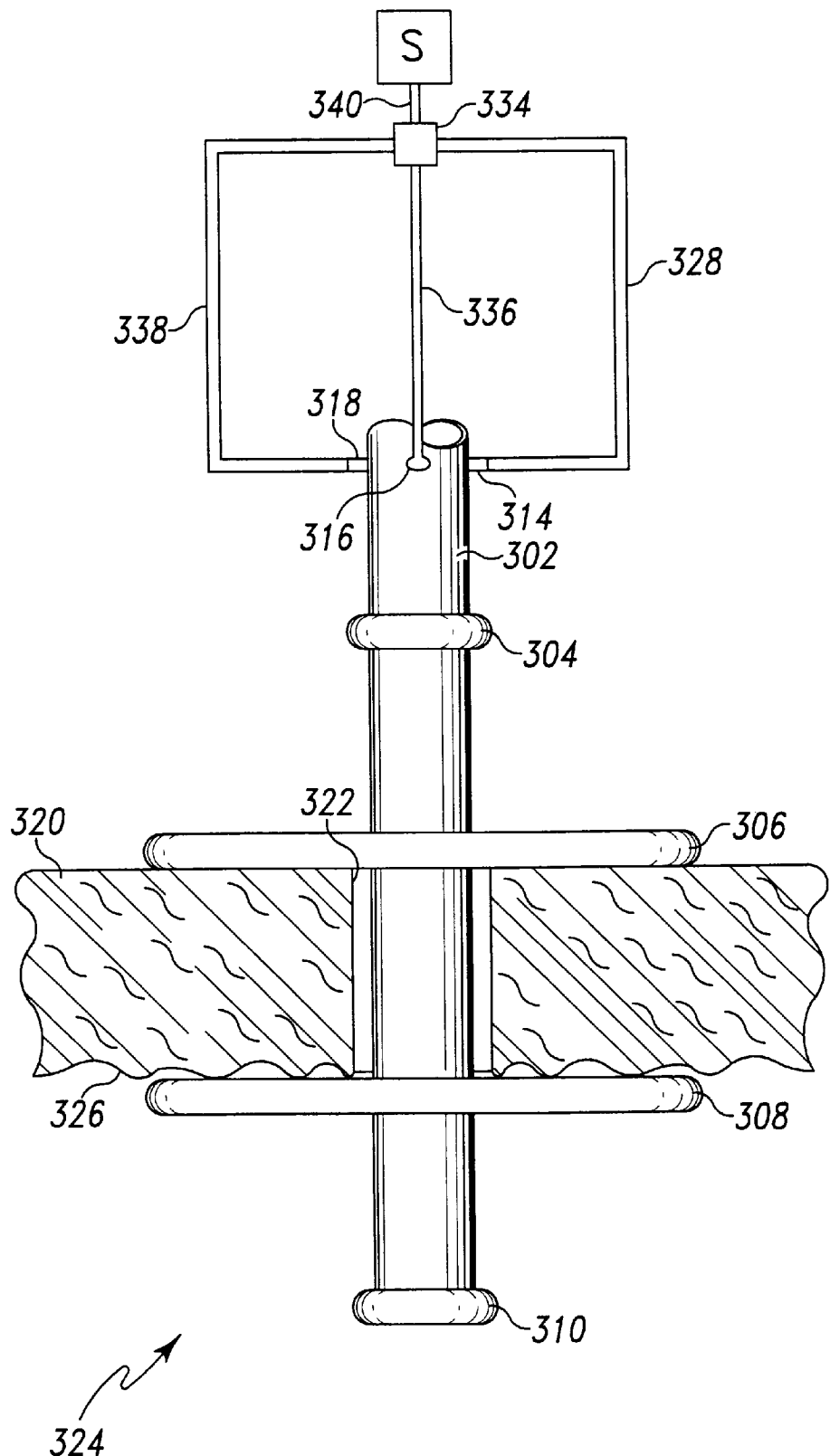
FIG. 37 is a view similar to FIG. 36, but with two fluid bladder sealing members shown inflated.

As shown in FIGS. 35, 36, and 37, valves 314, 316, and 318 are connected to a valve 334 via hoses 328, 336, and 338, respectively. The fourth valve is also connect to valve 334 via a hose (not shown). Valve 334 is connected to an air supply S via hose 340. Valve 334 is any well known valve capable of selectively directing an air flow delivered by air supply S to one or more of hoses 328, 336, 338 and the fourth hose. Air supply S can be manually operated (e.g. a syringe) or power driven (e.g. an air compressor).

Figure 34:
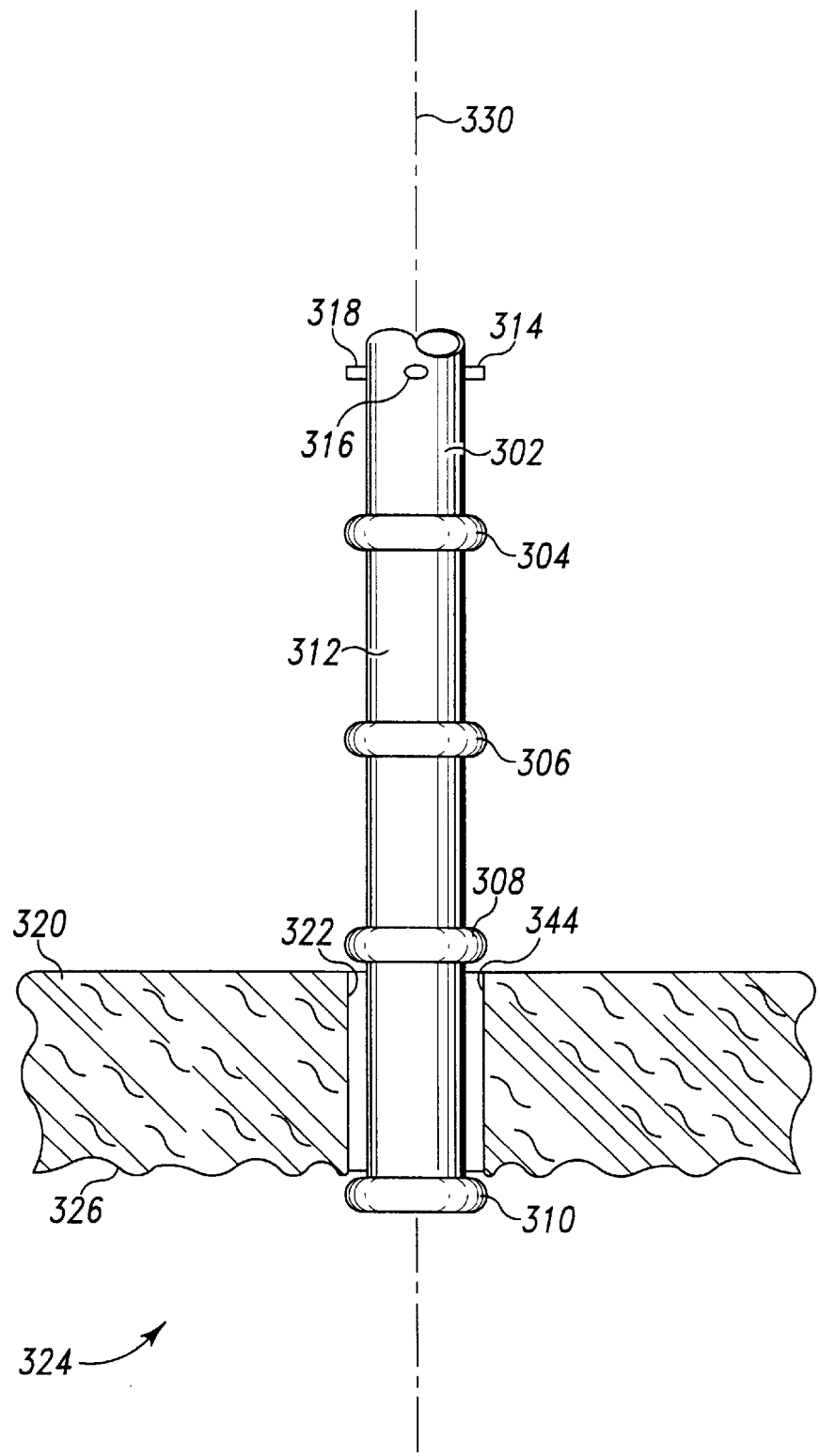
FIG. 34 is a fragmentary side elevational view of an alternative embodiment of the cannula of the trocar assembly of FIG. 1, with the cannula having a plurality of fluid bladder sealing members spaced apart from each other along the longitudinal axis of the cannula (note that the body cavity wall is shown in cross section for clarity of description)

It should be appreciated that the above described arrangement allows a surgeon to selectively place one or more of sealing member 304, 306, 308, and 310 in fluid communication with air supply S. For example, valve 334 can be adjusted such that only sealing member 310 is in fluid communication with air supply S. When valve 334 is placed in this configuration, an air flow generated by actuating air supply S will be directed in the following manner as illustrated by arrows 342 (see FIG. 35) from air supply S through hose 340, valve 334, hose 328, valve 314, the channel defined in cannula 302, and into the fluid impervious bladder defined by sealing member 310. Once the air flow enters the fluid impervious bag defined by sealing member 310, sealing member 310 inflates to form an annular disk (i.e. the second orientation for sealing member 310) as shown in FIG. 35. Sealing member 310 is deflated by releasing the air trapped in sealing member 310 through valve 314. Releasing air through valve 314 causes sealing member 310 to assume its pre-inflation configuration (i.e. the first orientation for sealing member 310) as shown in FIG. 34.

It should be appreciated that sealing members 308, 306, and 304 are inflated and deflated in substantially the same manner. For example, sealing member 308 is inflated by adjusting valve 334 such that air supply S is in fluid communication with hose 336 and then advancing an air flow through hose 336, valve 316 the channel defined in cannula 302, and into the fluid impervious bag defined by sealing member 308. Once the air flow enters the fluid impervious bag defined by sealing member 308, sealing member 308 inflates to form an annular disk as shown in FIG. 36. Sealing member 308 is deflated by releasing the air trapped in sealing member 308 through valve 316. Releasing air through valve 316 causes sealing member 308 to assume its pre-inflation configuration as shown in FIG. 34.

When performing a medical procedure, such as laparoscopic surgery, cannula 302 can be substituted for the combination of sleeve 18 and cannula 14 which are described above in reference to the first embodiment of the invention. In addition, cannula 302 is used in a similar way as that described above for the combination of sleeve 18 and cannula 14. Specifically, a trocar (not shown) is positioned within the lumen (not shown) of cannula 302. The trocar is then placed in contact with, and advanced through, body cavity wall 320 to create opening 322 (see FIG. 34). Preferably, cannula 302 and the trocar are simultaneously advanced through opening 322 and into body cavity 324, and as shown in FIG. 35, once cannula 302 is located within opening 322, sealing member 310 is inflated and cannula 302 is positioned such that sealing member 310 contacts an interior surface 326 of body cavity wall 320. Having sealing member 310 in contact with interior surface 326 prevents fluid communication between an area inside of body cavity 324 and an area outside of body cavity 324 through a space 344 defined between opening 322 in body cavity wall 320 and cannula 302. The trocar is then completely removed from the lumen of cannula 302 such that the lumen provides an access into body cavity 324.

Referring now to FIG. 36, sealing member 310 can be deflated and cannula 302 moved in a direction indicated by arrow 332 so as to further advance cannula 302 into body cavity 324. Once cannula 302 is repositioned in the above described manner, sealing member 308 is inflated and positioned in contact with interior surface 326 of body cavity wall 320. Having sealing member 308 in contact with interior surface 326 prevents fluid communication between an area inside of body cavity 324 and an area outside of body cavity 324 through space 344 defined between opening 322 in body cavity wall 320 and cannula 302. Cannula 302 can also be positioned relative to opening 322 such that sealing members 306 or 304 can be inflated and positioned in contact with interior surface 326 and thus prevent fluid communication between an area inside of body cavity 324 and an area outside of body cavity 324 through space 344 defined between opening 322 in body cavity wall 320 and cannula 302. Being able to locate cannula 302 relative to opening 322 in the aforementioned positions and still prevent the above described fluid communication is an important aspect of the present invention. Specifically, being able to move cannula 302 in the above described manner provides a surgeon with added flexibility in positioning cannula 302 within body cavity 324 (and therefore any medical instruments inserted into body cavity 324 via cannula 302) while protecting opening 322 from contamination with cancerous or infectious cells. Thus, having sealing members 304, 306, 308, and 310 attached to exterior surface 312 of cannula 302 in the above described manner enhances the surgeon's ability to successfully complete the surgery while protecting opening 322 from contamination with cancerous or infectious cells.

As shown in FIG. 37, two sealing members (e.g. sealing members 304 and 308) can be inflated simultaneously and positioned relative to body cavity wall 320 such that body cavity wall 320 is interposed between the two inflated sealing members. Having body cavity wall 320 interposed between two inflated sealing members stabilizes sleeve 302 in opening 322 and prevents any uncontrolled loss of the pneumoperitoneum.

After completing the medical procedure utilizing cannula 302, any medical instruments and/or specimens positioned within body cavity 324 are withdrawn therefrom through the lumen of cannula 302. Insufflation gas is then allowed to rapidly escape from body cavity 324 through the lumen of cannula 302.

Once substantially all the insufflation gas has escaped from body cavity 324 (i.e. body cavity 324 has been desufflated) sealing members 304, 306, 308, and 310 are all deflated, thereby facilitating the removal of cannula 302 from opening 322.

Thus, it should be understood that cannula 302 including sealing members 304, 306, 308, and 310 are the last components to be removed from body cavity 324 by the surgeon (not shown). Removing cannula 302 including sealing members 304, 306, 308, and 310 last ensures that opening 322 (i.e. the port site wound) remains protected against tumor cell implantation or contamination with an infectious agent in the same manner as described above in reference to sleeve 18.

CONCLUSION

Based upon the above description it will be understood by those skilled in the art that the present invention provides a medical apparatus for protecting a port site wound which adds only a minimal amount of bulk to the diameter of a trocar assembly. In addition, it will be understood by those skilled in the art that the present invention provides a medical apparatus for continuous protection of a port site wound which enables the independent movement of a cannula or trocar assembly, thus allowing the surgeon to functionally utilize the cannula and instruments to their fullest design. Moreover, it will be understood by those skilled in the art that the medical apparatus of the present invention can be retrofit to existing trocar assembly technology. Furthermore, the medical apparatus of the present invention allows minimally invasive surgical techniques, such as laparoscopic surgery, to be safely applied to cancer surgery. In addition, the medical apparatus of the present invention serves as a platform upon which additional technology (e.g. sensors or visual platforms) may be placed inside the abdomen and used in conjunction with laparoscopic surgery.

While the invention has been illustrated and described in detail in the drawings and foregoing description, such illustration and description is to be considered as exemplary and not restrictive in character, it being understood that only the preferred embodiments have been shown and described and that all changes and modifications that come within the spirit of the invention are desired to be protected. For example, while the mechanism described above for moving the sealing members from the first orientation to the second orientation has many benefits, other mechanisms may be used. One such mechanism may utilize pressure in the body cavity to force the sealing members against the interior surface thereof. Additional mechanisms which can be used to move the sealing members include the use of pistons attached to the sealing members, cords attached to the sealing members and a screw mechanism for actuating the sealing members. Furthermore, a system of tubes integrated in the sleeve can be used to deliver the biologically active compound to the sealing members via capillary action. Moreover, a sponge like material having a biologically active compound disposed thereon can be attached to the sleeves or cannula of the present invention such that when the sleeve or cannula is positioned within a port site wound the sponge like material and therefore the biologically active compound comes into contact with a sidewall of the port site wound so as to prevent viable cells from being implanted therein.

Additionally, other materials are contemplated for use in making the sealing member. For example, a cannula or sleeve utilizing thin, overlapping, filamentous bristles which create a pliable sealing member are contemplated. In addition, a material such as a sponge can be used to create a sealing member, particularly if the sponge material has any of the above described biologically active compounds disposed thereon. Moreover, foam, or other materials which are capable of altering their degree of pliability and serve as sealing members are contemplated. In addition, the beads may also have electric or magnetic characteristics which facilitates the conversion of the sealing members from their soft, pliable state, to their stable rigid state.

What is claimed is:

1. A medical apparatus positionable within an opening in a wall of a body cavity, comprising:
 a trocar assembly including a cannula and a trocar, wherein (1) said cannula has a lumen defined therein, (2) said trocar is positionable between a first trocar position and a second trocar position, (3) said trocar is positioned within said lumen of said cannula when said trocar is positioned at said first trocar position, and (4) said trocar is completely removed from said lumen of said cannula when said trocar is positioned at said second trocar position; and
 a sleeve having a passageway extending therethrough, and a number of sealing members extending therefrom, wherein (1) said sealing members are movable between (a) an first orientation in which said sealing members are positioned to facilitate advancement of said sleeve into said opening and (b) a second orientation in which said sealing members are positioned in contact with an interior surface of said wall of said body cavity which surrounds a space defined between said opening of said body cavity and said sleeve, (2) said cannula is positionable between a first cannula position and a second cannula position, (3) said cannula is positioned within said passageway of said sleeve when said cannula is positioned at said first cannula position, (4) said cannula is completely removed from said passageway of said sleeve when said cannula is positioned at said second cannula position, (5) said cannula is movable between said first cannula position and said second cannula position when said sealing members are positioned in said second orientation, and (6) said sealing members are movable between said first orientation and said second orientation when said cannula is positioned within said passageway of said sleeve.

2. The medical apparatus of claim 1, further comprising:
 a gasket interposed between said cannula and said sleeve when said cannula is positioned at said first cannula position such that a seal is formed between said cannula and said sleeve.

3. The medical apparatus of claim 1, wherein:
 said sleeve has a distal end and said sealing members extend therefrom.

4. The medical apparatus of claim 1, wherein:
 said sealing members have a first end portion which is attached to a sleeve sidewall, and
 said sealing members further have a second end portion which are configured to define an orifice when said sealing members are positioned at said first orientation.

5. The medical apparatus of claim 1, further comprising:
 an actuator for controlling movement of said sealing members between said first orientation and said second orientation.

6. A medical apparatus, comprising:
 a trocar assembly including a cannula and a trocar, wherein (1) said cannula has a lumen defined therein, (2) said trocar is positionable between a first trocar position and a second trocar position, (3) said trocar is positioned within said lumen of said cannula when said trocar is positioned at said first trocar position, and (4) said trocar is completely removed from said lumen of said cannula when said trocar is positioned at said second trocar position;
 a sleeve having a passageway extending therethrough, and a number of sealing members extending therefrom, wherein (1) said cannula is positionable between a first cannula position and a second cannula position, (2) said cannula is positioned within said passageway of said sleeve when said cannula is positioned at said first cannula position, (3) said cannula is completely removed from said passageway of said sleeve when said cannula is positioned at said second cannula position, (4) said sleeve is positionable within an opening defined in a wall of a body cavity, (5) said sealing members are movable between (a) a first orientation in which said sealing members are positioned to facilitate advancement of said sleeve into said opening, and (b) a second orientation in which said sealing members are positioned in contact with an interior surface of said wall of said body cavity which surrounds a space defined between said opening of said body cavity and said sleeve; and
 an actuator for controlling movement of said sealing members between said first orientation and said second orientation,
 wherein said actuator includes a guide member positionable at (1) a first position in which said sealing members are maintained in said first orientation, and (2) a second position in which said sealing members are allowed to assume said second orientation.

7. The medical apparatus of claim 6, wherein:
 said actuator further includes a handle connected to said guide member.

8. A medical procedure, comprising the steps of:
 creating an opening in a wall of a body cavity;
 advancing a medical apparatus through said opening and into said body cavity, said medical apparatus including (1) a sleeve having a number of sealing members connected thereto and a passageway extending therethrough, (2) a trocar assembly positioned within said passageway of said sleeve, said trocar assembly including a cannula and a trocar, wherein (a) said sealing members are movable between (i) an first orientation in which said sealing members are positioned to facilitate advancement of said sleeve into said opening and (ii) a second orientation in which said sealing members are positioned in contact with an interior surface of said wall of said body cavity which surrounds a space defined between said opening of said body cavity and said sleeve (b) said cannula is completely removable from said passageway of said sleeve when said sealing members are positioned in said second orientation, (c) said cannula has a lumen defined therein, (d) said trocar is completely removable from said lumen of said cannula, and (e) said sealing members are movable between said first orientation and said second orientation when said cannula is positioned within said passageway of said sleeve; and
 positioning said sealing members in said second orientation.

9. The medical procedure of claim 8, further comprising the step of:

moving said cannula in an axial direction relative to said sleeve while (1) said cannula is positioned within said passageway of said sleeve and (2) said sealing members are in contact with said interior surface of said body cavity.

10. The medical procedure of claim 8, wherein:

said advancing step includes the step of simultaneously advancing said sleeve and said trocar assembly through said opening and into said body cavity.

11. The medical procedure of claim 8, wherein:

said advancing step includes the step of maintaining said sealing members at a first orientation which facilitates advancement of said sleeve through said opening and into said body cavity.

12. The medical procedure of claim 11, wherein:

said positioning step includes the step of moving said sealing members from said first orientation to a second orientation, and when said sealing members are positioned at said second orientation, said sealing members are positioned to prevent fluid communication between an area inside of said body cavity and an area outside of said body cavity through a space defined between said opening of said body cavity and said sleeve.

13. The medical procedure of claim 12, wherein:

said advancing step further includes the step of positioning a guide member at a first position so that said sealing members are maintained in said first orientation; and said positioning step further includes the step of moving said guide member from said first position to a second position so that said sealing members are allowed to assume said second orientation.

14. The medical procedure of claim 8, wherein:

said creating step includes the step of creating said opening in said wall of said body cavity with said trocar.

15. The medical procedure of claim 8, wherein:

said medical apparatus further includes a bearing member secured to an interior sidewall of said sleeve such that said bearing member contacts said cannula when said cannula is positioned within said passageway of said sleeve, and said bearing member forms a seal between said interior sidewall of said sleeve and said cannula so as to prevent fluid communication between an area inside of a body cavity and an area outside of said body cavity through a space defined between said sleeve and said cannula.

16. A medical procedure, comprising the steps of:

creating an opening in a wall of a body cavity;

advancing a medical apparatus through said opening and into said body cavity, said medical apparatus including (1) a sleeve having a number of sealing members connected thereto and a passageway extending therethrough, (2) a trocar assembly positioned within said passageway of said sleeve, said trocar assembly including a cannula and a trocar, wherein (a) said cannula is completely removable from said passageway of said sleeve, (b) said cannula has a lumen defined therein, and (c) said trocar is completely removable from said lumen of said cannula;

positioning said sealing members to contact an interior surface of said body cavity; and completely removing said trocar from said lumen of said cannula while said sleeve remains positioned within said opening in said wall of said body cavity.

17. A medical procedure, comprising the steps of:

creating an opening in a wall of a body cavity;

advancing a medical apparatus through said opening and into said body cavity, said medical apparatus including (1) a sleeve having a number of sealing members connected thereto and a passageway extending therethrough, (2) a trocar assembly positioned within said passageway of said sleeve, said trocar assembly including a cannula and a trocar, wherein (a) said cannula is completely removable from said passageway of said sleeve, (b) said cannula has a lumen defined therein, and (c) said trocar is completely removable from said lumen of said cannula;

positioning said sealing members to contact an interior surface of said body cavity; and completely removing said cannula from said passageway of said sleeve while said sleeve remains positioned within said opening in said wall of said body cavity.

18. A medical apparatus, comprising:

a trocar assembly including a cannula and a trocar, wherein (1) said cannula has a lumen defined therein, and (2) said trocar is completely removable from said lumen of said cannula; and a sleeve having a passageway extending therethrough and a number of sealing members extending therefrom, wherein (1) said sealing members are movable between (a) an first orientation in which said sealing members are positioned to facilitate advancement of said sleeve into an opening defined in a wall of a body cavity, and (b) a second orientation in which said sealing members are positioned to prevent fluid communication between an area inside of said body cavity and an area outside of said body cavity through a space defined between said opening in said wall of said body cavity and said sleeve, (2) said cannula is completely removable from said sleeve when said sealing members are positioned in said second orientation, and (3) said sealing members are movable between said first orientation and said second orientation when said cannula is positioned within said passageway of said sleeve.

19. The medical apparatus of claim 18, further comprising a bearing member secured to an interior sidewall of said sleeve such that said bearing member contacts said cannula when said cannula is positioned within said passageway of said sleeve, wherein:

said bearing member forms a seal between said interior sidewall of said sleeve and said cannula so as to prevent fluid communication between an area inside of said body cavity and an area outside of said body cavity through a second space defined between said sleeve and said cannula.

* * * * *